(12) United States Patent
Zamierowski

(10) Patent No.: US 7,410,495 B2
(45) Date of Patent: Aug. 12, 2008

(54) MEDICAL CLOSURE CLIP SYSTEM AND METHOD

(75) Inventor: David S. Zamierowski, Shawnee Mission, KS (US)

(73) Assignee: KCI Licensing, Inc., San Antonio, TX (US)

( * ) Notice: Subject to any disclaimer, the term of this patent is extended or adjusted under 35 U.S.C. 154(b) by 407 days.

(21) Appl. No.: 11/103,056

(22) Filed: Apr. 11, 2005

(65) Prior Publication Data
US 2005/0234510 A1    Oct. 20, 2005

Related U.S. Application Data

(63) Continuation-in-part of application No. 10/224,852, filed on Aug. 21, 2002.

(51) Int. Cl.
*A61B 17/08* (2006.01)
*A61D 1/00* (2006.01)

(52) U.S. Cl. ........................................... 606/216
(58) Field of Classification Search ............ 606/213, 606/215, 216, 221; 256/2, 6–9; 140/50; 24/112, 3.13, 369, 299, 371, 343, 380
See application file for complete search history.

(56) References Cited

U.S. PATENT DOCUMENTS

| | | | |
|---|---|---|---|
| 221,427 A * | 11/1879 | Sherman | 256/9 |
| 1,355,846 A | 10/1920 | Rannells | |
| 2,547,758 A | 4/1951 | Keeling | |
| 2,632,443 A | 3/1953 | Lesher | |
| 2,682,873 A | 7/1954 | Evans et al. | |
| 2,969,057 A | 1/1961 | Simmons | |
| 3,066,672 A | 12/1962 | Crosby, Jr. et al. | |
| 3,115,138 A | 12/1963 | McEvenny et al. | |

(Continued)

FOREIGN PATENT DOCUMENTS

AU    550575 A1    8/1982

(Continued)

OTHER PUBLICATIONS

Mendez-Eastman, Susan. When Wounds Won't Heal. RN. Jan. 1998, pp. 20-24.*

(Continued)

*Primary Examiner*—Todd E. Manahan
*Assistant Examiner*—Christina D Gettman

(57) ABSTRACT

A medical closure screen device for a separation of first and second tissue portions is provided, which includes a mesh screen comprising tubular vertical risers, vertical strands with barbed filaments, and horizontal spacers connecting the risers and strands in a grid-like configuration. An optional perimeter member partly surrounds the screen and can comprise a perimeter tube fluidically coupled with the vertical risers to form a tubing assembly. Various input/output devices can optionally be connected to the perimeter tube ends for irrigating and/or draining the separation according to methodologies of the present invention. Separation closure, irrigation and drainage methodologies are disclosed utilizing various combinations of closure screens, tubing, sutures, fluid transfer elements and gradient force sources. The use of mechanical forces associated with barbed strands for repositionably securing separated tissues together is disclosed. The use of same for eliminating or reducing the formation of subcutaneous voids or pockets, which can potentially form hematoma and seroma effects, is also disclosed. The device can be fabricated and the method practiced with clips having various configurations.

3 Claims, 43 Drawing Sheets

U.S. PATENT DOCUMENTS

| | | | |
|---|---|---|---|
| 3,367,332 A | 2/1968 | Groves | |
| 3,520,300 A | 7/1970 | Flower, Jr. | |
| 3,648,692 A | 3/1972 | Wheeler | |
| 3,682,180 A | 8/1972 | McFarlane | |
| 3,826,254 A | 7/1974 | Mellor | |
| 3,981,051 A * | 9/1976 | Brumlik | 24/447 |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,233,969 A | 11/1980 | Lock et al. | |
| 4,245,630 A | 1/1981 | Lloyd et al. | |
| 4,248,232 A | 2/1981 | Engelbrecht et al. | |
| 4,259,959 A * | 4/1981 | Walker | 606/221 |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman et al. | |
| 4,392,853 A | 7/1983 | Muto | |
| 4,392,858 A | 7/1983 | George et al. | |
| 4,419,093 A | 12/1983 | Deaton | |
| 4,419,097 A | 12/1983 | Rowland | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,339 A | 8/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,696,301 A | 9/1987 | Barabe | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,775,909 A | 10/1988 | Eisenburg | |
| 4,787,888 A | 11/1988 | Fox | |
| 4,826,494 A | 5/1989 | Richmond et al. | |
| 4,828,546 A | 5/1989 | McNeil et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,976,726 A | 12/1990 | Haverstock | |
| 4,985,019 A | 1/1991 | Michelson | |
| 5,007,921 A * | 4/1991 | Brown | 606/221 |
| 5,007,936 A | 4/1991 | Woolson | |
| 5,019,083 A | 5/1991 | Klapper et al. | |
| 5,037,397 A | 8/1991 | Kalt et al. | |
| 5,045,054 A | 9/1991 | Hood et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,112,338 A | 5/1992 | Anspach, III | |
| 5,134,994 A | 8/1992 | Say | |
| 5,149,331 A | 9/1992 | Ferdman et al. | |
| 5,167,613 A | 12/1992 | Karami et al. | |
| 5,169,399 A | 12/1992 | Ryland et al. | |
| 5,176,663 A | 1/1993 | Svedman et al. | |
| 5,215,522 A | 6/1993 | Page et al. | |
| D337,639 S | 7/1993 | Beckman | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,291,887 A | 3/1994 | Stanley et al. | |
| 5,298,015 A | 3/1994 | Komatsuzaki et al. | |
| 5,318,570 A | 6/1994 | Hood et al. | |
| 5,342,376 A | 8/1994 | Ruff | |
| 5,344,415 A | 9/1994 | DeBusk et al. | |
| 5,358,494 A | 10/1994 | Svedman | |
| 5,383,897 A | 1/1995 | Wholey | |
| 5,423,885 A | 6/1995 | Williams | |
| 5,437,622 A | 8/1995 | Carion | |
| 5,437,651 A | 8/1995 | Todd et al. | |
| 5,507,833 A | 4/1996 | Bohn | |
| 5,522,901 A | 6/1996 | Thomas et al. | |
| 5,527,293 A | 6/1996 | Zamierowski | |
| D372,309 S | 7/1996 | Heldreth | |
| 5,549,584 A | 8/1996 | Gross | |
| 5,556,375 A | 9/1996 | Ewall | |
| 5,580,353 A | 12/1996 | Mendes | |
| 5,584,859 A | 12/1996 | Brotz | |
| 5,607,388 A | 3/1997 | Ewall | |
| 5,630,819 A | 5/1997 | Ashby et al. | |
| 5,636,643 A | 6/1997 | Argenta et al. | |
| 5,645,081 A | 7/1997 | Argenta et al. | |
| 5,716,360 A | 2/1998 | Baldwin et al. | |
| 5,738,686 A | 4/1998 | Budein-Meesenburg et al. | |
| 5,785,700 A | 7/1998 | Olson | |
| 5,800,546 A | 9/1998 | Marik et al. | |
| 5,827,246 A | 10/1998 | Bowen | |
| 5,846,244 A | 12/1998 | Cripe | |
| 5,911,222 A | 6/1999 | Lawrence et al. | |
| 5,921,972 A | 7/1999 | Skow | |
| 5,931,855 A | 8/1999 | Buncke | |
| 5,941,859 A | 8/1999 | Lerman | |
| 6,071,267 A | 6/2000 | Zamierowski | |
| 6,113,618 A | 9/2000 | Nic | |
| 6,126,659 A | 10/2000 | Wack | |
| 6,135,116 A | 10/2000 | Vogel et al. | |
| 6,142,982 A | 11/2000 | Hunt et al. | |
| 6,146,423 A | 11/2000 | Cohen et al. | |
| 6,159,246 A | 12/2000 | Mendes et al. | |
| 6,174,306 B1 | 1/2001 | Fleischmann | |
| 6,179,804 B1 | 1/2001 | Satterfield | |
| 6,190,391 B1 | 2/2001 | Stubbs | |
| 6,190,392 B1 | 2/2001 | Vandewalle et al. | |
| 6,203,563 B1 | 3/2001 | Fernandez | |
| 6,241,747 B1 | 6/2001 | Ruff | |
| 6,270,517 B1 | 8/2001 | Brotz | |
| RE37,358 E | 9/2001 | Del Rio et al. | |
| 6,287,316 B1 | 9/2001 | Agarwal et al. | |
| 6,293,929 B1 | 9/2001 | Smith et al. | |
| 6,345,623 B1 | 2/2002 | Heaton et al. | |
| 6,355,215 B1 | 3/2002 | Poggie et al. | |
| 6,377,653 B1 | 4/2002 | Lee et al. | |
| 6,398,767 B1 | 6/2002 | Fleischmann | |
| 6,430,427 B1 | 8/2002 | Lee et al. | |
| 6,488,643 B1 | 12/2002 | Tumey et al. | |
| 6,493,568 B1 | 12/2002 | Bell et al. | |
| 6,500,209 B1 | 12/2002 | Kolb | |
| 6,503,281 B1 | 1/2003 | Mallory | |
| 6,553,998 B2 | 4/2003 | Heaton et al. | |
| 6,620,132 B1 | 9/2003 | Skow | |
| 6,626,891 B2 | 9/2003 | Ohmstede | |
| 6,645,226 B1 | 11/2003 | Jacobs et al. | |

| | | |
|---|---|---|
| 6,669,735 B1 | 12/2003 | Pelissier |
| 6,685,681 B2 | 2/2004 | Lockwood et al. |
| 6,695,823 B1 | 2/2004 | Lina et al. |
| 6,726,706 B2 | 4/2004 | Dominguez |
| 6,752,794 B2 | 6/2004 | Lockwood et al. |
| 6,800,074 B2 | 10/2004 | Henley et al. |
| 6,814,079 B2 | 11/2004 | Heaton et al. |
| 6,991,643 B2 | 1/2006 | Saadat |
| 2002/0022861 A1 | 2/2002 | Jacobs et al. |
| 2002/0029063 A1 | 3/2002 | Wittmann |
| 2002/0077661 A1 | 6/2002 | Saadat |
| 2002/0099447 A1 | 7/2002 | Mears et al. |
| 2002/0115951 A1 | 8/2002 | Norstrem et al. |
| 2002/0116067 A1 | 8/2002 | Mears et al. |
| 2002/0120185 A1 | 8/2002 | Johnson |
| 2002/0143286 A1 | 10/2002 | Turmey |
| 2002/0183565 A1 | 12/2002 | Leavanoni et al. |
| 2003/0050594 A1 | 3/2003 | Zamierowski |
| 2003/0097135 A1 | 5/2003 | Pennenberg |
| 2004/0039415 A1 | 2/2004 | Zamierowski |
| 2005/0043818 A1 | 2/2005 | Bellon Caneiro et al. |

FOREIGN PATENT DOCUMENTS

| | | |
|---|---|---|
| AU | 745271 | 4/1999 |
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358 302 A2 | 3/1990 |
| EP | 1 018 967 B1 | 8/2004 |
| GB | 692578 | 6/1953 |
| GB | 2 197 789 A | 6/1988 |
| GB | 2 200 357 A | 1/1990 |
| GB | 2 220 357 A | 1/1990 |
| GB | 2 235 877 | 3/1991 |
| GB | 2 235 877 A | 3/1991 |
| GB | 2333965 A | 8/1999 |
| GB | 2329127 B | 8/2000 |
| JP | 4129536 | 4/1992 |
| SG | 71559 | 4/2002 |
| WO | WO80/02182 | 10/1980 |
| WO | WO 80/02182 | 10/1980 |
| WO | WO 93/09727 | 5/1993 |
| WO | WO 94/20041 | 9/1994 |
| WO | WO96/05873 | 2/1996 |
| WO | WO97/18007 | 5/1997 |
| WO | WO 99/13793 | 3/1999 |

OTHER PUBLICATIONS

Orringer, Jay, et al; "Management of Wounds in Patients with Complex Enterocutaneous Fistulas"; Surgery, Gynecology & Obstertrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed-Bi-directional Surgical Suture"; Journal of Textile and Apparel, Technology and Management, vol. 2, Issue 2, Spring 2002; pp. 1-5.

Kostyuchenok, B.M., et al; "Vacuum Treatment in the Surgical Management of Purulent Wounds"; Vestnik Khirurgi, Sep. 1986; pp. 18-21, and 6 page English translation thereof.

Davydov, Yu. A., et al; "Vacuum Therapy in the Treatment of Purulent Lactation Mastitis"; Vestnik Khirurgi, May 14, 1986; pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, May 2, 1986; pp. 42-46, 7 page English translation thereof.

Davydov, Yu. A., et al; "Concepts for the Clinical-Biological Management of Wound Process in the treatment of Purulent Wounds by Means of Vacuum Therapy"; Vestnik Khirurgi, Jul. 7, 1980; pp. 132-136, and 8 page English translation thereof.

Louis C. Argenta, MD and Michael J. Morykwas, PhD; "Vaccum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; Reliable, Inexpensive and Simple Suction Dressings:; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" Britsh Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

* cited by examiner

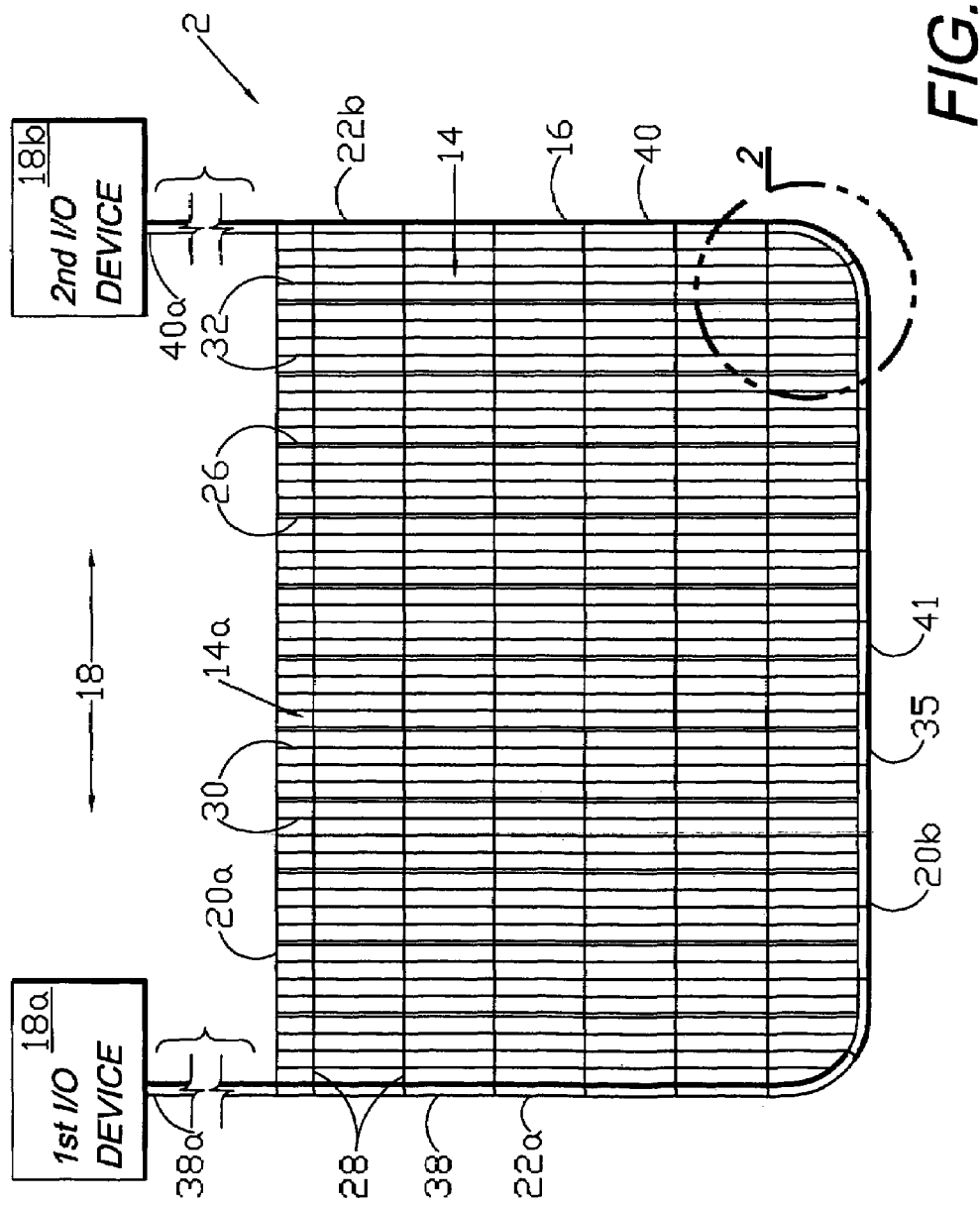

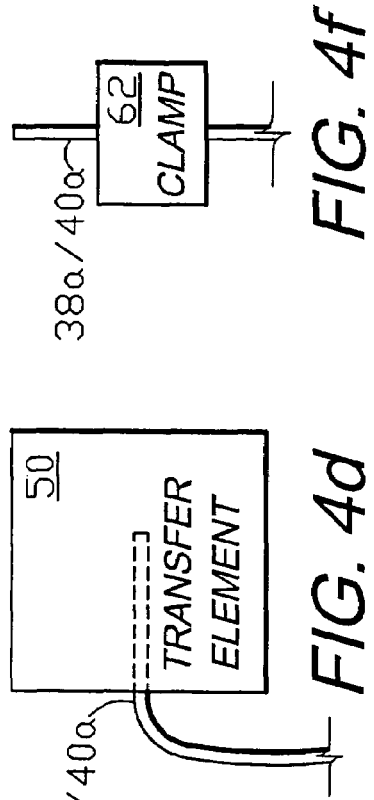
FIG. 4a
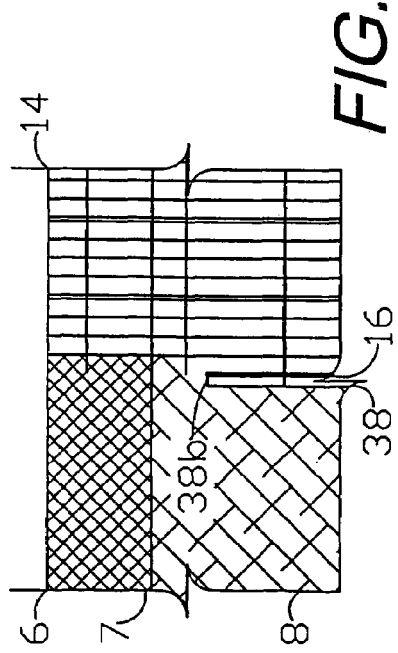
FIG. 4b
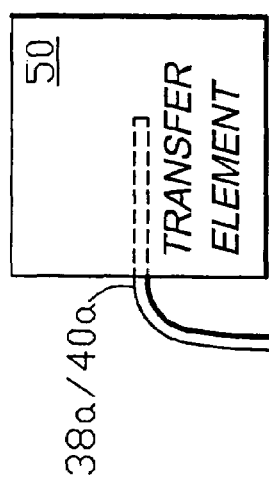
FIG. 4c
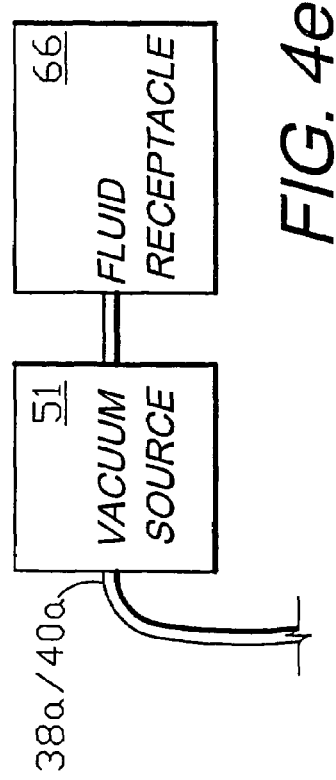
FIG. 4d
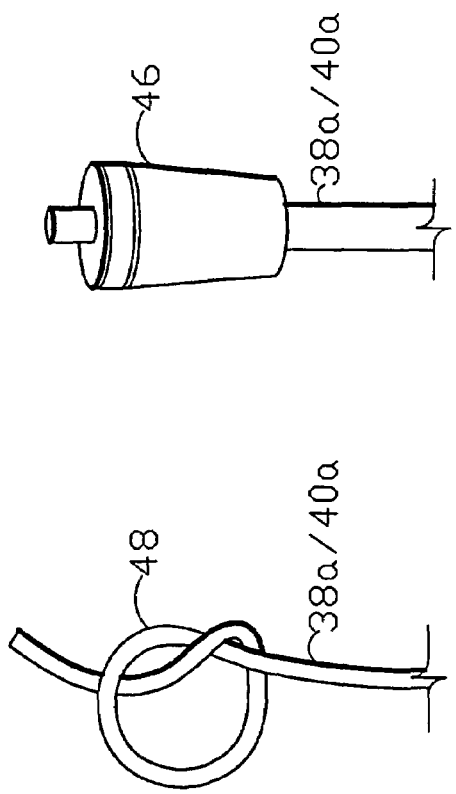
FIG. 4e
FIG. 4f

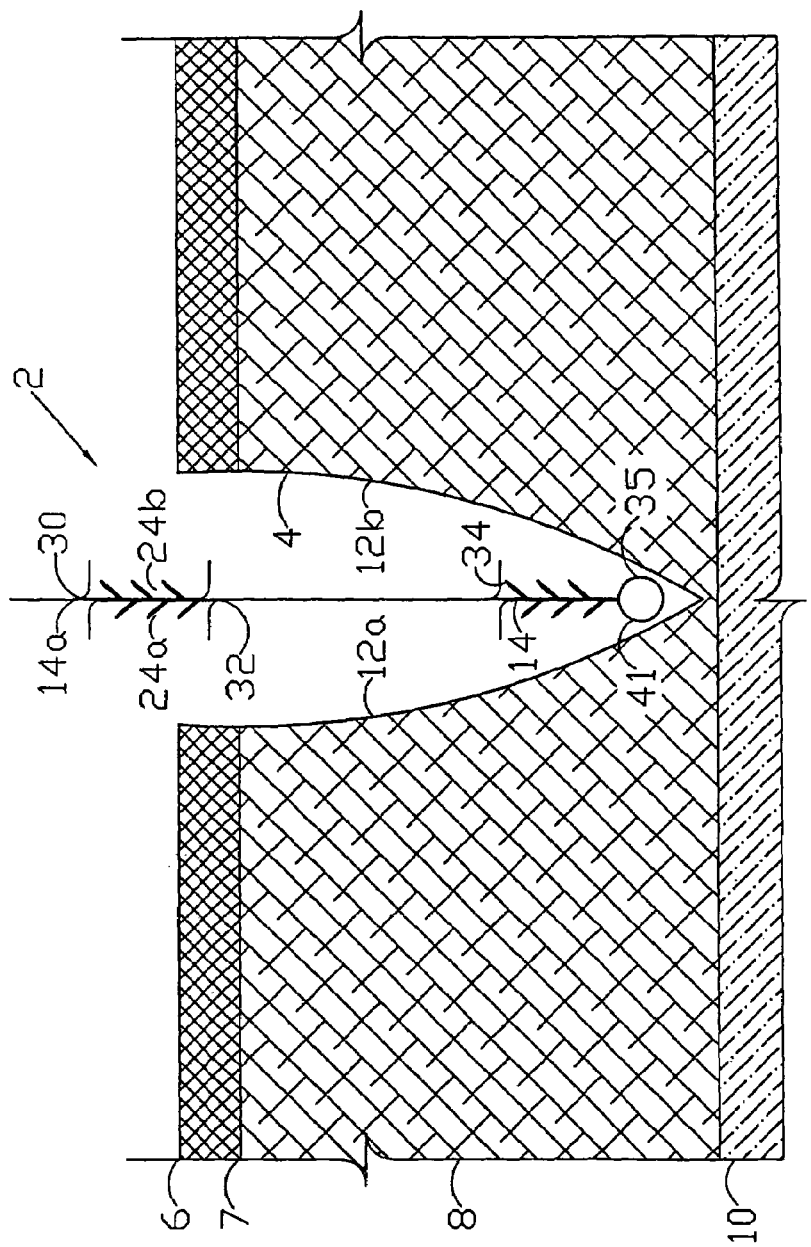

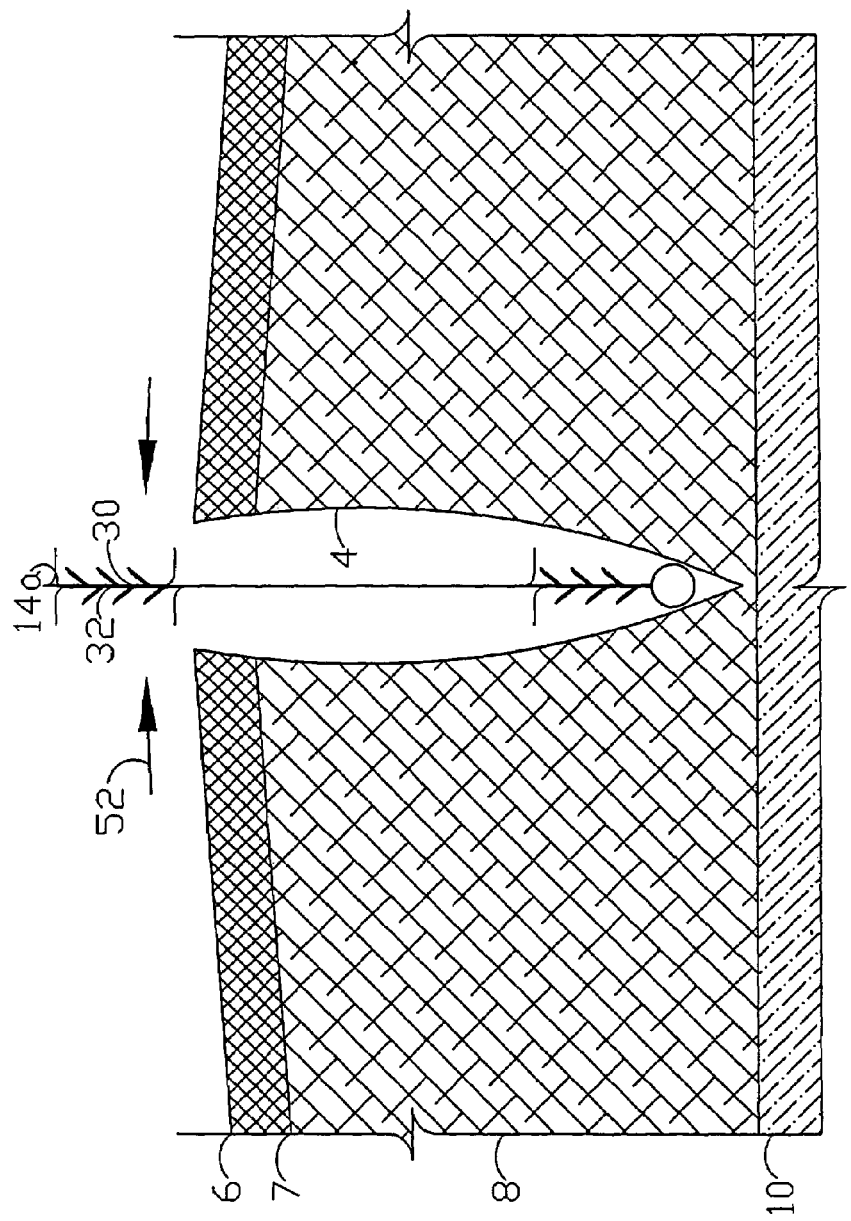

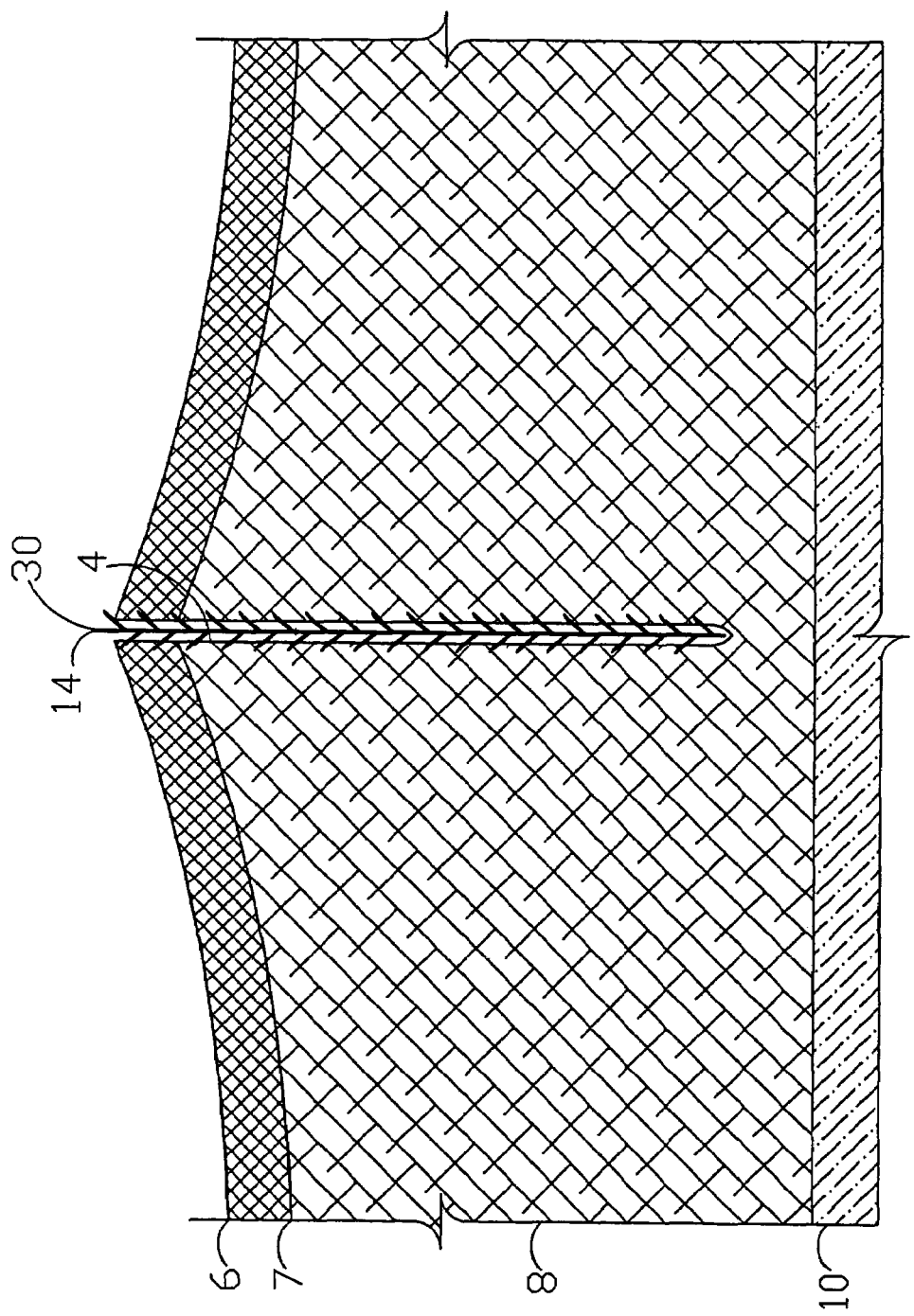

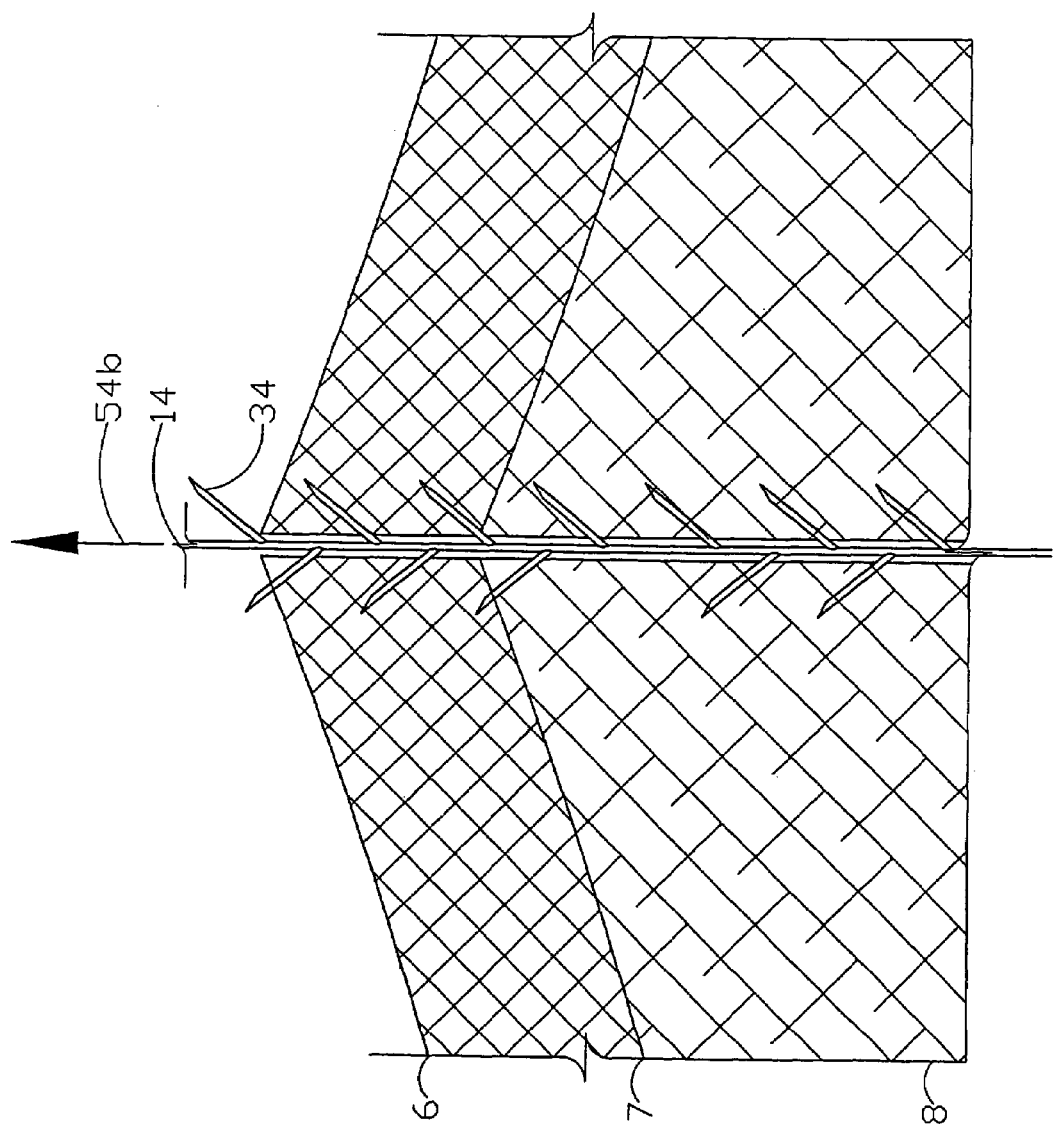

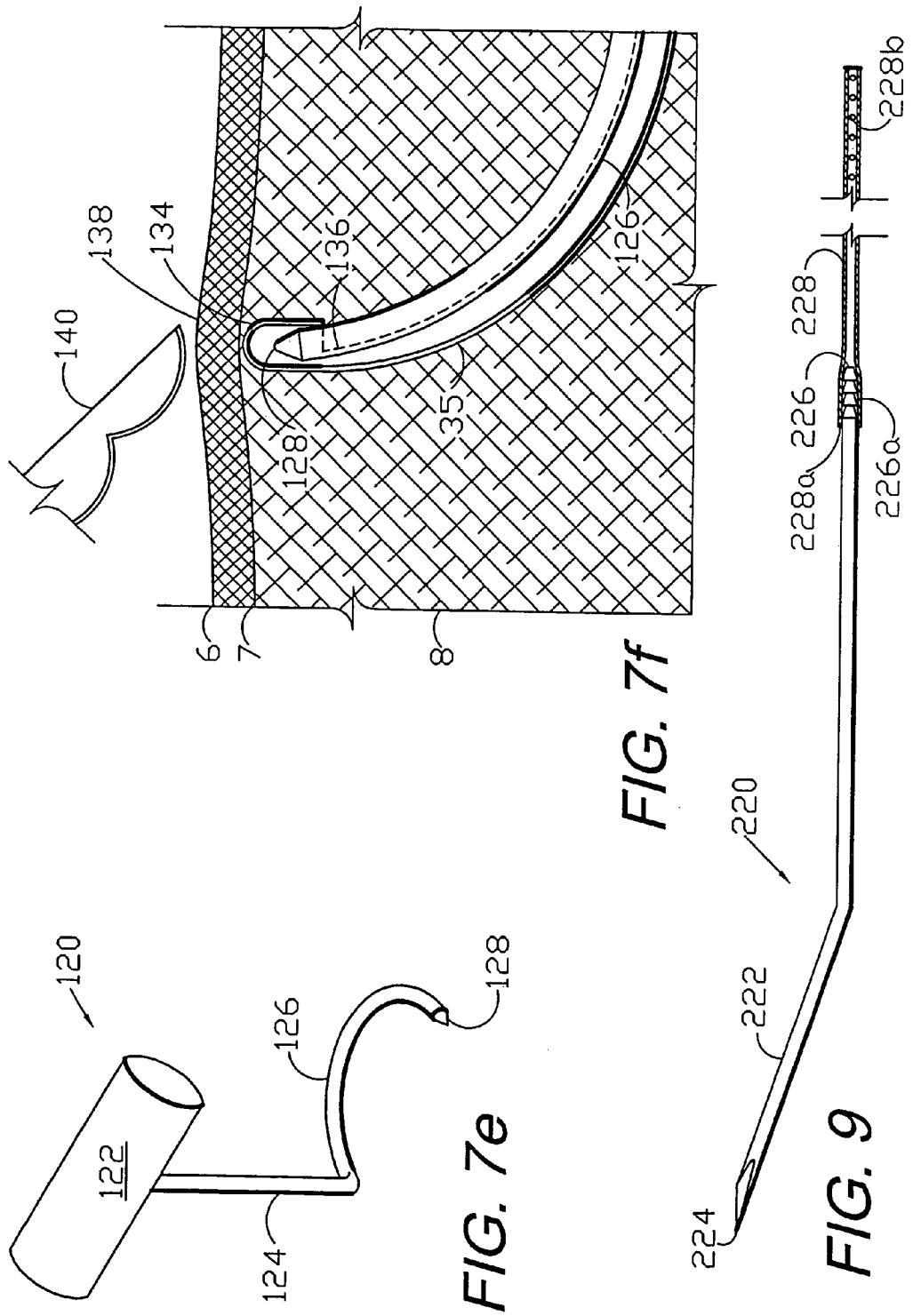

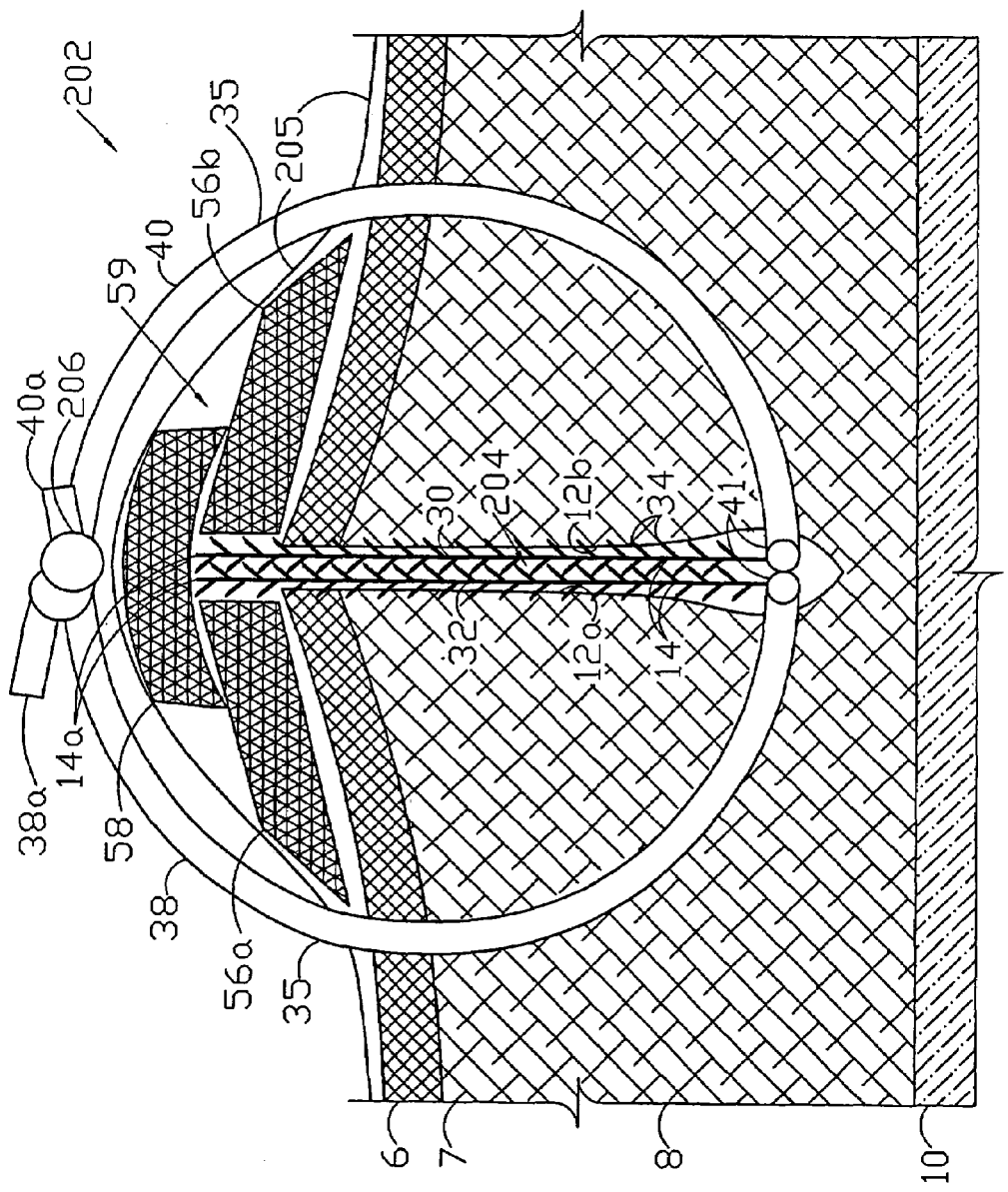

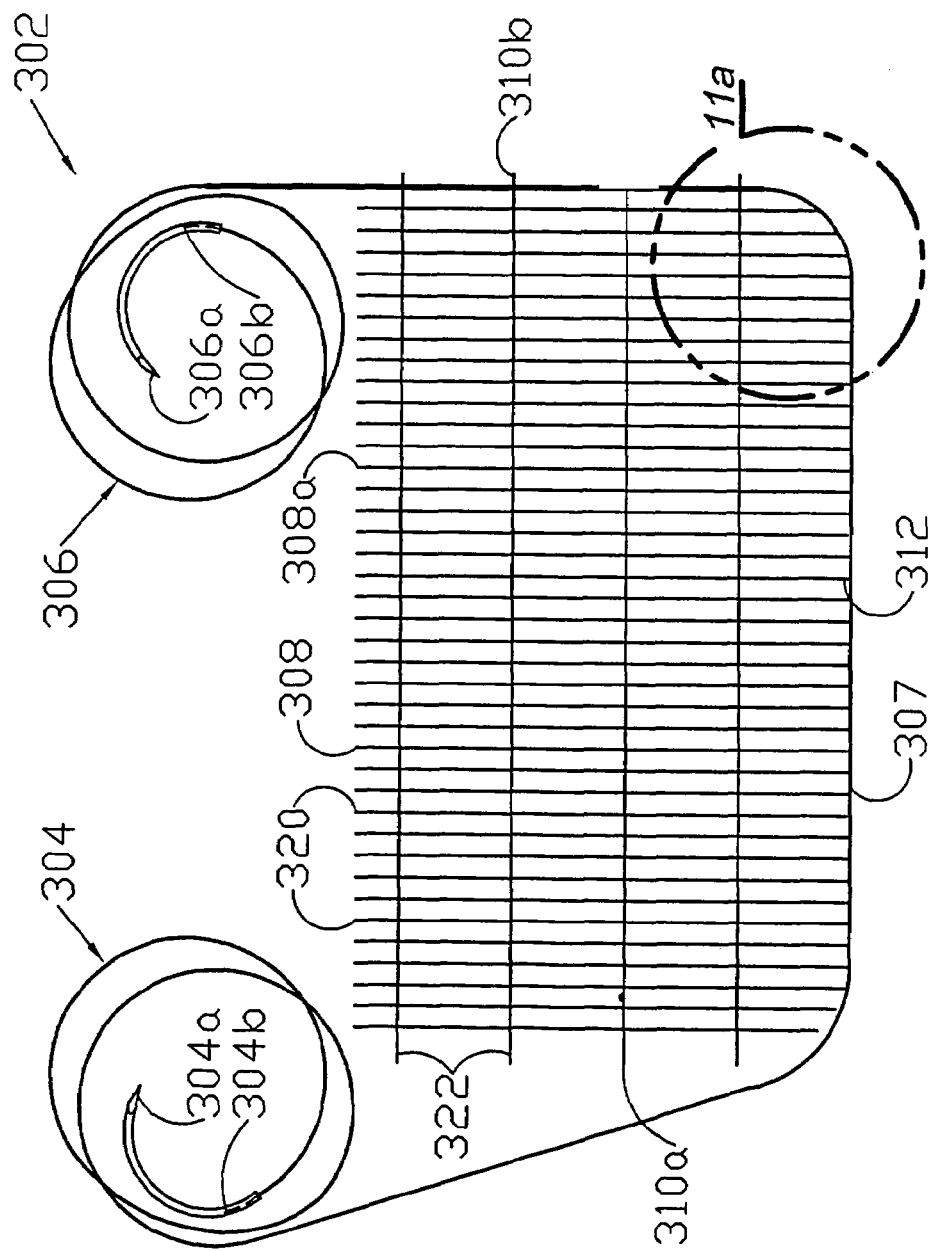

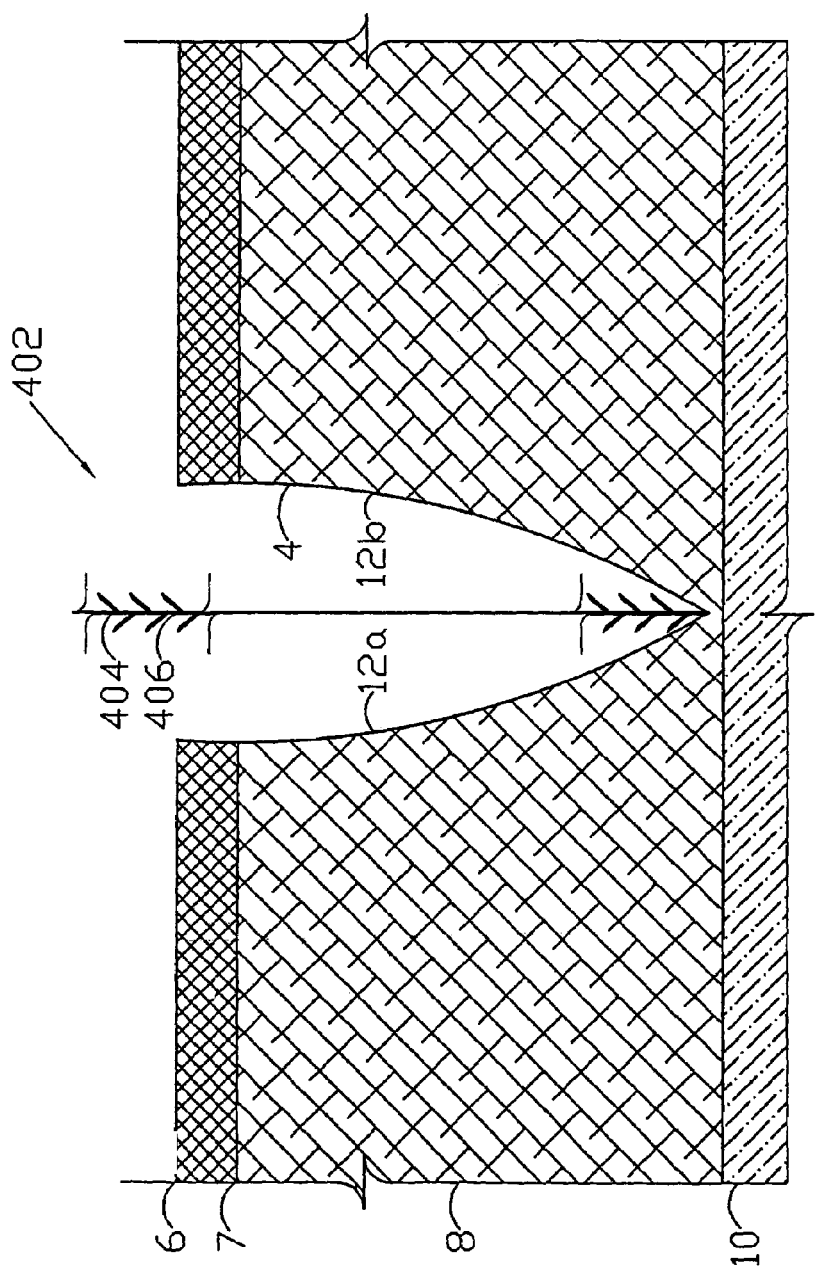

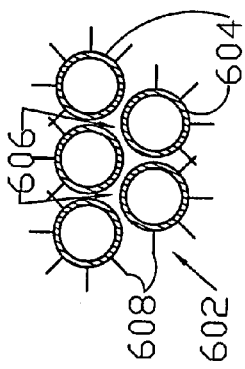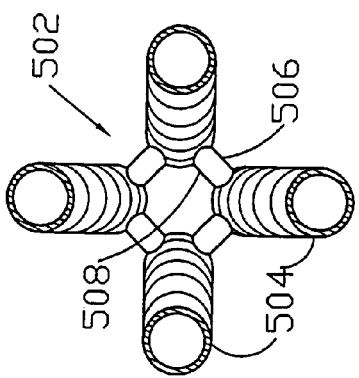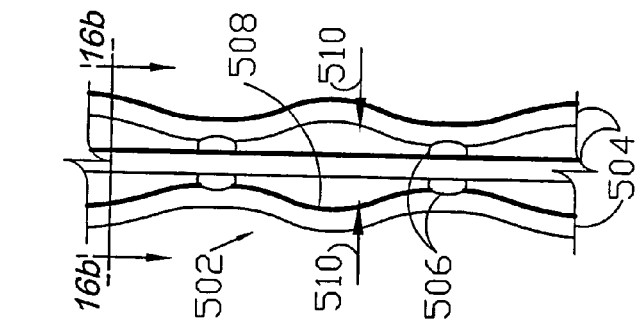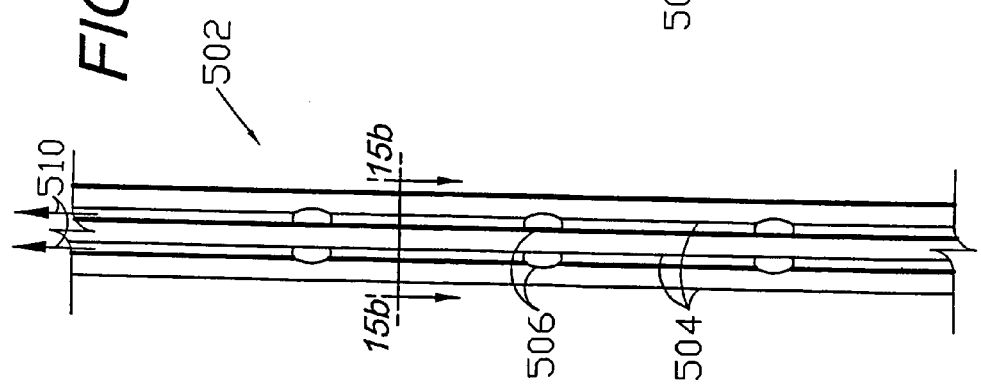

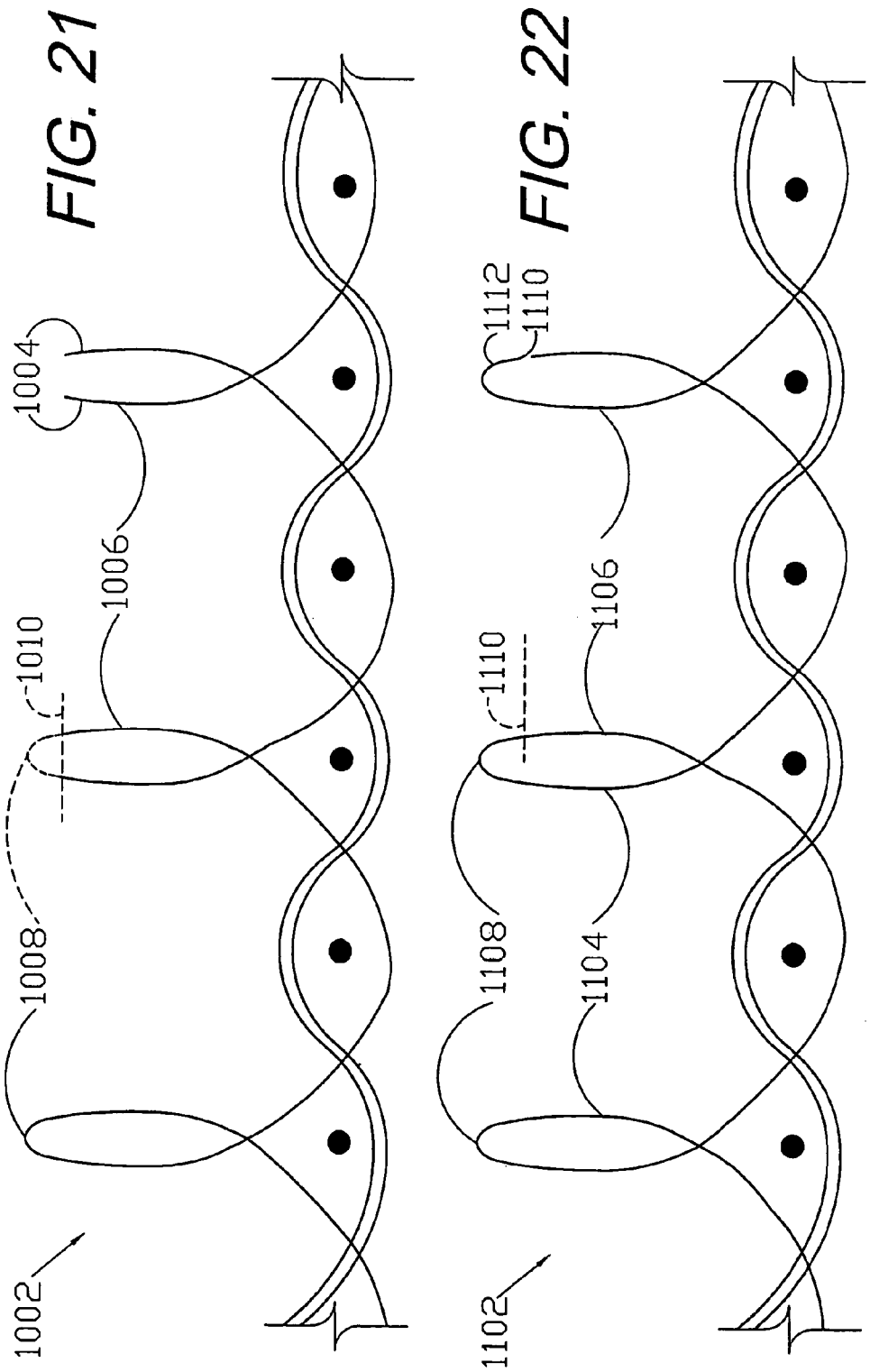

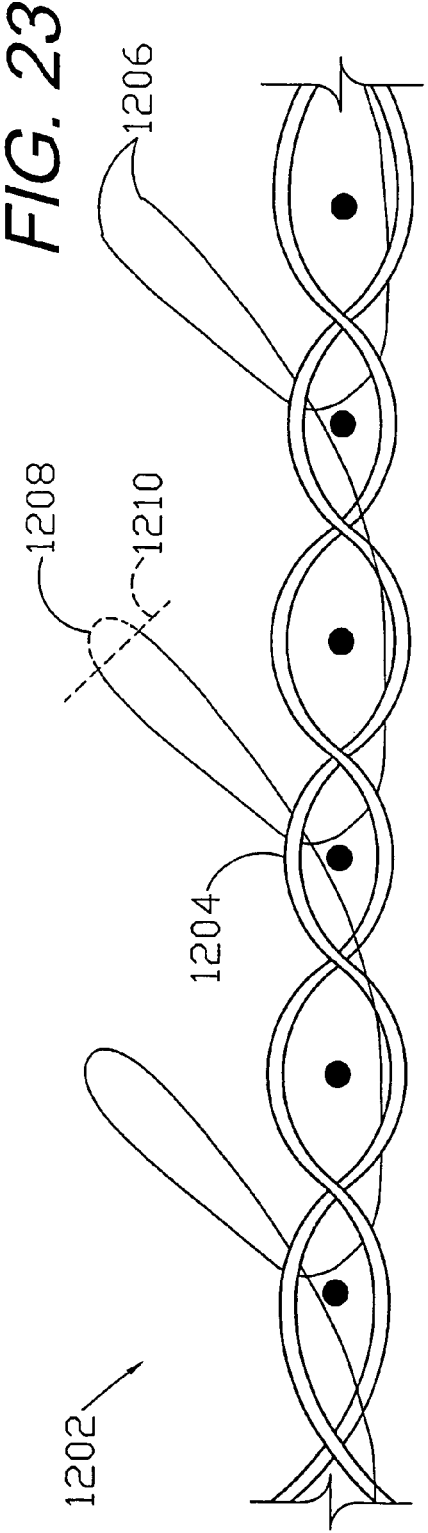
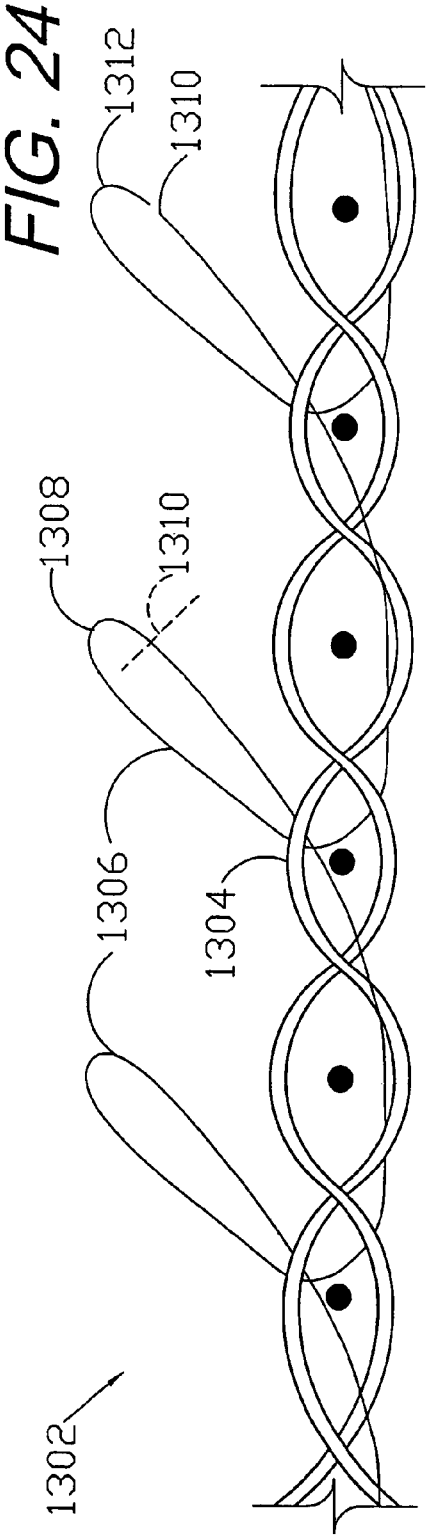

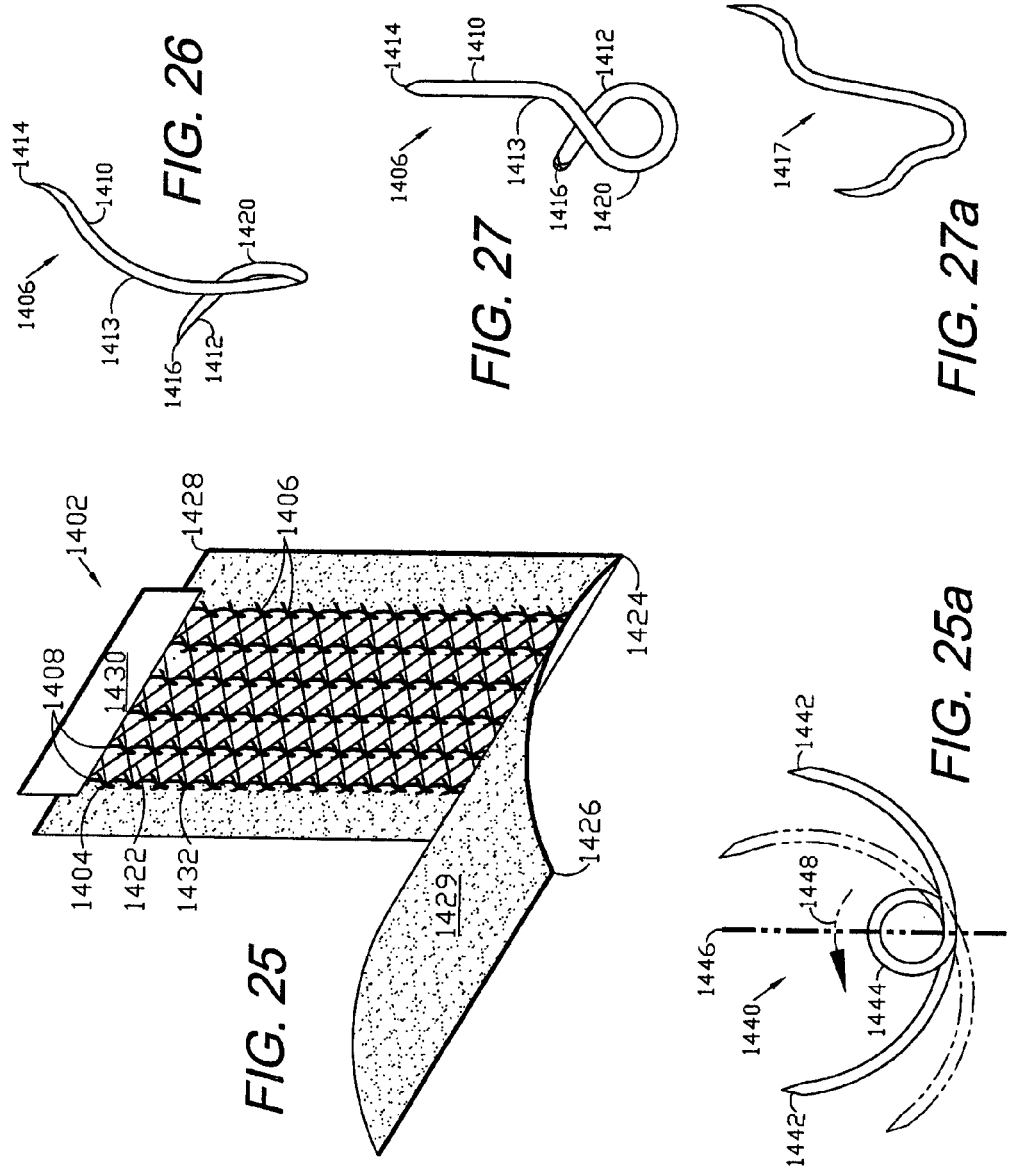

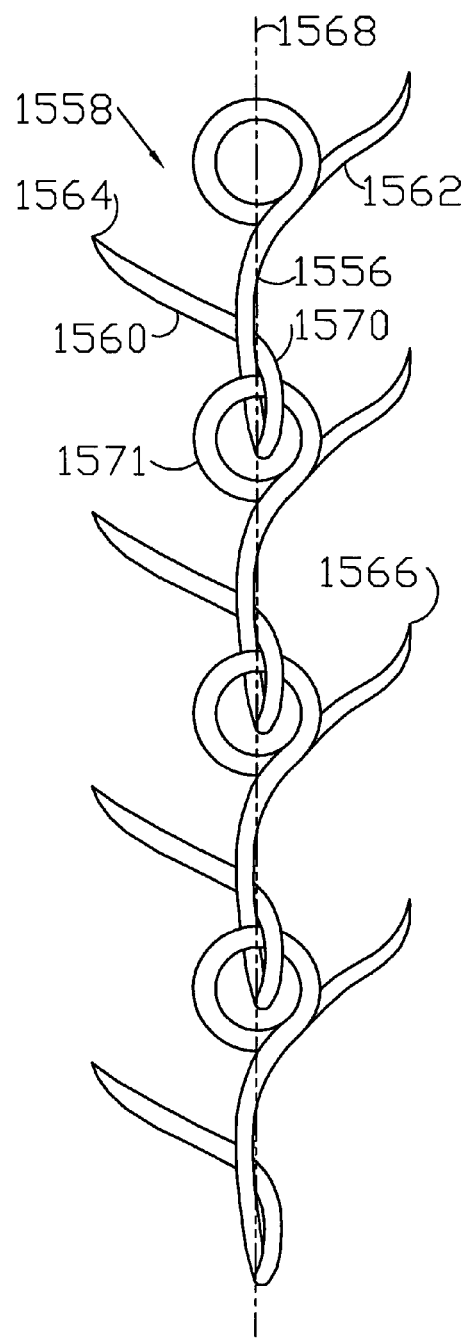
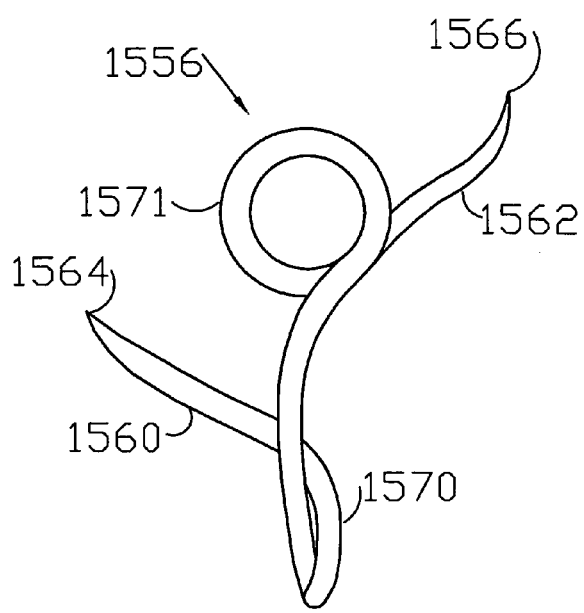
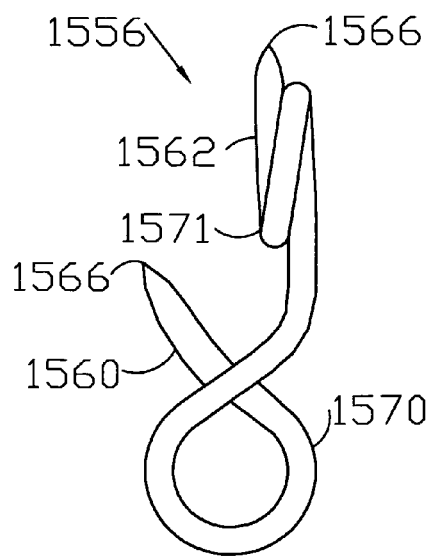
FIG. 31
FIG. 32
FIG. 33

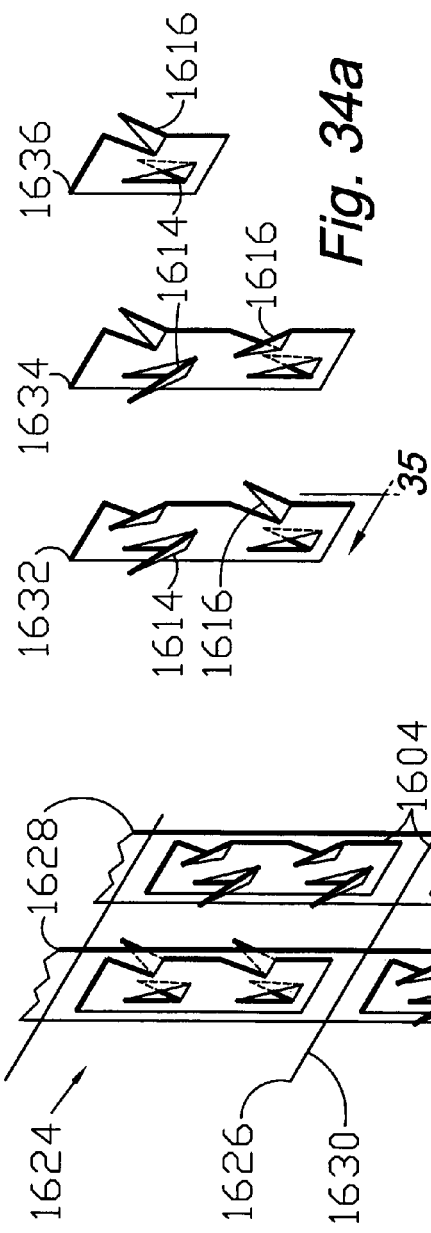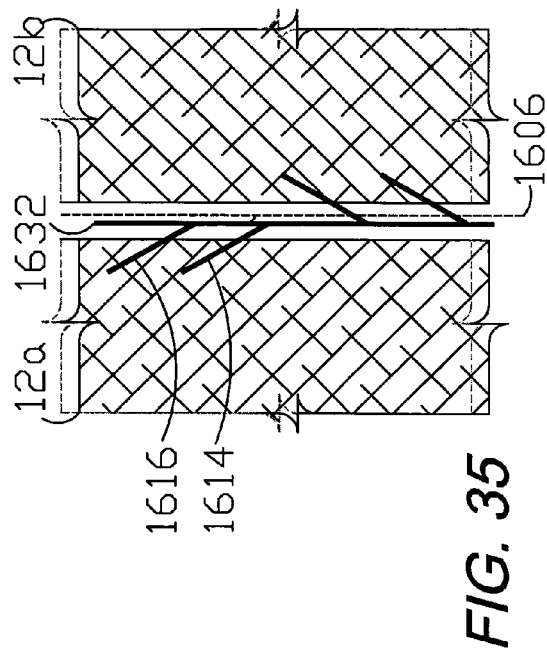

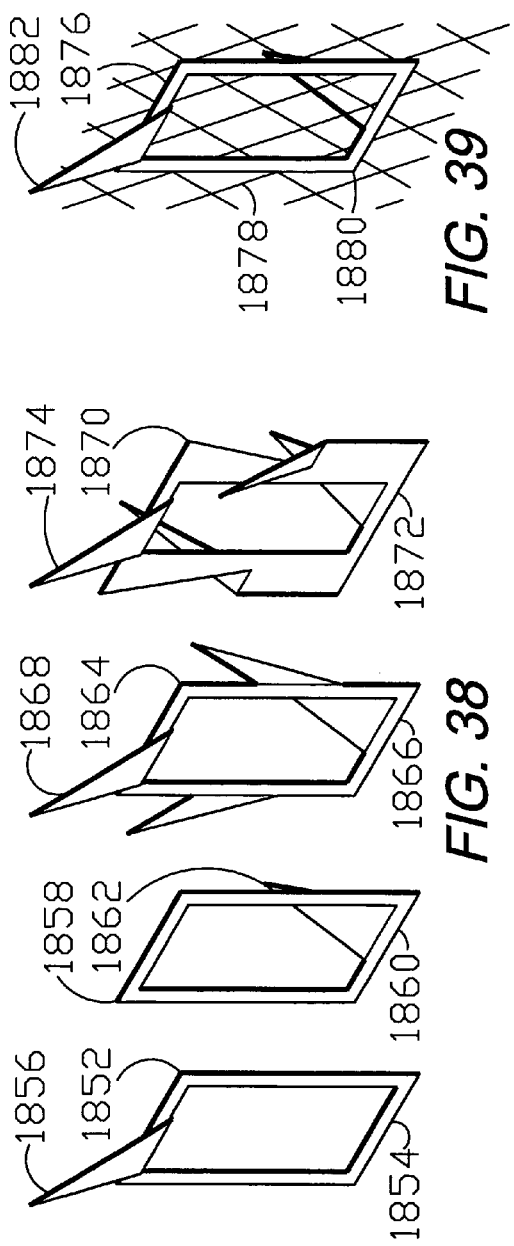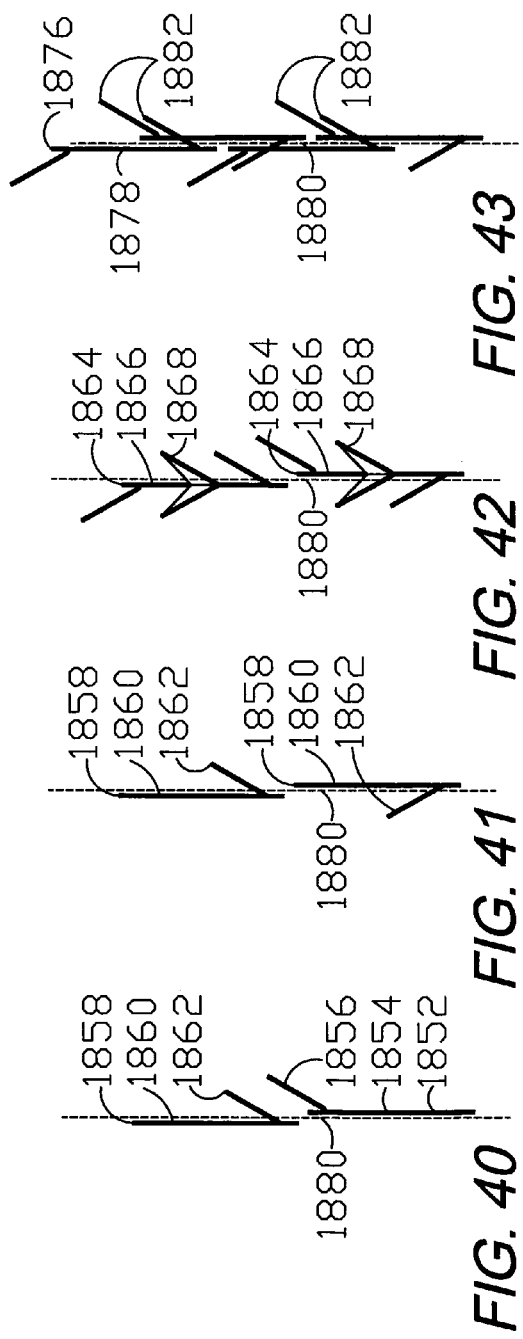

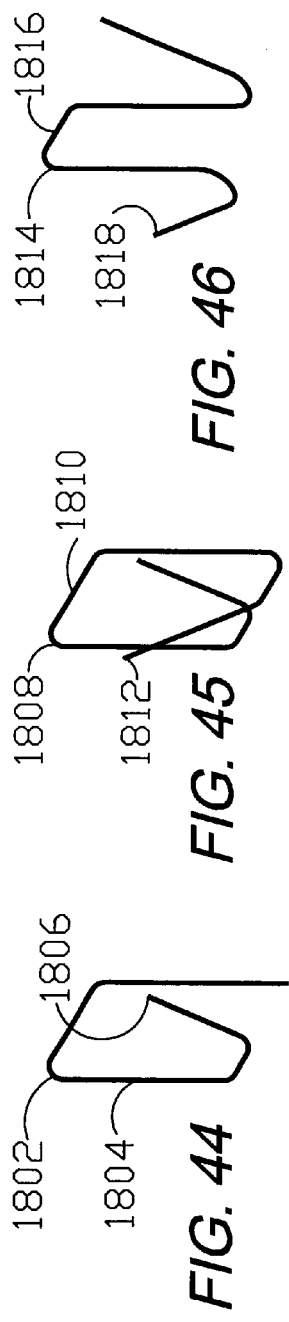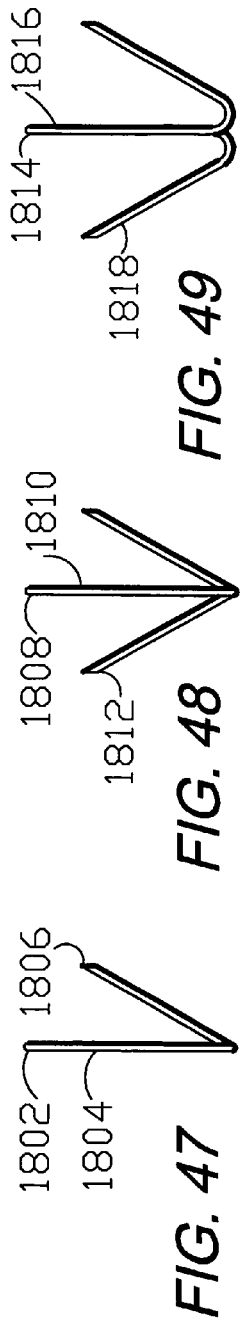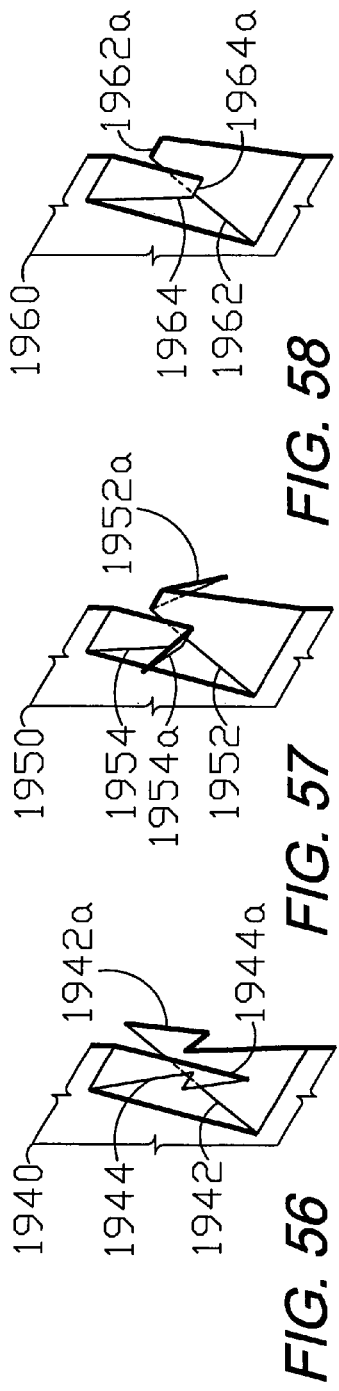

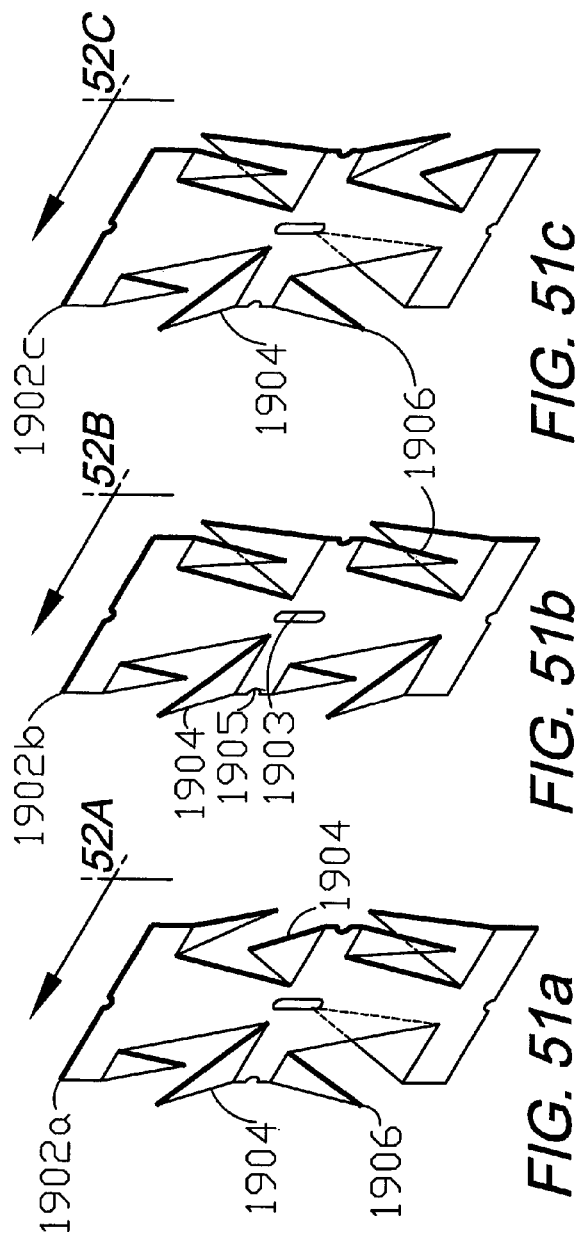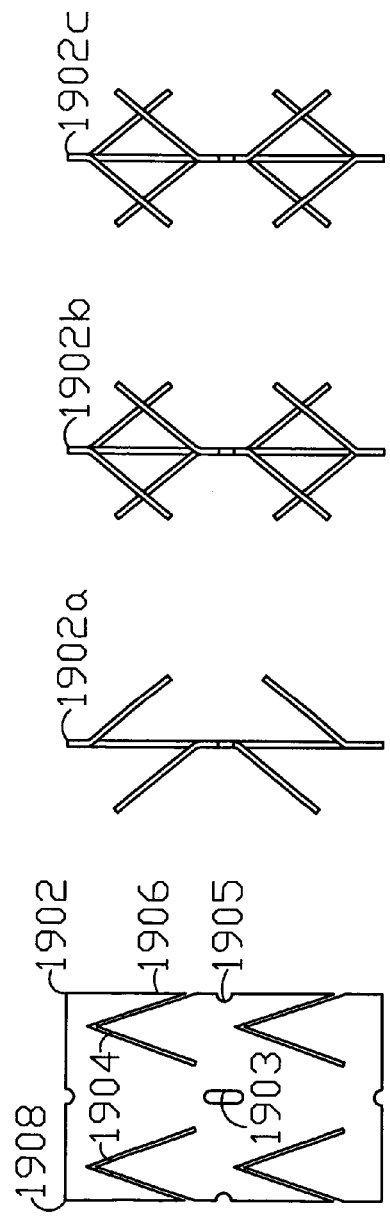

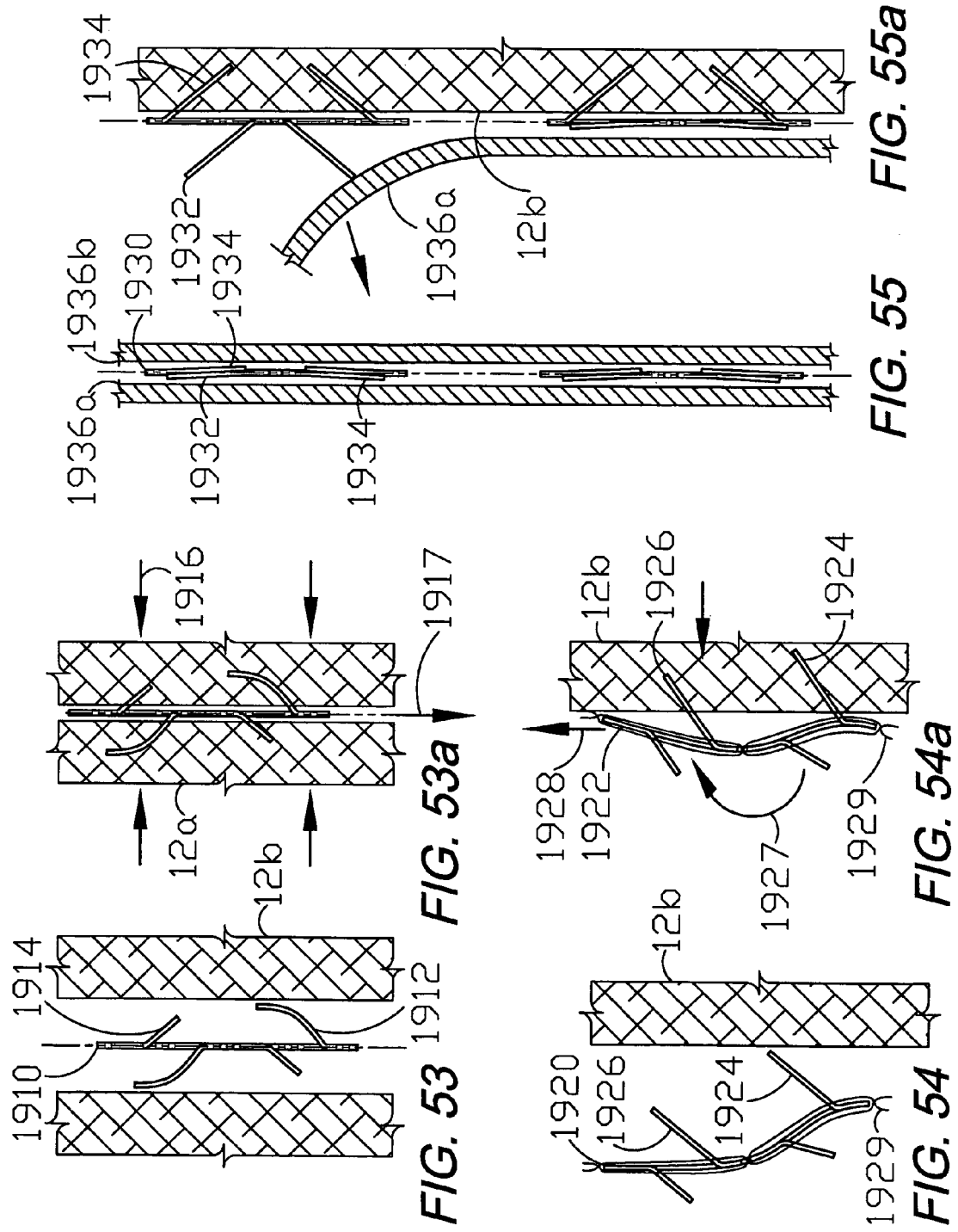

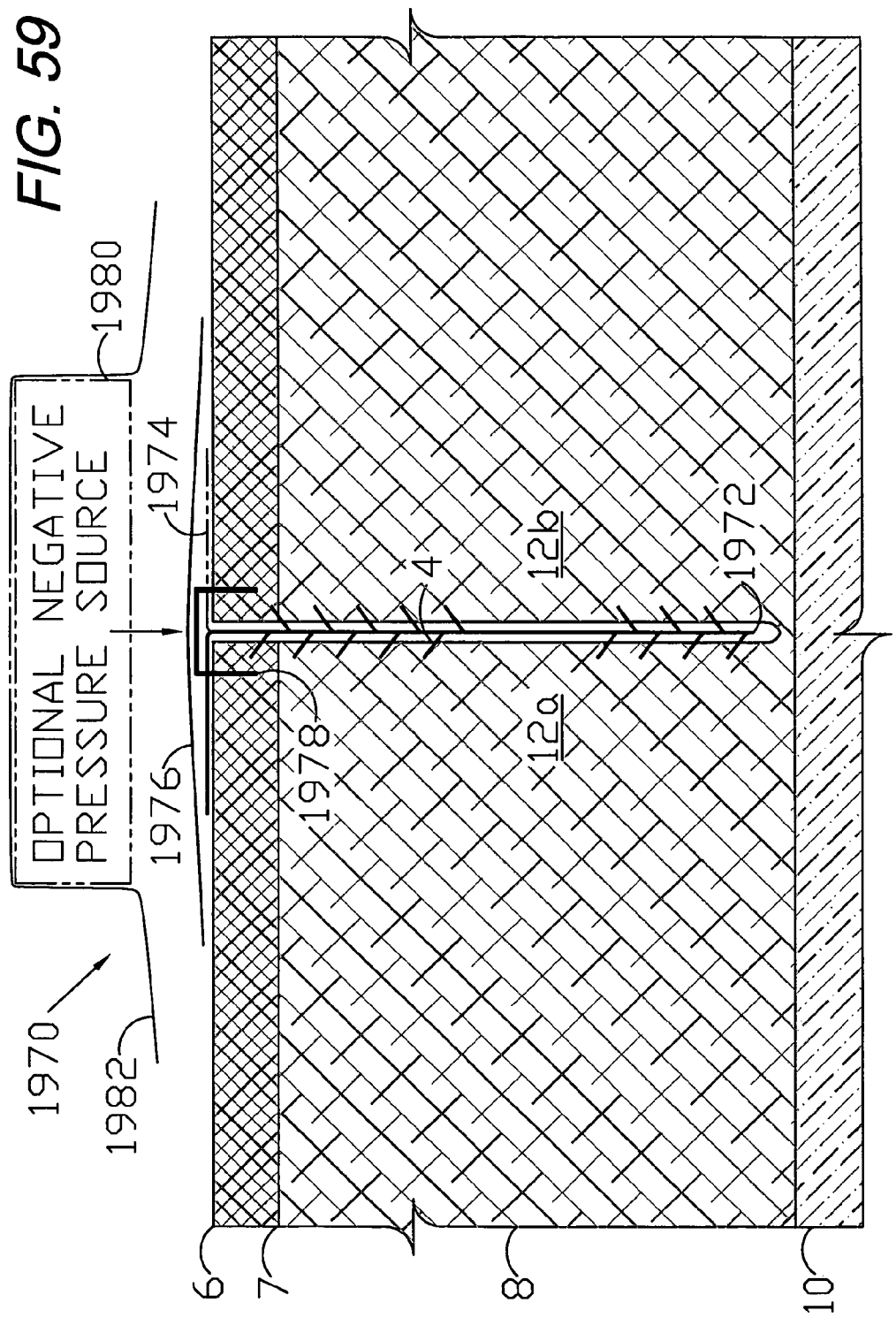

MEDICAL CLOSURE CLIP SYSTEM AND METHOD

CROSS-REFERENCE TO RELATED APPLICATION

This application is a continuation-in-part of U.S. patent application Ser. No. 10/224,852 filed on Aug. 21, 2002 currently pending in the United States Patent Office, and is incorporated herein by reference.

BACKGROUND OF THE INVENTION

1. Field of the Invention

The present invention relates generally to medical (including dental, veterinary, etc.) closure and wound fluid management devices, and in particular to a screen closure member for closing tissue separations, such as incisions and wounds, which closure member is optionally bioabsorbable. The closure member can be assembled with different components chosen for their functional and material compatibility characteristics.

2. Description of the Prior Art

In the medical field, which is broadly defined to include dentistry, veterinary medicine, etc., cutaneous incisions are commonly performed in surgery to provide access to underlying tissue, organs, joints, skeletal structure, etc. Incision and closure techniques are an important part of surgery in general. They tend to occupy surgical teams and other resources for significant portions of many surgical procedures.

Surgeons generally strive to minimize the traumatic and scarring effects of surgery on their patients by both minimizing the incisions, and by employing a variety of closure techniques which tend to reduce postoperative swelling, bleeding, seroma, infection and other undesirable postoperative side effects. For example, the fields of endoscopic-assisted surgery, microscopic surgery, and computer-enhanced instrumentation (e.g., the DaVinci System available from Intuitive Surgical, Inc. of Sunnyvale, Calif.) are generally concerned with minimally invasive surgery ("MIS") procedures and techniques, which have proven to be increasingly popular. Such popularity is at least partly due not only to the minimally-sized scars left by such techniques, but also to the minimal trauma to the fascia and muscle layers and the correspondingly faster recoveries this allows. However, surgeons must balance such considerations with providing adequate access to perform various surgical procedures. A typical surgical procedure involves a cutting or dissecting phase and a closing phase. In recent years, considerable progress has been made in minimizing surgical cutting, dissecting and shaping. Surgical closing techniques involve sutures, clips, staples and adhesives. However, suturing can be time-consuming and tedious. Moreover, the tissue structures to be joined may not be amenable to other closure techniques. MIS often restricts access to the separated tissue structures, thus making it more difficult to approximate and close same.

In contrast to MIS, some surgical procedures, by their nature, must include long incisions. Examples include cutaneous excisional procedures such as "lifts" and reduction procedures, flap procedures for closure of defects, and many bariatric procedures. Suturing in these extensive defects can be time-consuming and tedious.

The "first intention" (primary intention healing) in surgery is to "close" the incision. For load-bearing tissues, such as bone, fascia, and muscle, this requires substantial material, be it suture material, staples, or plates and screws. For the wound to be "closed," the epithelial layer must seal. To accomplish this, the "load bearing" areas of the cutaneous and subcutaneous layers (i.e., the deep dermal elastic layer and the superficial fascia or fibrous layers of the adipose tissue, respectively) must also at least be held in approximation. Important considerations include controlling infection and bleeding, reducing scarring, eliminating the potential of hematoma, seroma, and "dead-space" formation and managing pain. Dead-space problems are more apt to occur in the subcutaneous closure. Relatively shallow incisions can normally be closed with surface-applied closure-techniques, such as sutures, staples, glues, and adhesive tape strips. However, deeper incisions may well require not only skin surface closure, but also time-consuming placement of multiple layers of sutures in the load-bearing planes. Absorbable sutures are commonly used for this purpose and comprise an important class of surgical sutures. Depending on various factors, absorbable sutures typically dissolve over a period of a few days to a few months. Commercially available examples include Monocryl® monofilament absorbable synthetic sutures comprising a poliglecaprone and PDS® (polydrioxanone) and Vicryl® (polyglactin) sutures, all available from Ethicon, Inc., of Somerville, N.J.

Surgical mesh is commonly used to span or reinforce load-bearing planes or defects in them. When coupled with sutures or fasteners, surgical mesh represents another important class of surgical closure devices. Applications include reconstruction, hernia repair, and organ repair. In such procedures, surgical mesh fabric prostheses are inserted into patients through either open surgery or endoscopic (MIS) procedures. Knitted surgical mesh for hernia repair is disclosed in the Agarwal et al. U.S. Pat. No. 6,287,316, which is assigned to Ethicon, Inc. Another Ethicon, Inc. patent, Duncan U.S. Pat. No. 4,548,202, discloses mesh tissue fasteners including various fastening members with spaced-apart legs for passing through tissue portions. Another closure procedure involves the placement of pins or rods through skin edge or bone followed by the placement of an external clamp or fixator device spanning the wound and frequently incorporating a worm-screw apparatus capable of progressive tightening over time to effect closure, stabilization or distraction.

Fluid management represents another important aspect of both open and minimally invasive surgery. Postoperative fluid drainage can be accomplished with various combinations of tubes, sponges, and porous materials adapted for gathering and draining bodily fluids. The prior art includes technologies and methodologies for assisting drainage. For example, the Zamierowski U.S. Pat. Nos. 4,969,880; 5,100,396; 5,261,893; 5,527,293; and U.S. Pat. No. 6,071,267 disclose the use of pressure gradients, i.e., vacuum and positive pressure, to assist with fluid drainage from wounds, including surgical incision sites. Such pressure gradients can be established by applying porous foam material either internally or externally to a wound, covering same with a permeable, semi-permeable, or impervious membrane, and connecting a suction vacuum source thereto. Fluid drawn from the patient is collected for disposal. Such fluid control methodologies have been shown to achieve significant improvements in patient healing. Another aspect of fluid management, postoperative and otherwise, relates to the application of fluids to wound sites for purposes of irrigation, infection control, pain control, growth factor application, etc. Wound drainage devices are also used to achieve fixation and immobility of the tissues, thus aiding healing and closure. This can be accomplished by both internal closed wound drainage and external vacuum devices. Fixation of tissues in apposition can also be achieved by-bolus tie-over dressings (Stent dressings), taping, strapping and (contact) casting.

Heretofore, there has not been available a medical closure screen assembly with the advantages and features of the present invention, including the combination of same with negative pressure wound therapy ("NPWT").

SUMMARY OF THE INVENTION

In the practice of one aspect of the present invention, a medical closure screen device is provided, which includes a mesh screen comprising tubular vertical risers, barbed filaments therebetween and horizontal spacers. Integral or separate sutures can be provided. An optional perimeter member partly surrounds the screen member and can comprise a perimeter tube fluidically coupled with the vertical risers to form a tubing assembly. The tubing assembly cooperates with the vertical risers to extract fluid from the tissue separation in a drain mode and to introduce fluid thereinto in an irrigate mode. In one embodiment of the invention the tubing assembly is fluidically coupled to a vacuum source to facilitate drainage. In another embodiment of the invention, the perimeter tube is passed through the surrounding tissue to secure the screen member in place. Fluid transfer elements, such as sponges, foams, absorbent mesh, microtubular materials and the like, are optionally placed adjacent to and over an extension of the screen for fluid transfer, for example, in conjunction with a vacuum or pump source. Another embodiment of the invention includes a suture connected to the screen and adapted for securing same in a tissue separation.

Alternative embodiment vertical risers are also disclosed, and can provide active fluid transfer utilizing the patient's body dynamics. Yet another alternative embodiment of the present invention utilizes the screen barbs for mechanical fixation in a separation for closure of same. Separation closure, irrigation and drainage methodologies are disclosed utilizing various combinations of closure screens, tubing, sutures, fluid transfer elements and gradient force sources. The closure screen of the present invention uses mechanical and other forces associated with screens and barbed strands for securing separated tissues together and for eliminating or reducing the formation of subcutaneous voids or pockets, which can potentially form hematoma and seroma effects. Further embodiments of the invention include assemblies of clips, which can comprise relatively rigid material, with flexible, elastic or collapsible connecting filaments forming composite material screens.

BRIEF DESCRIPTION OF THE DRAWINGS

FIG. 1 is a side elevational view of a medical closure screen device embodying the present invention.

FIGS. 4a-f show alternative perimeter tube end closures comprising: 4a) subdermal termination; 4b) knotted end; 4c) Leur lock; 4d) transfer element (i.e., sponge); 4e) vacuum source; and 4f) clamped end.

FIGS. 5a-e show a tissue separation closure procedure embodying the method of the present invention.

FIG. 6b is an enlarged, fragmentary, cross-sectional view of the closure screen in a substantially closed tissue separation.

FIGS. 7a-f show a tissue separation closure procedure embodying the method of the present invention and utilizing optional sponge or foam fluid transfer elements and a tubing placement tool.

FIG. 8 is a cross-sectional view of a tissue separation closure utilizing tubing for securing the closure screen with a fluid transfer subassembly connected to an upper edge of the closure screen.

FIG. 9 shows a needle mounting a length of drain tubing and adapted for passing same through tissue.

FIG. 10 is a side elevational view of a closure screen comprising an alternative embodiment of the present invention, with a perimeter suture.

FIGS. 14a-g show a tissue separation closure procedure utilizing the screen-only embodiment of the closure screen.

FIG. 15a is a side elevational view of a modified vertical riser with flexible, multi-tube risers forming a fluid passage.

FIG. 15b is a cross-sectional view thereof, taken generally along line 15b-15b in FIG. 15a.

FIG. 16a is a fragmentary, side elevational view thereof, shown in a compressed configuration.

FIG. 16b is a cross-sectional view thereof, taken generally along line 16b-16b in FIG. 16a.

FIG. 17 is a cross-sectional view of another modified vertical riser construction with risers bundled in a different configuration, with barbs.

FIG. 21 is an enlarged, cross-sectional view of a closure screen comprising an alternative embodiment of the present invention, with barbs formed by cutting off the ends of looped filaments.

FIG. 22 is an enlarged, cross-sectional view of a closure screen comprising an alternative embodiment of the present invention, with barbs forming hooks and constructed by cutting looped filaments.

FIG. 23 is an enlarged, cross-sectional view of a closure screen comprising yet another alternative embodiment of the present invention, with barbs formed by cutting off the ends of looped filaments, which are laid over in a common direction or orientation.

FIG. 24 is an enlarged, cross-sectional view of a closure screen comprising a further alternative embodiment of the present invention, with barbs forming hooks and constructed by cutting looped filaments, which are laid over in a common direction or orientation.

FIG. 25 is a perspective view of a closure screen comprising a further alternative embodiment or aspect of the invention, comprising individual links forming flexible strands.

FIG. 25a is a front elevational view of a link thereof.

FIG. 26 is a side elevational view of an alternative configuration link for the closure screen shown in FIG. 25.

FIG. 27 is a front elevational view thereof.

FIG. 27a is a front elevational view of an alternative configuration link for the closure screen shown in FIG. 25.

FIG. 31 is a side elevational view of a link of a strand of another alternative embodiment closure screen system.

FIG. 32 is a front elevational view thereof.

FIG. 33 is a fragmentary, side elevational view of a strand thereof.

FIG. 34 is a perspective view of another alternative embodiment of the closure screen system, including individual clips mounted on flexible strips.

FIG. 34a shows perspective views of alternative clip configurations.

FIG. 35 is a side elevational view showing a clip approximating opposing tissue portions edges, taken generally along line 35 in FIG. 34a.

FIG. 38 shows perspective views of alternative fastening clip constructions for use in conjunction with the present invention.

FIG. 39 shows another fastening clip construction, which is attached to a mesh.

FIGS. 40-43 are side elevational views of various clip-type closure screens.

FIGS. 44-46 are perspective views of wire fastening clips for use in conjunction with the present invention.

FIGS. 47-49 are side elevational views of the clips shown in FIGS. 44-46 respectively.

FIG. 50 is a plan view of another alternative embodiment clip configuration.

FIGS. 51a-c show alternative prong orientations for the clip configurations shown in FIG. 50.

FIGS. 52a-c are side elevational views of the clips shown in FIGS. 51a-c.

FIG. 53 is a side elevational view of another alternative embodiment clip, with curved prongs.

FIG. 53a is a side elevational view of the clip shown in FIG. 53, shown approximating separated tissue.

FIG. 54 is a side elevational view of another alternative embodiment clip, with a curved body.

FIG. 54a is a side elevational view of the clip shown in FIG. 54, shown anchored in tissue.

FIG. 55 is a side elevational view of another alternative embodiment closure screen, with clip prongs thereof shown folded substantially flat with respect to the clip bodies, and backing material placed on both sides of the closure screen.

FIG. 55a is a side elevational view of the closure screen shown in FIG. 55, with the clip prongs extended and anchored in tissue along one side.

FIGS. 56-58 show alternative embodiment prongs.

FIG. 59 shows an alternative embodiment closure system with external attachments and an optional negative pressure source.

DETAILED DESCRIPTION OF THE PREFERRED EMBODIMENTS

I. Introduction and Environment

Figure 3:
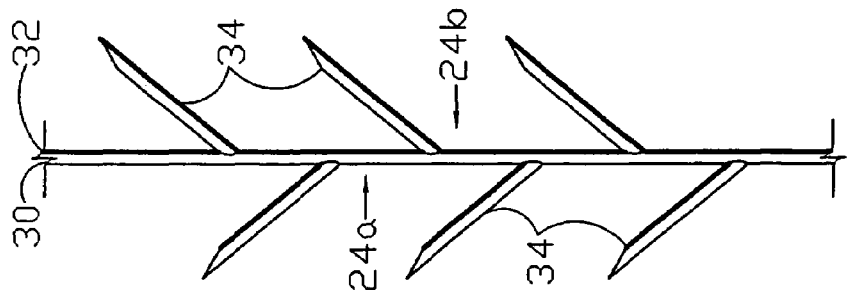
FIG. 3 is an enlarged, fragmentary, side elevational view thereof, taken generally along line 3-3 in FIG. 2, and particularly showing a barbed strand.
Figure 2:
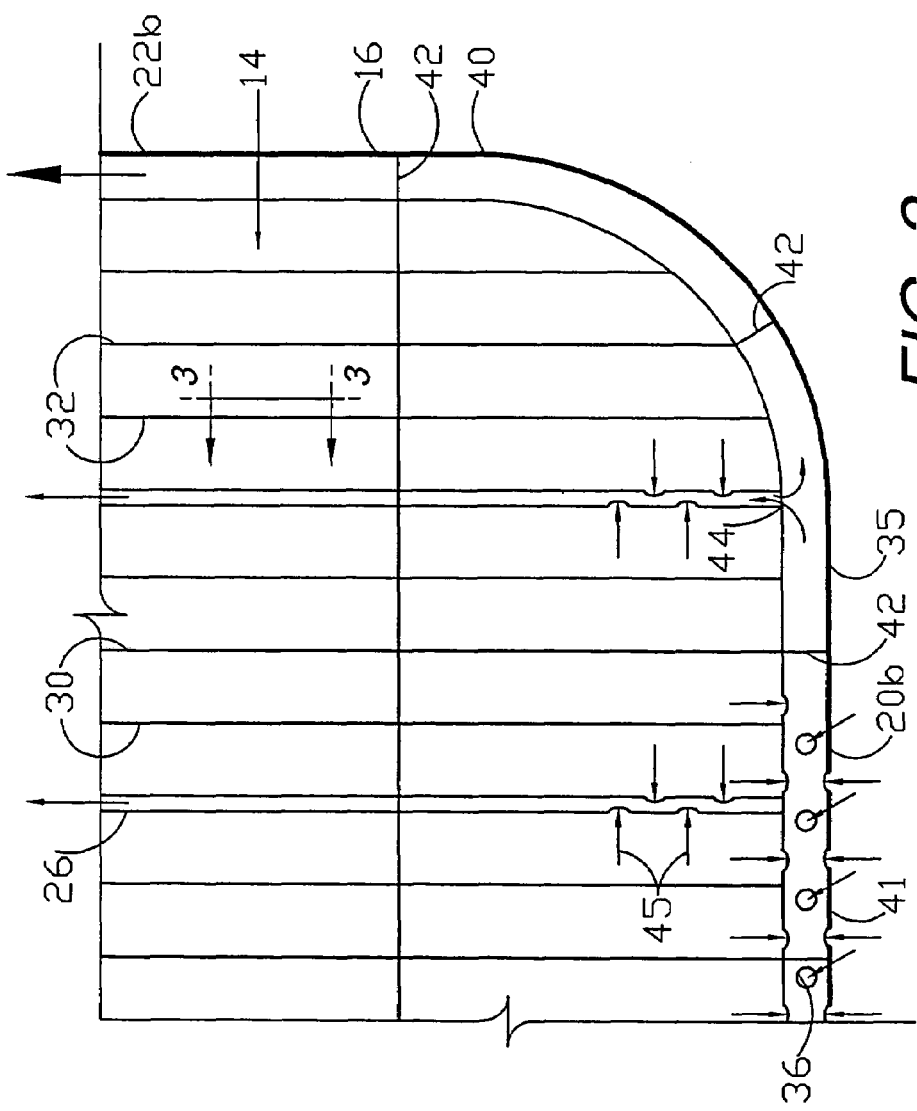
FIG. 2 is an enlarged, fragmentary, side elevational view thereof, taken generally within circle 2 in FIG. 1.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Certain terminology will be used in the following description for convenience in reference only and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the embodiment being described and designated parts thereof. The words "horizontal" and "vertical" generally mean side-to-side and top-to-bottom, respectively. Said terminology will include the words specifically mentioned, derivatives thereof and words of a similar import.

Referring to the drawings in more detail, the reference numeral 2 generally designates a medical closure screen device or system embodying the present invention. Without limitation on the generality of useful applications of the closure screen system 2, the primary application disclosed herein is for assistance with the closing, draining, irrigating and healing of a separation of first and second tissue portions, such as a wound or incision 4. As shown in FIG. 5a, the wound 4 extends from and is open at the dermis 6, through the deep dermal layer 7 and the subcutaneous layer 8, and to approximately the fascia 10. The wound 4 displays edges 12a,b, which correspond to first and second tissue portions. The closure screen device 2 generally comprises a screen 14, a screen perimeter member 16 and an input/output (I/O) subsystem 18.

II. Screen 14

The screen 14 includes upper and lower margins 20a,b; first and second ends 22a,b; and first and second faces 24a,b. The screen 14 generally forms a grid configuration with vertical, hollow, perforated tubular risers 26 cross-connected by horizontal spacer members 28. Multiple barbed strands 30 are positioned between the risers 26. The risers 26, the spacers 28 and the strands 30 are preferably joined at their respective intersections. As shown in FIG. 3, each strand 30 includes a filament 32 with multiple, pointed barbs 34 extending upwardly and outwardly on both sides in staggered, spaced relation. The barbs 34 generally project outwardly from the screen faces 24a,b, for purposes which will be described in more detail hereinafter.

The screen or mesh 14 material can be either dissolvable (absorbable) or non-dissolvable (non-absorbable) and can be chosen from a number of commercially available, biocompatible products, which are commonly used in medical applications for sutures, implantable meshes, and similar medical devices.

Examples of absorbable materials include, but are not limited to: aliphatic polyesters, which include, but are not limited to: homopolymers and copolymers of lactide, epsilon-caprolactone, p-dioxanone, trimethylene carbonate, alkyl derivatives of trimethylene carbonate, delta-hydroxyvalerate, 1,4-dioxepan-2-one, 1,5-dioxepan-2-one, 6,6-dimethyl-1,4-dioxan-2-one and polymer blends thereof. Examples of nonabsorbable materials include, but are not limited to: cotton, linen, silk, polyamides, polyesters, fluoropolymers, polyolefins, polyethylene, metals and combinations thereof.

III. Screen Perimeter Member 16

The optional screen perimeter member 16 can comprise, for example, a flexible, perforated, hollow tube 35 with multiple orifices 36. As shown in FIG. 1, the tube 35 includes first and second legs 38, 40 extending generally along the screen first and second ends 22a,b, and a base leg 41 extending generally along the screen lower margin 20b. The tubing first and second legs 38, 40 terminate in respective first and second ends 38a, 40a. The tube 35 can be secured to the screen 14 by multiple ties 42, which can comprise extensions of the horizontal spacer members 28 and the strands 30. By providing dissolvable ties 42, the tube 35 can be designed for separation from the remainder of the closure screen 2 after a relatively short period of time. For example, the dissolvable material can dissolve into the patient's body after a few days, whereafter the tube 35 can be removed.

Optionally, portions of the tube 35 can be cut away from the screen 14. For example, the screen 14 can be separated along each screen end 22a,b, or it can be separated completely from the tube 35. In this manner the screen 14 and the tube 35 can be configured to accommodate a variety of conditions and tissue separation configurations.

The vertical risers 26 are optionally fluidically coupled to the tube 35 at respective T intersections 44. In this configuration the tube 35 and the vertical risers 26 cooperate to provide a manifold for fluid handling, i.e. either extraction or irrigation, as indicated by the fluid flow arrows 45.

IV. Input/Output (I/O) Subsystem 18

The input/output subsystem 18 is designed for extraction and/or irrigation of the patient's bodily fluids and/or external fluids. As shown in FIG. 1, the input/output subsystem 18 includes first-and second I/O devices 18a,b attached to the tubing first and second leg ends 38a,b, which in this configuration are considered the "port" ends of the tube 35. One or both of the I/O devices 18a,b can comprise a pressure differential source, such as the NPWT device. The V.A.C.® System™, available from Kinetic Concepts, Inc. of San Antonio, Tex. The use of such units for wound treatment and fluid management is disclosed in the Zamierowski U.S. Pat. Nos. 4,969,880; 5,100,396; 5,261,893; 5,527,293; and U.S. Pat. No. 6,071,267, which are incorporated herein by reference.

Alternatively, the tubing port ends 38a,b can be connected to various other sources of pressure differential and various drainage and irrigation devices. For example, they can be cut short below the dermis 6 and left within the separation 4 for sealing by the adjacent tissue portions 12a,b. FIG. 4a shows a truncated tubing end 38b. The tubing ends 38a/40a can be knotted (as shown at 48 in FIG. 4b), clipped, tied (e.g., with a suture) or otherwise closed off either above or below the dermis 6. FIG. 4c shows a Leur lock coupling 46 mounted on a tubing end 38a/40a. Still further, a transfer element comprising a piece of foam or sponge 50 can be coupled to the tube 35 at an end 38a/40a (FIG. 4d). Examples of such foam and sponge materials and configurations are discussed in the Zamierowski U.S. patents identified above. A pressure differential source, such as a vacuum source 51, can be connected to a tube end 38a/40a and to a fluid receptacle 66, as shown in FIG. 4e. A clamp 62 is shown in FIG. 4f and closes the tube end 38a/40a. The clamp 62 can be chosen from among several suitable clamps, which are commonly used for medical applications.

Either tube end 38a/40a can function as either an inlet port or an outlet port with respect to the system 2. For example, suction can be applied for pulling fluid from the patient through the system 2 through either tube end 38a/40a. Still further, fluid can be pulled in both directions through the system 2 by alternately or jointly applying suction to the tube ends 38a/40a. For example, suction can be simultaneously applied to both tube ends 38a/40a.

V. Operation and Closure Method

Figure 5C:
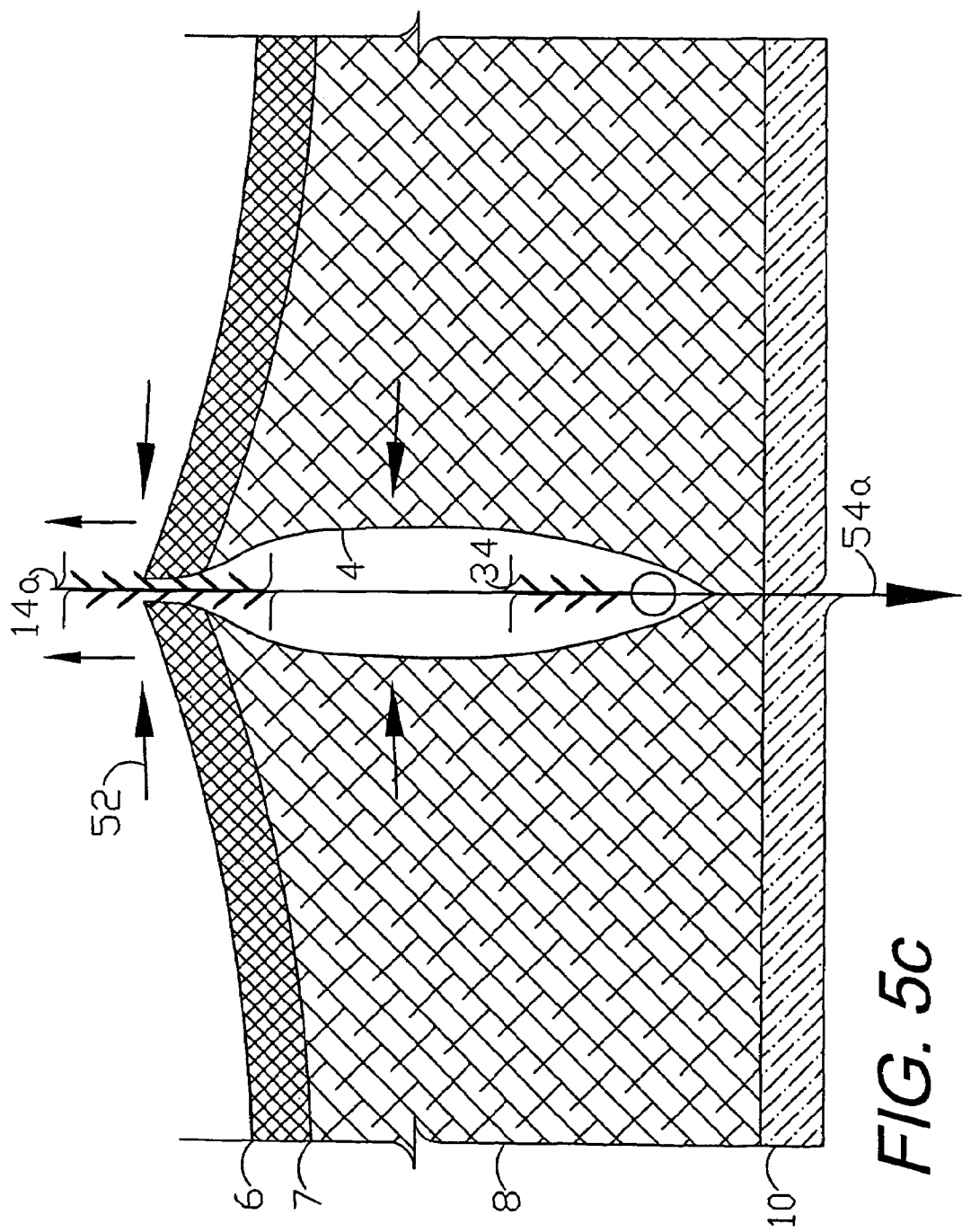
Figure 5D:
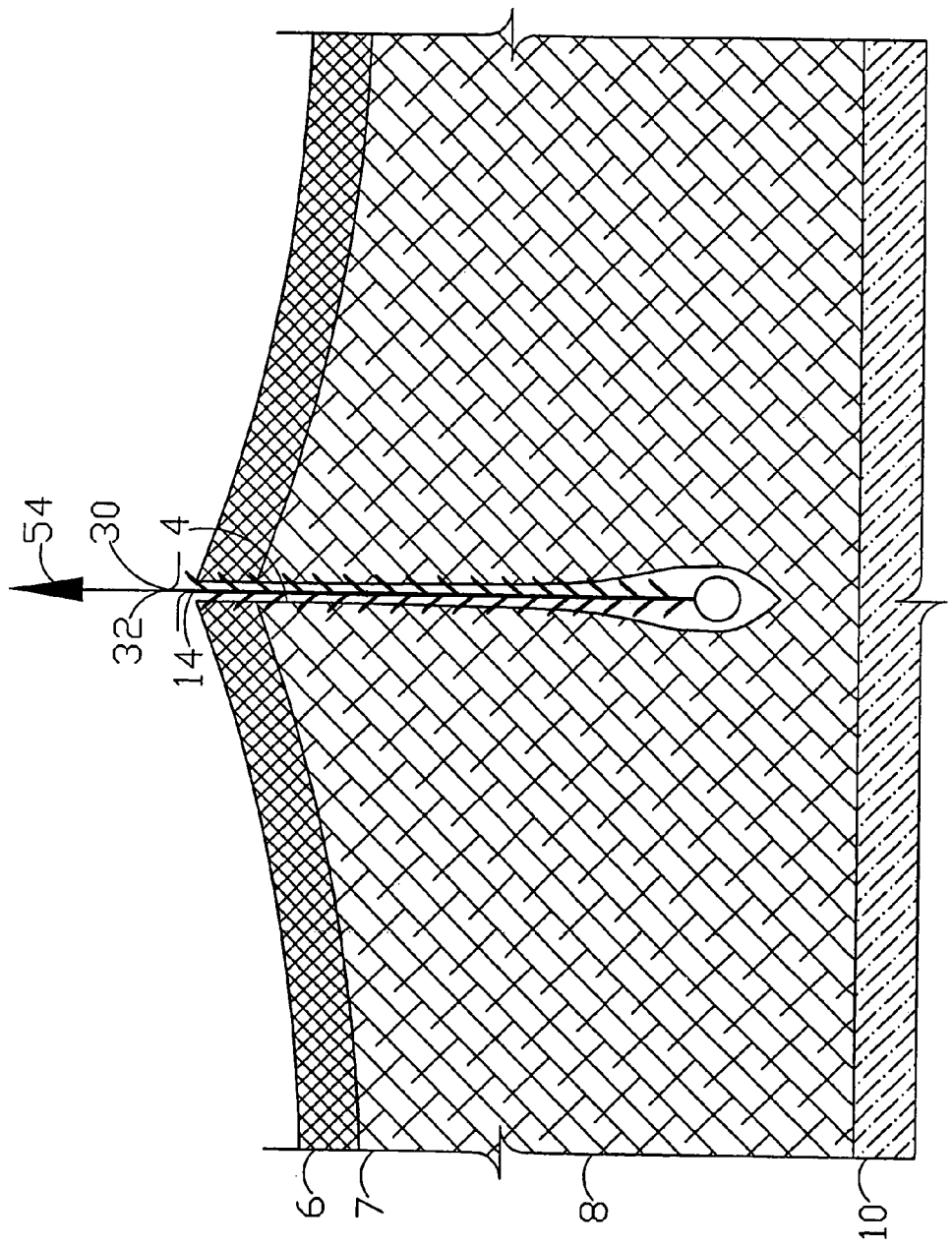

FIGS. 5a-e show an installation methodology utilizing the system 2 of the present invention. In FIG. 5a, the closure screen 2 is placed in the separation 4 with the tubing base 41 located at the bottom of the separation (e.g., wound or incision) 4 and in proximity to the fascia layer 10. As shown, the tissue portions or wound/incision edges 12a,b are spaced apart. The screen upper margin 20a can protrude outwardly from the dermis 6. FIG. 5b shows the tissue separation edges 12 being pushed together as indicated by the force arrows 52. FIG. 5c shows the separation edges 12 engaged at the dermis 6, and spaced apart somewhat within the subcutaneous layer 8. The edges 12 can be pushed together as indicated by the force arrows 52. Moreover, the screen 2 can be held or positioned inwardly in order to advance the barbs 34 in the separation edges 12, as indicated by the inward or downward force arrows 54a. FIG. 5d shows the separation edges 12a,b substantially closed on the screen 2. Tugging on the screen 14 in the general direction of the outward force arrow 54b sets the mesh barbs 34.

FIG. 5e shows the separation 4 closed on the closure screen 2, with the tubing 35 removed from the screen 14. The tubing 35 can be removed either pre-installation by cutting the ties 42, or post-installation by allowing the ties 42 to dissolve, whereafter the unsecured tubing 35 can be extracted.

Figure 6A:
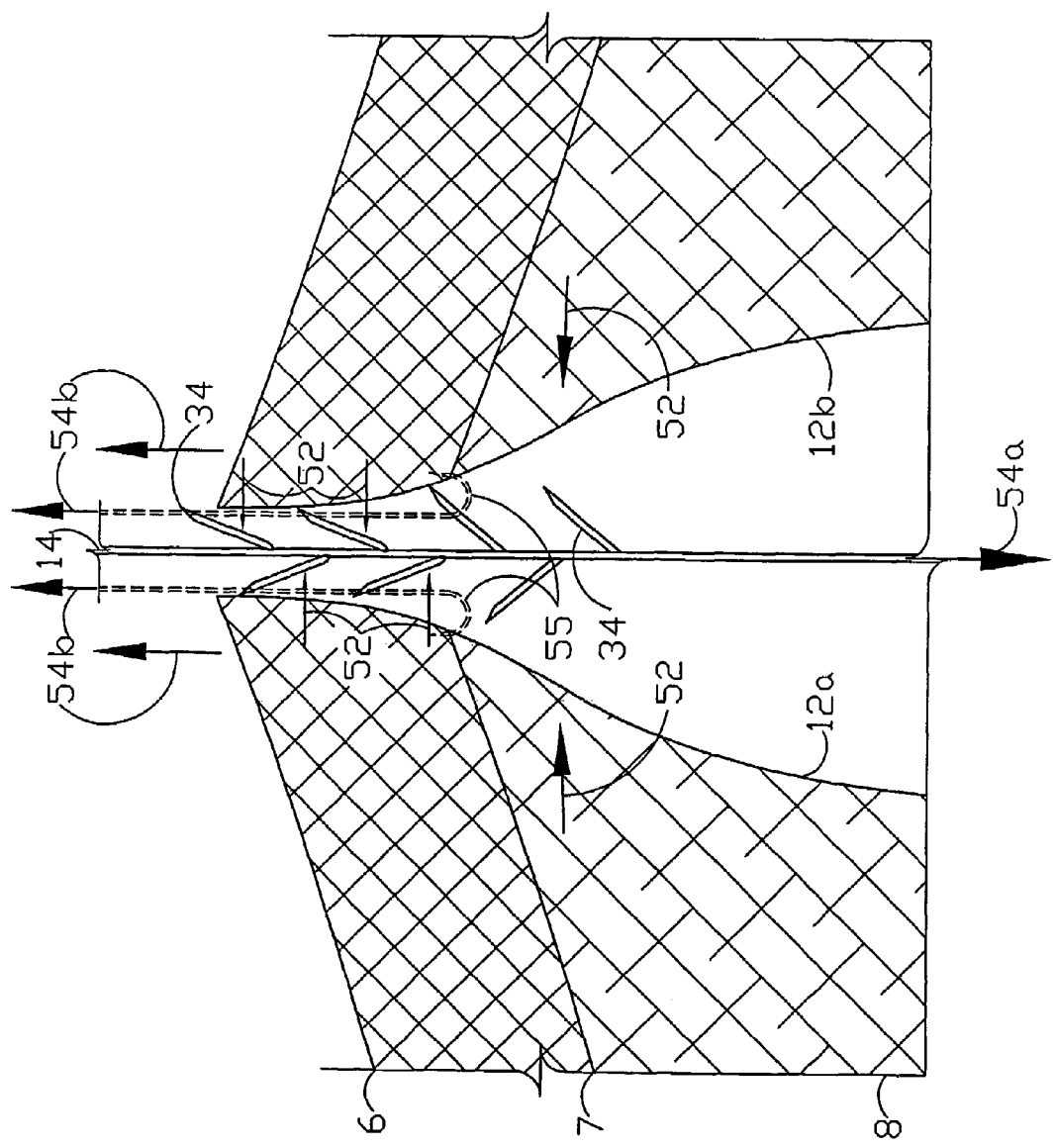
FIG. 6a is an enlarged, fragmentary, cross-sectional view of the closure screen in a tissue separation, with skin hooks shown in hidden lines for positioning the separated tissue portions along the closure screen.

FIG. 6a shows the barbs 34 compressed by engagement with the separation edges 12a,b. As shown, the separation edges 12 can be manually closed by pressing along the horizontal force arrows 52. The barbs 34 allow the separation edges 12a,b to slide upwardly or outwardly along the screen 14. This process can be repeated until the separation 4 is closed, as shown in FIG. 6b. Any protruding length of the screen 14 can be cut close to the dermis 6. In the final configuration (FIGS. 5e and 6b), the barbs 34 are embedded in the tissue adjacent to the separation edges 12a,b and thus secure the separation 4 in a closed position. The fluid conducting properties of the screen 14 facilitate extracting fluid. An outward or upward force arrow 54b indicates a force direction whereby the screen barbs 34 are set in the adjoining tissue. It will be appreciated that the screen 14 can be securely set in place with the barbs 34, yet the separation edges 12a,b will remain capable of sliding up on the screen 14 by disengaging the barbs 34 with lateral forces, as shown in FIG. 6a. Skin hooks 55 can be used for engaging the tissue portions 12a,b and tugging same outwardly as shown in FIG. 6a. The skin hooks 55 can facilitate positioning and repositioning the screen 14.

VI. Alternative Embodiment Closure Screen Systems and Methodologies

Figure 7A:
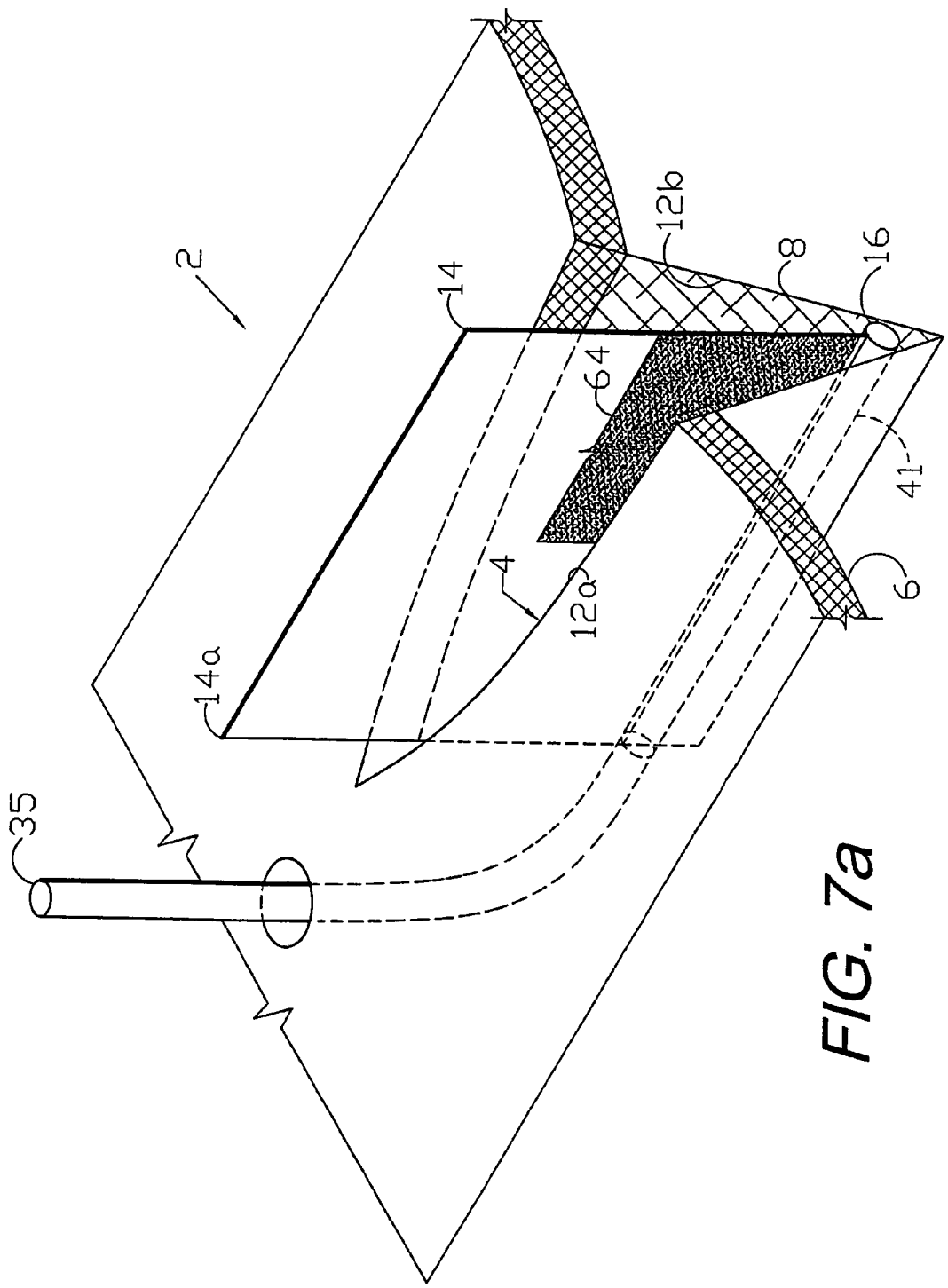
Figure 7B:
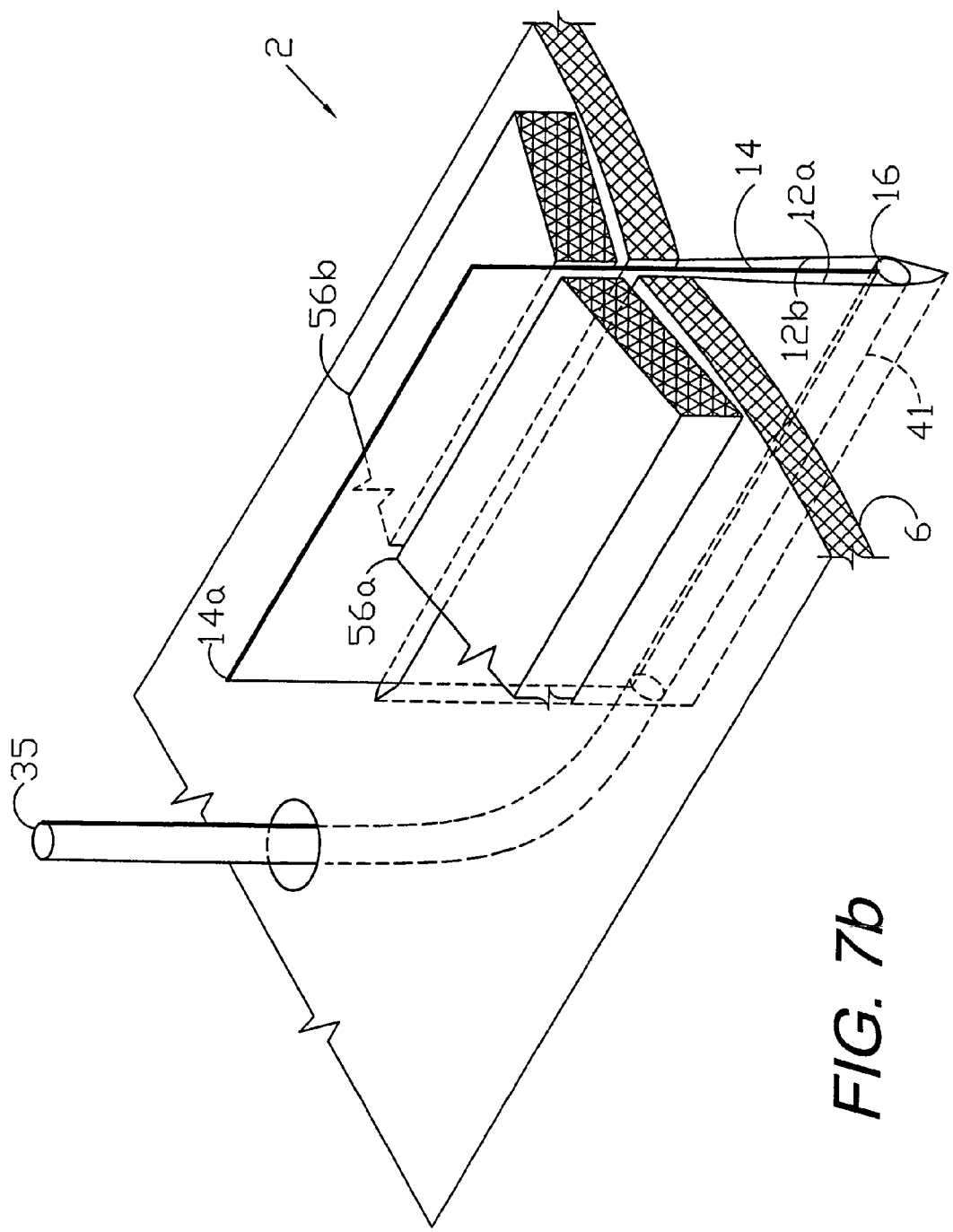

FIGS. 7a-f show an alternative procedure for mounting the closure screen 2 in a wound drainage application utilizing pressure differential. As shown in FIG. 7a, the tubing 35 can pass through the tissue adjacent to the wound 4 and exit the dermis 6 for termination of the tubing end 38a/40a as described above. An optional layer of a suitable, biocompatible adhesive 64 is shown applied to the closure screen first face 24a for securing same to the first wound edge 12a. FIG. 7b shows the screen 14 extending upwardly from the dermis 6 with the wound edges 12a,b brought together in a manner similar to that described above.

Figure 7C:
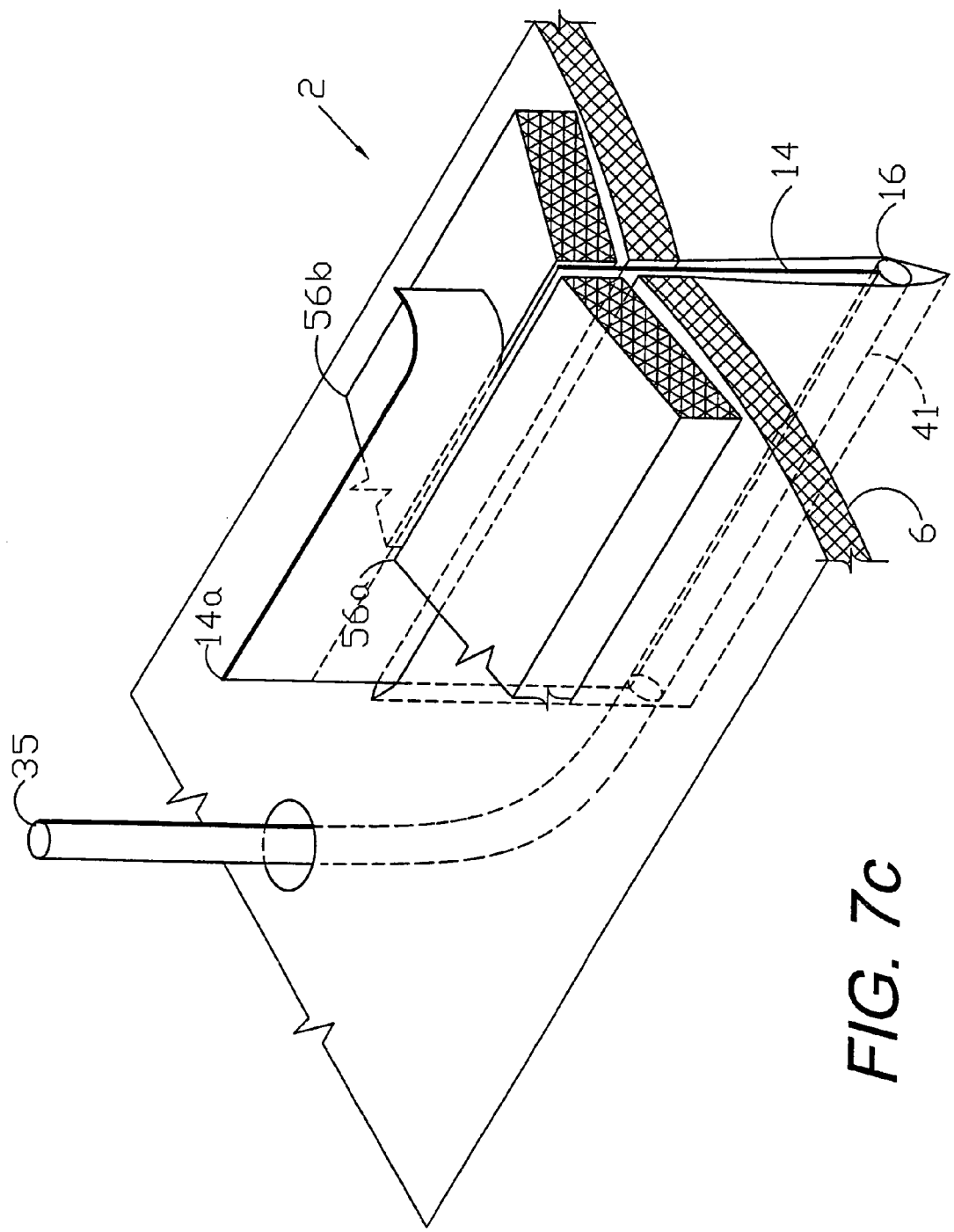
Figure 7D:
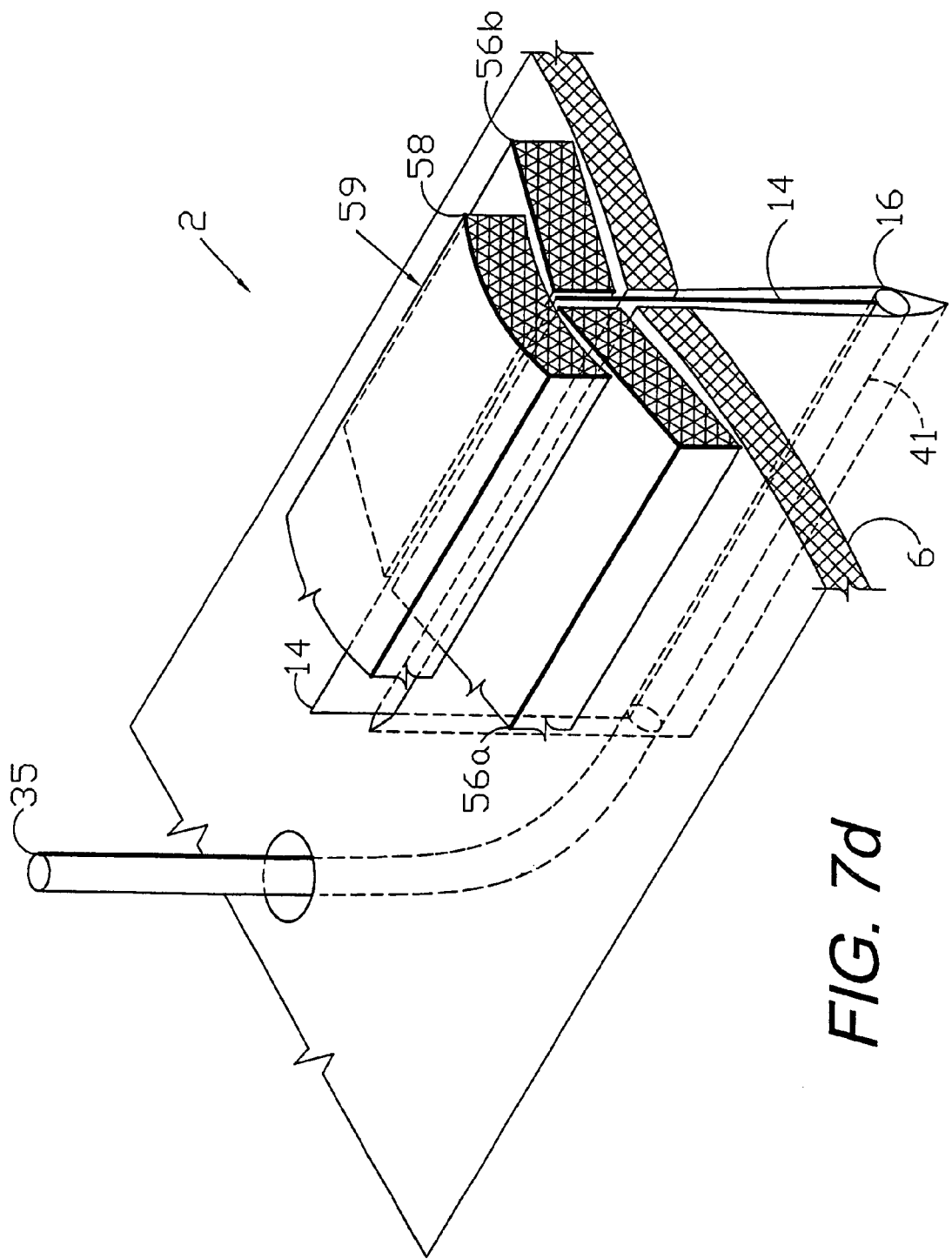

The input/output subsystem 18 includes a pair of optional fluid transfer elements comprising foam or sponge members 56a,b placed on the dermis 6 on either side of a protruding portion 14a of the screen 14. The screen 14 is then cut to a level generally flush with the upper surfaces of the sponges 56a,b, as shown in FIG. 7c. An optional sponge bridge 58 is placed over the sponge members 56a,b (FIG. 7d). Examples of suitable transfer element materials are discussed in the Zamierowski patents noted above and include open-cell, porous foam materials (e. g., polyurethane ester (PUE)) chosen for their hydrophobic properties and passage of liquids. Polyvinyl acetate (PVA) material can be used for its hydrophilic properties. The transfer element subassembly 59 formed by the sponge members 56a,b and 58 can be connected to a vacuum source, a fluid irrigation source, etc. Moreover, it can be connected to additional fluid transfer elements and covered with various flexible membranes and drapes, which can be semi-permeable or impervious, as indicated for the closure and treatment of particular separations and wounds.

FIG. 7e shows a tubing placement tool 120 with a handle 122, a shaft 124 and a hook 126 terminating at a pointed or rounded, bullet-shaped tip 128. FIG. 7f shows the tool 120 passing tubing 35 through tissue in the subcutaneous layer 8 and into proximity with the dermis 6. The tip 128 is received in a blind end 134 of the tubing 35 through a notch 136 formed therein. The thrust of the tool 120 causes tenting of the dermis 6, as shown at 138, whereat the dermis 6 can be opened with a scalpel 140 and the tubing 35 can exit the patient for suitable termination arrangements, such as those shown in FIGS. 4a-f above.

FIG. 8 shows a modified embodiment closure system 202 with a pair of screens 14 positioned generally end-to-end in a separation 204. A transfer element subassembly 59 is placed over the separation 204 and a membrane drape 205 is placed thereover. The tube 35 is passed through tissue on either side of the separation 204 (e.g., using the procedure and the tubing placement tool 120 described above) and exits the dermis 6 on either side of the transfer element subassembly 59. The tube 35 lengths are knotted at 206. The tube 35 lengths thus function as sutures or retainers for securing the closure system 202 in the separation 204. The tube ends 38a or 40a can be utilized for this purpose, thus leaving the other tubing ends available for fluid communication with one or more of the input/output subsystems 18 described above.

The tube 35 can be secured by suitable fasteners, such as clips and the like, located above the dermis 6. Moreover, the screens 14 can be overlapped, abutted, spaced slightly and otherwise configured and positioned as necessary for particular tissue separations. Still further, the screens 14 are adapted to be trimmed as necessary.

FIG. 9 shows a modified embodiment tubing/suture subassembly 220 with a Trocar instrument 222 including a sharpened, distal end 224 and a proximate end 226 with multiple, annular ridges 226a. A length of flexible tubing 228 combines the functions of screen perimeter member and suture. The flexible tubing 228 terminates at an end 228a adapted for releasably mounting on the needle proximate end 226, whereat it is retained in place by the ridges 226a. The tubing 228 is optionally connected to the screen 14 as described above and can include perforations 228b for fluid drainage and/or irrigation in conjunction with input/output subsystems 18, also as described above. The tubing/suture subassembly 220 is adapted for securing the screen 14 in place and for closing the separation 4 by passing the tubing 228 through adjacent tissue. The tubing/suture subassembly 220 and the screen 14 can be prepackaged and presterilized for closing and treating separations, which can include wounds and incisions.

Figure 11B:
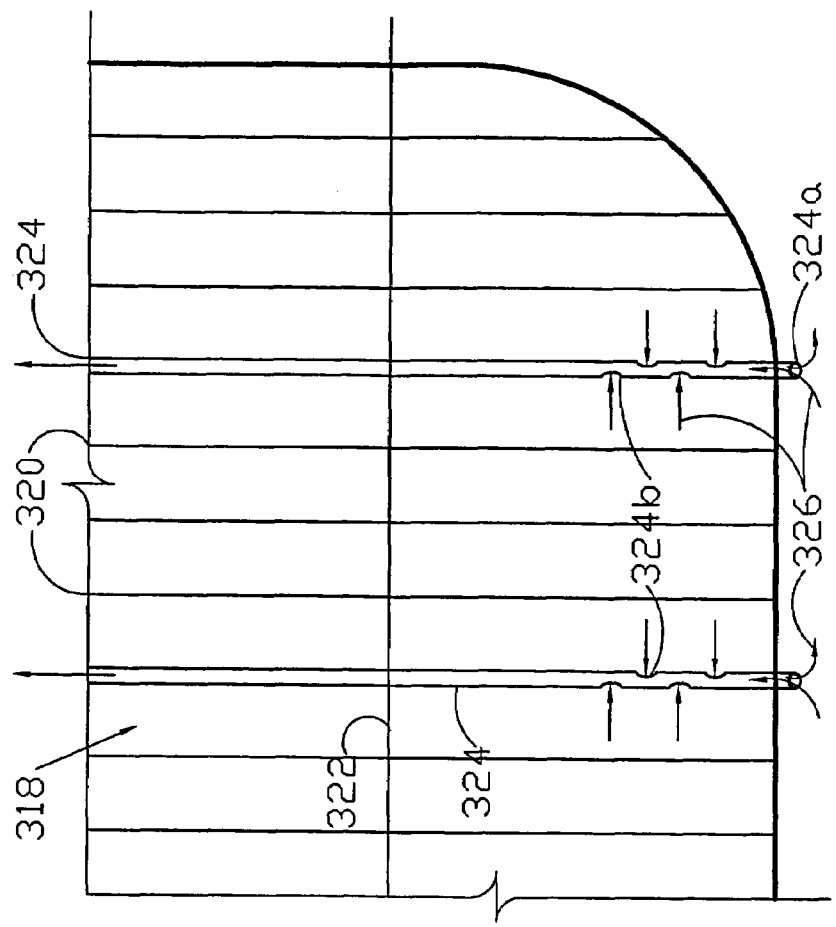
FIG. 11b is an enlarged, fragmentary, side elevational view thereof, showing modified vertical risers.
Figure 11A:
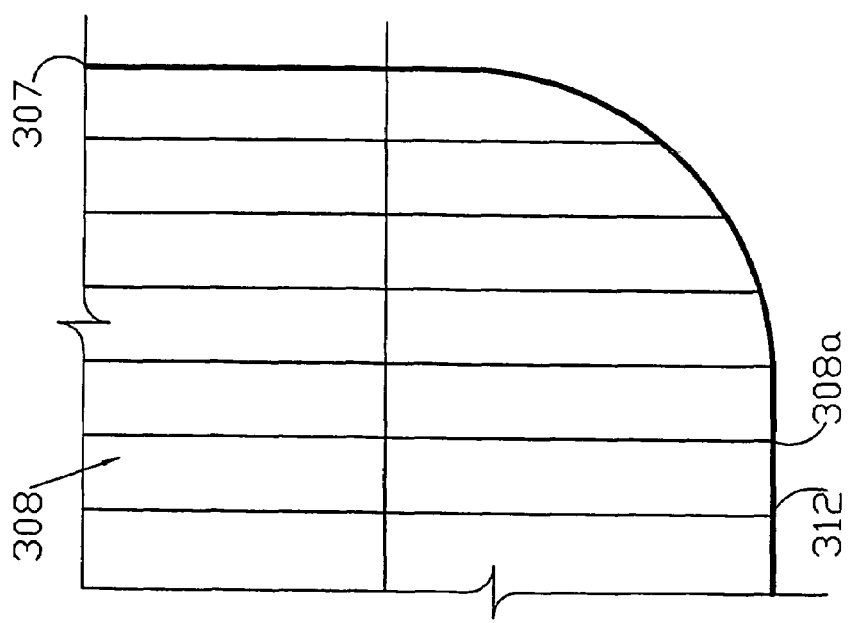
FIG. 11a is an enlarged, fragmentary, side elevational view thereof, taken generally within circle 11a in FIG. 10.

FIGS. 10, 11a and 11b show modified embodiment closure screen systems 302 with first and second suture subassemblies 304, 306 comprising the screen perimeter member. The suture subassemblies 304, 306 include respective curved needles 304a, 306a which are swaged or adhesively connected to opposite ends 304b, 306b of a common length of suture thread 307. The suture thread 307 can be absorbable or nonabsorbable. As shown in FIG. 10, the screen closure system 302 can be preassembled with the suture thread length 307 releasably secured to the perimeter 308a of a screen 308. Prior to installation of the screen 308, the suture 307 can be disconnected or severed therefrom, either partly or completely. For example, the suture 307 can be separated along the screen ends 310a, 310b respectively, thereby leaving the suture thread lengths secured only along a screen lower margin 312.

In operation, the suture subassemblies 304, 306 facilitate installation of the suture/screen closure system 302, thereby providing a preassembled device which incorporates the necessary components for securing same in a separation 4. For example, the screen 308 can be secured at the bottom alone by passing the suture subassemblies 304, 306 through tissue portions located at the bottom of the separation 4. Alternatively, the suture subassemblies 304, 306 can be passed through the adjacent tissue and exit the surface of the dermis 6, whereby the suture subassemblies 304, 306 can be used for closing the separation 4 at the dermis 6. Barbed strands 320 can interact with the tissue portions 12a,b as described above, whereby the screen 308 provides a relatively secure mechanical connection between the separated tissue portions 12a,b. The suture subassemblies 304, 306 can be utilized for various purposes in the separation 4, including attachment and tacking of the dermis 6, the deep dermal layer 7, the subcutaneous layer 8 and the fascia 10. Still further, all or part of the suture subassemblies 304, 306 can be removed, and additional suture subassemblies can be mounted on or sutured to the screen 308.

FIG. 11a shows the screen 308 attached to the suture thread 307. FIG. 11b shows an alternative construction screen 318 with hollow tubular vertical risers 324 located between adjacent, respective vertical strands 320, all connected by the spacers 322 and adapted for communicating fluid with the separation 4 through the open riser ends 324a and the perforations 324b, as indicated by the fluid flow arrows 326. All or part of the screen/suture system 302 can comprise absorbable material.

Figure 12:
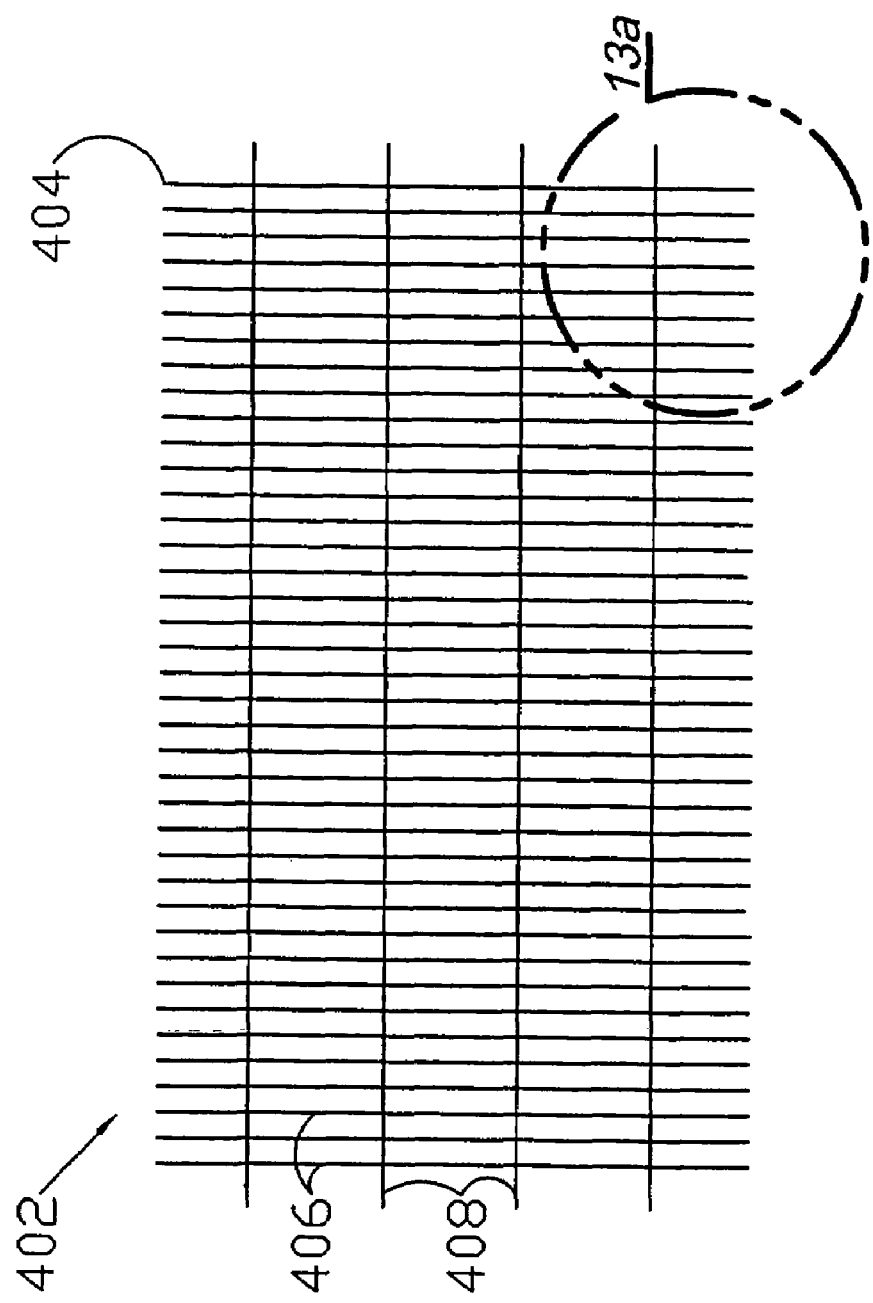
FIG. 12 is a side elevational view of a screen-only closure screen comprising an alternative embodiment of the present invention.
Figure 13B:
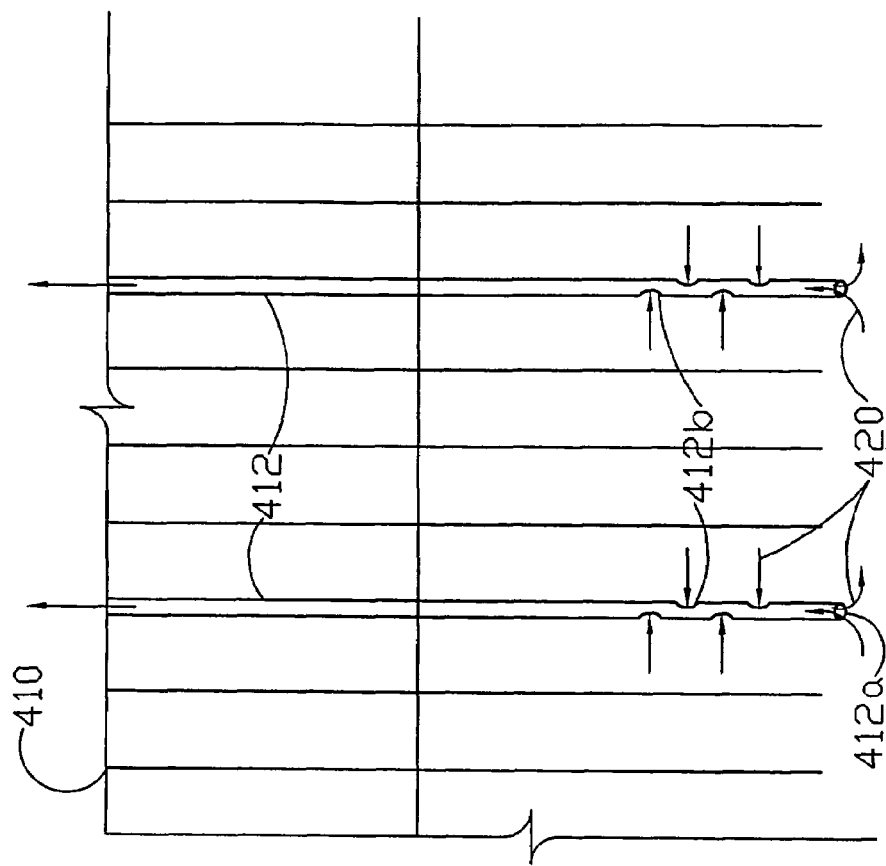
FIG. 13b is an enlarged, fragmentary, side elevational view thereof, showing modified vertical risers.
Figure 13A:
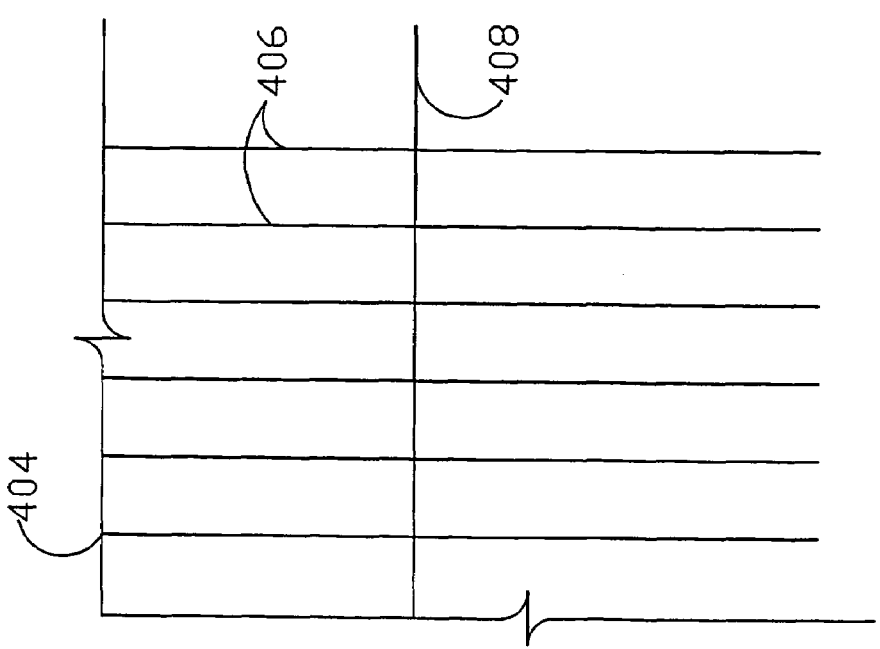
FIG. 13a is an enlarged, fragmentary, side elevational view thereof, taken generally within circle 13a in FIG. 12.

FIGS. 12, 13a and 13b show a modified embodiment screen-only closure screen system 402 and application methodology. A screen or mesh 404, similar to the screen 14 with barbed strands 30 described above, is placed in a separation 4 against the first tissue portion 12a. The second tissue portion 12b is then placed against the screen 404 whereby the separation 4 is closed and can be secured by the mechanical action of the screen 404. The screen 404 can be supplemented with sutures, drainage tubing, I/O devices, and other auxiliary components for purposes of closing the wound edges 12, draining the inside of the tissue separation 4, fighting infection, pain management and all other functionalities associated with the present invention, as discussed elsewhere herein. For example, the screen 404 can be secured with sutures at the subcutaneous level 8. Various fluid interconnecting devices can be utilized as necessary, and can be designed for removal after they serve their initial purpose. External drainage can also be achieved at the dermis level 6 utilizing transfer element subassemblies, such as the example designated 59 and described above (FIG. 7d). Moreover, drainage and irrigation tubing can be installed within the wound 4 alongside or adjacent to the screen 404. It will be appreciated that a screen-only version of the invention can comprise various suitable biocompatible absorbable and nonabsorbable materials, including the materials disclosed above.

FIG. 13a is an enlarged view of the screen 404 and particularly shows barbed strands 406 and horizontal spacers 408, which are connected together in a grid pattern forming the screen 404. FIG. 13b shows an alternative embodiment with a modified screen 410 including vertical risers 412 comprising hollow tubing, which are connected to and spaced by horizontal spacers 408. Fluid flows into and out of the vertical risers 412 through open riser ends 412a and perforations 412b, as indicated by the fluid flow arrows 420.

Figure 14B:
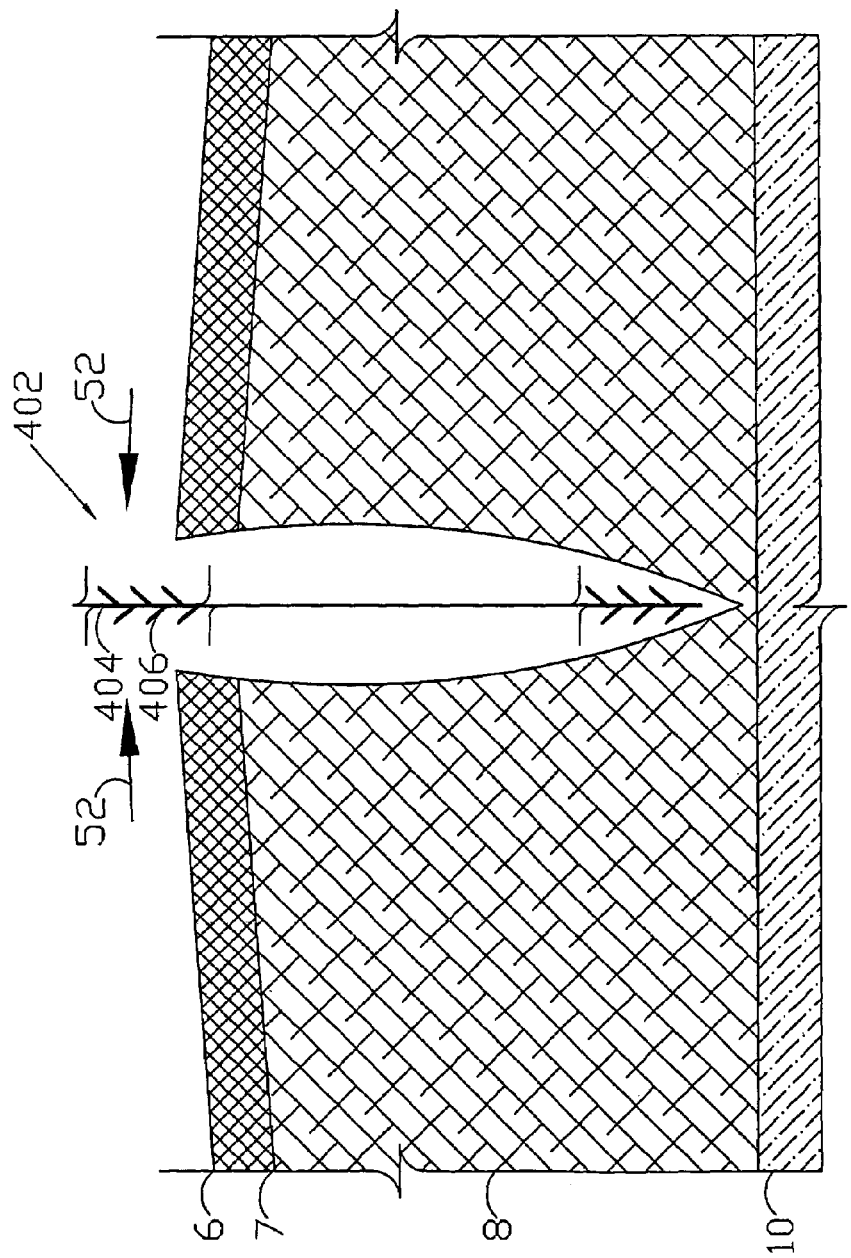
Figure 14C:
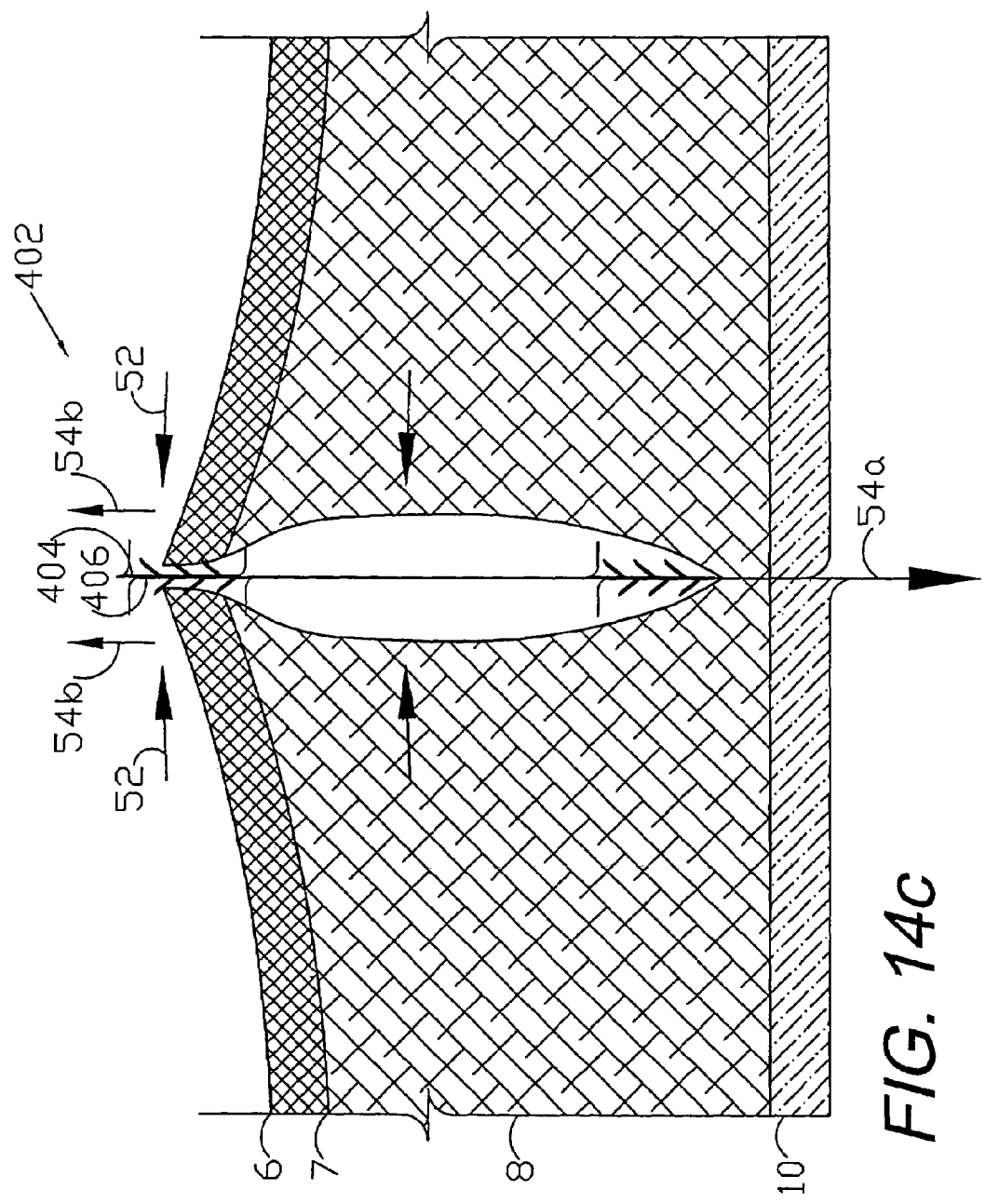
Figure 14D:
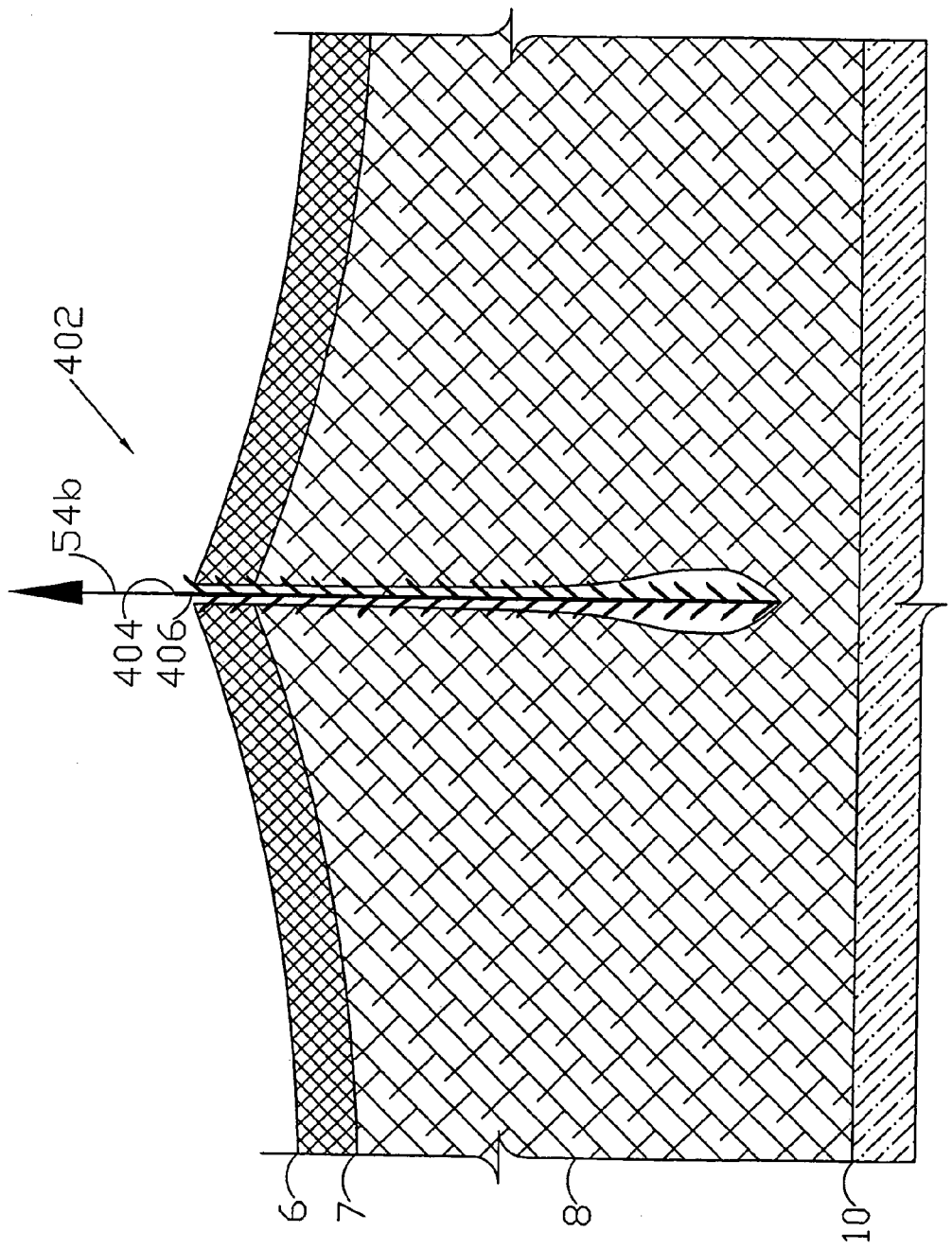
Figure 14E:
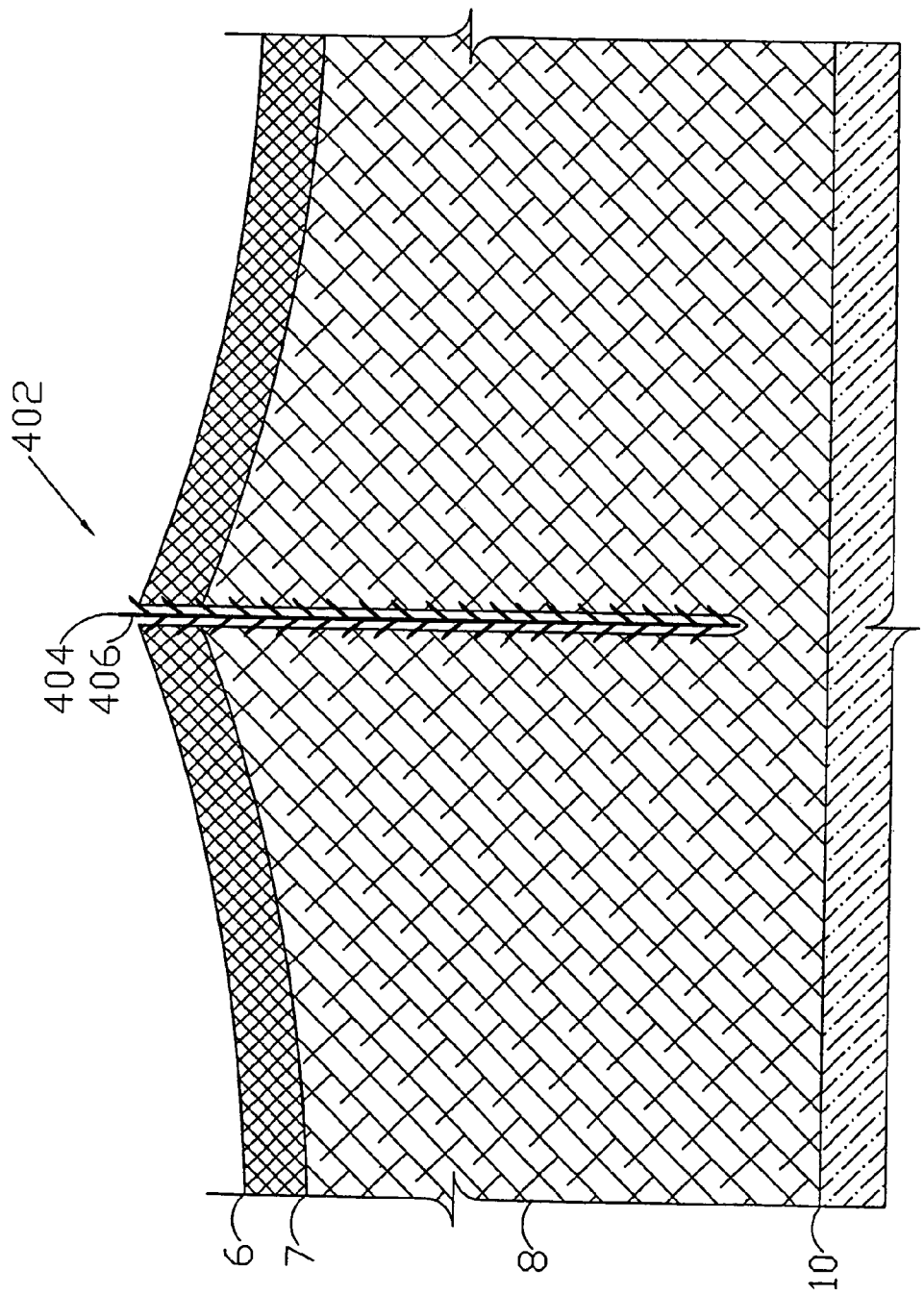
Figure 14F:
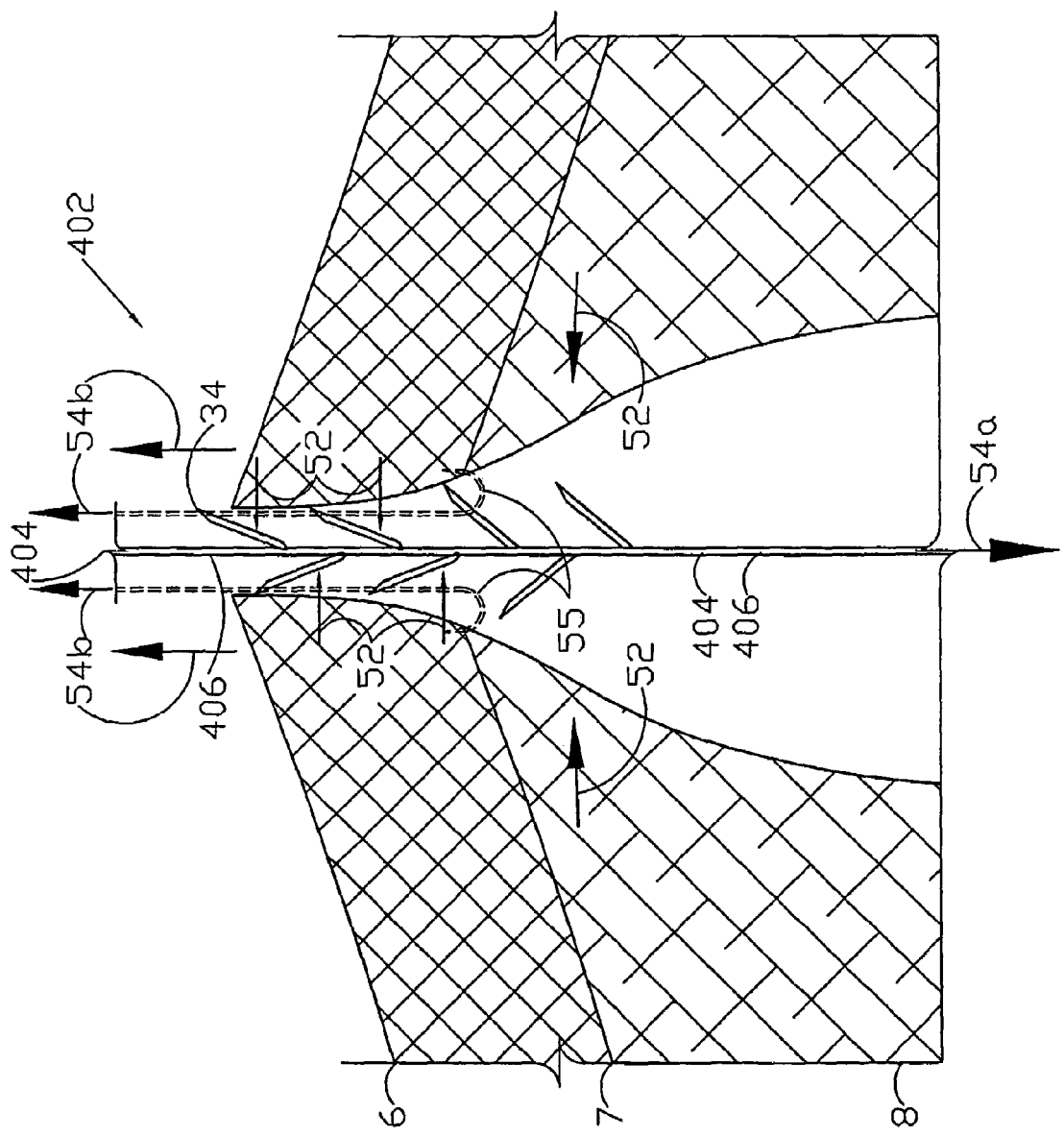
Figure 14G:
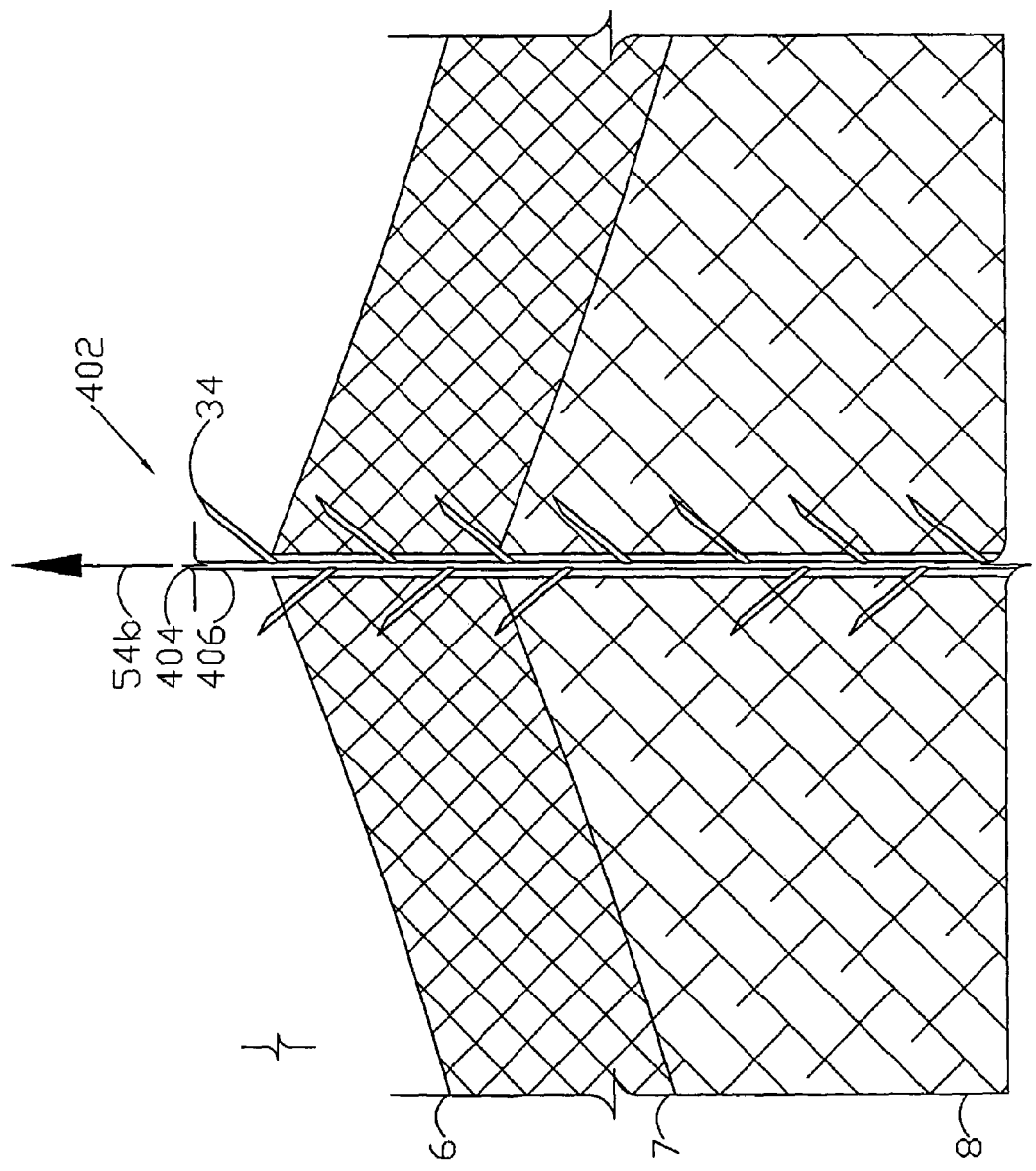

FIGS. 14a-g show the screen 404 installed in a tissue separation 4 and closing same, utilizing the methodology of the present invention. The methodology shown in FIGS. 14a-g is similar to the methodology shown in FIGS. 5a-e and 6a,b. FIG. 14c shows a downward/inward force arrow 54a indicating a direction in which the screen 404 is pushed or guided into the separation.

FIGS. 15a,b and 16a,b show a modified vertical riser 502 comprising bundled tubes 504 secured together at spaced intervals by connectors 506. The normal movement of the patient tends to alternately compress and expand the vertical risers 502, thus providing a "pumping" action for transferring fluid from the wound 4, as indicated by the fluid flow arrows 510. FIGS. 15a,b show a riser 502 in an extended configuration. Compressing the screen 14 longitudinally (i.e., end-to-end) compresses the bundled risers 504 to the configuration shown in FIGS. 16a,b, whereby fluid is drawn into the interstitial space 508 and pumped therefrom when the risers 502 extend.

FIG. 17 shows yet another configuration of a vertical riser 602 with bundled tubes 604, which are closely bunched and define passages 606 for conveying fluid. Such fluid conveyance can be enhanced by a pumping action associated with normal patient movements. Barbs 608 project outwardly from the tubes 604. It will be appreciated that various other bundled tube configurations, such as twisted, braided, etc., can be utilized.

Figure 18:
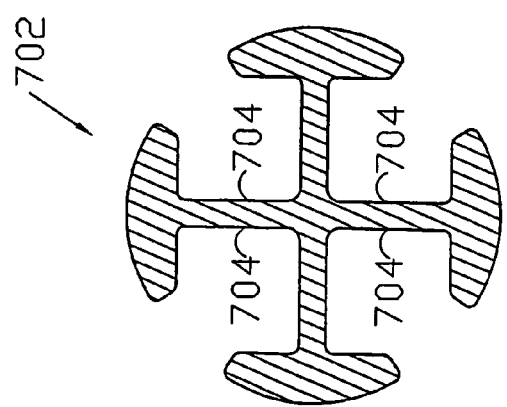
FIG. 18 is a cross-sectional view of a modified vertical riser or perimeter element, comprising a fluted tube.

FIG. 18 shows yet another vertical riser/perimeter member 702 alternative embodiment configuration. The member 702 has a configuration which is commonly referred to as a "fluted" drain and includes longitudinally-extending passages 704. This configuration can substitute for the perimeter members described above and can function to communicate fluid to and from the wound 4 with the input/output subsystem 18.

As additional alternative embodiment configurations for the vertical risers, they can comprise either barbed monofilament strands, similar to strand 30 shown in FIG. 3, or unbarbed monofilament strands. Such monofilament vertical risers can function as passive drains with fluid flowing alongside same. They can extend above the dermis 6 and abut or connect to transfer elements formed in various configurations with suitable absorbent materials. Examples include gauze dressings and transfer element subassemblies, such as 59 shown in FIG. 7d.

Figure 19:
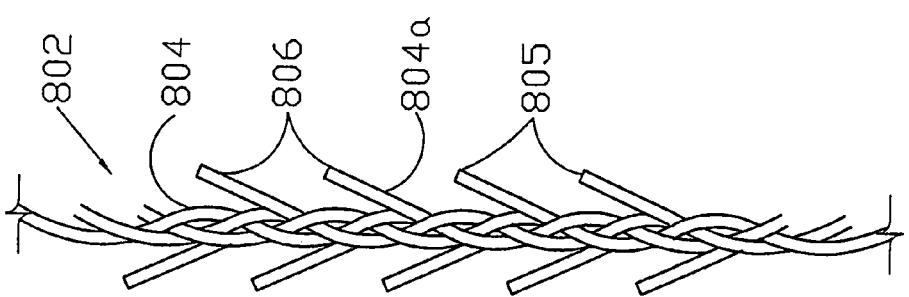
FIG. 19 is an enlarged, fragmentary, side elevational view of a modified barbed strand configuration.

FIG. 19 shows an alternative embodiment strand 802 constructed by twisting and braiding multiple, individual filaments 804. Barbs 805 are formed by respective individual filaments 804a, which terminate at blunt ends 806. The barbs 805 project generally outwardly from the strand 802 and form acute angles with respect to its longitudinal axis. They are adapted for penetrating tissue within a separation 4, as described above. In use, the barbs 805 would normally be oriented in directions generally pointing outwardly from the patient and the tissue separation 4.

Figure 20:
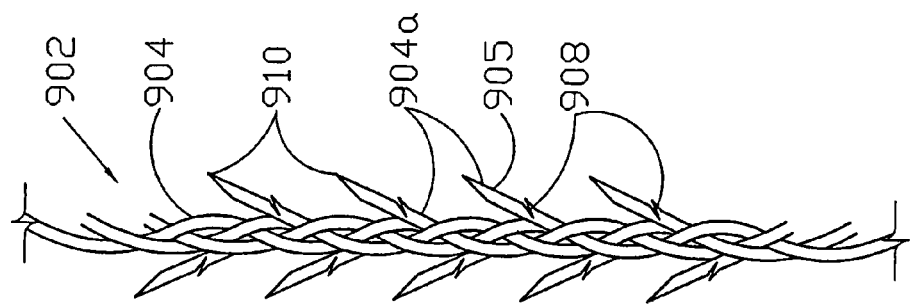
FIG. 20 is an enlarged, fragmentary, side elevational view of another modified barbed strand configuration.

FIG. 20 shows another alternative embodiment strand 902 comprising multiple twisted and braided filaments 904. Barbs 905 are formed from individual filaments 904a and have notches 908 and pointed ends 910. The notches 908 and the ends 910 are configured to allow the barbs 905 to easily extract from the separation edge tissues, whereby the screen is adapted for sliding along the separation edges in order to achieve the proper position.

FIG. 21 shows a further modified screen 1002 with barbs 1004 formed by looping individual filaments 1006 and cutting same at cut locations 1010 spaced inwardly from respective apexes 1008 of the filament loops. In operation, the barbs 1004 slightly penetrate the tissue and are imbedded therein. It will be appreciated that the filaments 1006 are relatively thin in diameter, similar to microfibers, whereby patient comfort is optimized.

FIG. 22 shows yet another modified screen 1102 with barbs 1104 formed by looping individual filaments 1106 and cutting same at locations 1110 spaced inwardly from respective apexes 1108 of the filament loops whereby respective hooks 1112 are formed. The hooks 1112 operate in a manner similar to hook-and-loop fasteners, with the adjacent tissue forming the loop parts of the connections. In operation, the hooks 1112 slightly penetrate the tissue and are imbedded therein. The configurations of the hooks 1112 tend to retain them in the tissue adjacent to the separation 4 whereby the separated first and second tissue portions 12a,b can be closed.

FIG. 23 shows a screen 1202 with a configuration similar to the screen 1002 discussed above, with additional fiber elements or filaments 1204. The additional filaments 1204 tend to lay the filament barbs 1206 over whereby the screen 1202 can be directionally oriented within the wound separation 4 and operate in a manner similar to the screen 14 described above. The barbs 1206 are formed by cutting the apexes 1208 at cut locations 1210.

Similarly, FIG. 24 shows a screen 1302 with additional filaments 1304, which engage the filament loops 1306 and orient same in a direction towards the right as shown in FIG. 24. The slanted orientations of the filament loops 1306 facilitate setting same in the tissue portions 12a,b adjacent to the separation 4 by tugging outwardly on the screen 1302. Repositioning the screen 1302 is also possible, as described above. The filament loops 1306 can be cut at cut locations 1310, which are spaced inwardly from filament loop apexes 1308 whereby hooks 1312 are formed.

It will be appreciated that FIGS. 21-24 disclose screens with barbs and hooks extending from one face thereof. The present invention also includes screens with barbs and hooks extending from both faces.

A closure screen comprising a further modified aspect or embodiment of the invention is shown in FIGS. 25-30 and is generally designated by the reference numeral 1402. The screen 1402 generally comprises a highly flexible panel 1404, which engages and approximates adjacent tissue portions across a separation by the semi-independent action of multiple, individual clips comprising links 1440 (FIG. 25a), which are strung together in respective strands 1408 by suitable flexible filaments or lines 1446. As shown in FIG. 25a, each link 1440 includes a pair of prongs 1442 medially joined by a loop 1444, to which the filament 1446 can be tied or otherwise secured. The loop 1444 thus forms a pivot point or fulcrum with the filament 1446 whereby a rocking action of the link 1440 is facilitated. For example, relative movement of the screen 1402 and the surrounding tissue can impart a torque force, as represented by a torque arrow 1448. The torque force rotates the clip 1440 to a tilted position, as shown by the broken lines in FIG. 25a. Such a rocking action can advance the prongs into the surrounding tissue, thereby enhancing closure. Moreover, relative movement of the surrounding tissue can be accommodated by the combination of screen flexibility and prong movement. Fixation and tissue movement can be variably controlled somewhat by varying the design of the screen 1402 and the clips 1440.

Figure 28:
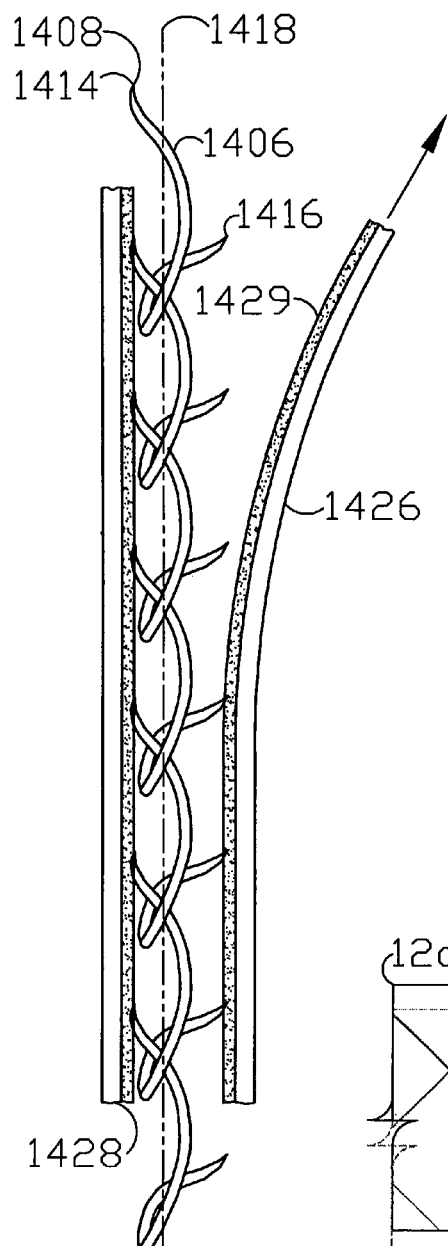
FIG. 28 is a side elevational view of a strand thereof.

FIGS. 26 and 27 show an alternative configuration link 1406 with a first prong 1410 and a second prong 1412, which terminate at pointed, sharpened first and second prong ends 1414, 1416 respectively and are joined by a link body 1413. A link 1417 with a slightly different, more open configuration is shown in FIG. 27a. As shown in FIG. 28, the prongs 1410, 1412 of the link 1406 extend generally outwardly from the body 1413 and generally longitudinally with respect to a longitudinal axis 1418 of a strand 1408, and form opposite, acute angles therewith. The angular orientations of the prongs 1410, 1412 provide a one-way orientation for engagement in a first direction and a disengagement orientation in the opposite direction. Each link 1406 can be integrally formed from a single length of suitable, suture-like material with suitable memory, flexibility/rigidity and biocompatibility characteristics. A U-shaped loop 1420 is formed between the prongs 1410, 1412.

Also as shown in FIG. 28, each loop 1420 receives a respective long prong 1410 from the adjacent link 1406 in a flexible engagement, which can be formed by thermal fusing, ultrasonic welding, adhesive or any other suitable fastening device or method. For example, the link prongs 1410 and the loops 1420 can be configured for the tongue-and-groove or snap-fit, movable interconnection without the necessity of physically bonding the links 1406.

Figure 29:
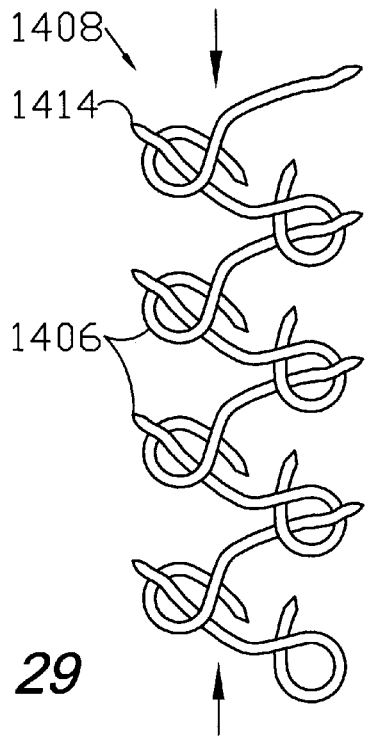
FIG. 29 is a side elevational view of the strand, shown compressed.
Figure 30:
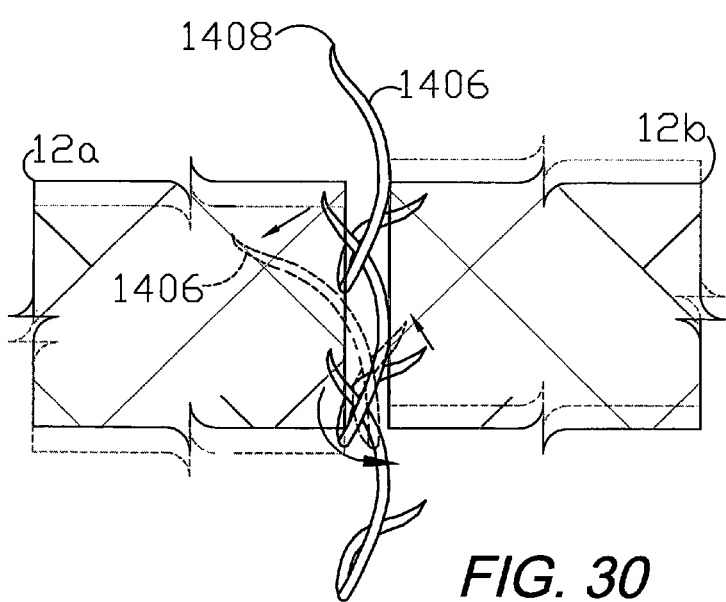
FIG. 30 is an enlarged, cross-sectional, fragmentary view of the strand approximating separated tissue portions.

The strands 1408 can be secured together in forming the panel 1404 by multiple, diagonal filaments 1422, which extend generally transversely, horizontally, longitudinally or, preferably, diagonally with respect to the panel 1404. Like the links 1406, 1417 and 1440, the filaments 1422 can comprise a bioabsorbable or other biocompatible material. The filaments 1422 are preferably highly flexible and thin. FIG. 29 shows the screen panel 1404 in a compressed configuration whereby the first, long prongs 1410 are pivotably received within the respective loops 1420 of adjacent links 1406. FIG. 30 shows such pivotal action of the links 1406 (dashed lines) for accommodating relative tissue movement on either side of the tissue separation The screen 1402 includes a pre-installation enclosure assembly 1424 comprising front and back backing sheets 1426, 1428, which can be provided with a suitable releasable adhesive 1429. The backing sheets 1426, 1428 preferably comprise paper or other material (e.g., Styrofoam® material), which is relatively stiff (as compared to the relatively flimsy panel 1404) for maintaining the flat shape of the closure screen 1402 during handling and placement in the patient and for protection from the sharpened prong tips. An outer edge handling strip 1430 is mounted on the upper edge of perimeter 1432 of the panel 1404 (FIG. 25) and is adapted for grasping manually or with instruments in order to facilitate handling, alignment and placement.

An alternative embodiment or aspect of the present invention is shown in FIGS. 31-33 and includes a modified clip comprising a dual-loop link 1556. Each link 1556 includes first and second prongs 1560, 1562 terminating at respective first and second ends 1564, 1566. Proximal and distal loops 1570, 1571 are provided adjacent to first and second prongs 1560, 1562 respectively.

FIG. 34 shows a modified closure screen construction 1624 using the clips 1604 mounted on a flexible matrix 1626 comprising flexible strips 1628 flexibly interconnected in parallel relation by cross strands 1630. The strips 1628 can be penetrated by the prongs 1614, 1616 whereby all of the clips 1604 can be mounted on one side of a two-sided closure screen 1624. Alternatively, clips 1604 can be mounted on both sides of the strips 1628 in a two-sided closure screen, or on either side with all of the prongs pointing out for a single-sided closure screen.

FIG. 34a shows alternative clip constructions. Clip 1632 has interior prongs 1614 and edge prongs 1616 extending from one face at the top and from the other face at the bottom. Clip 1634 has upper prongs 1614, 1616 extending from opposite faces, and lower prongs 1614, 1616 likewise extending from opposite faces. Clip 1636 includes only one each interior prong 1614 and edge prong 1616, which can extend outwardly from the same face (as shown), or can extend outwardly from opposite faces.

FIG. 35 shows a clip 1632 approximating a tissue separation 4. The respective prongs 1614, 1616 are embedded in the opposed tissue portion edges 12a,b. Relative movement of the tissue can further secure the prongs 1614, 1616, whereby the edges 12a,b are drawn together for healing.

Figure 37:
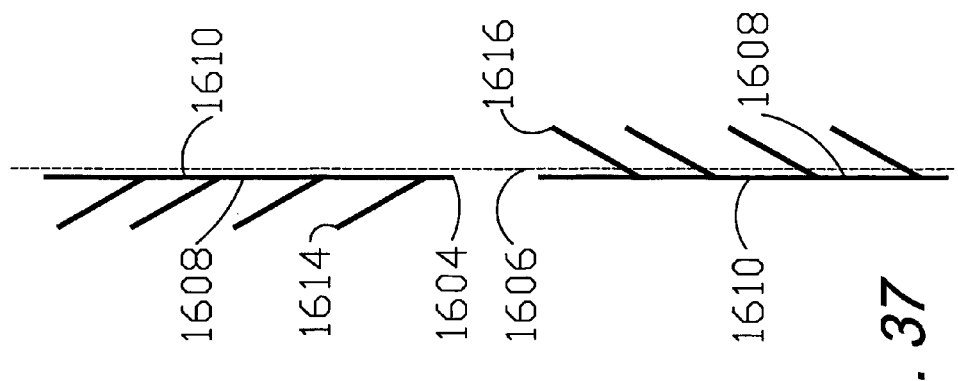
FIG. 37 is a side elevational view of an individual clip thereof, taken generally along line 37 in FIG. 36.
Figure 36:
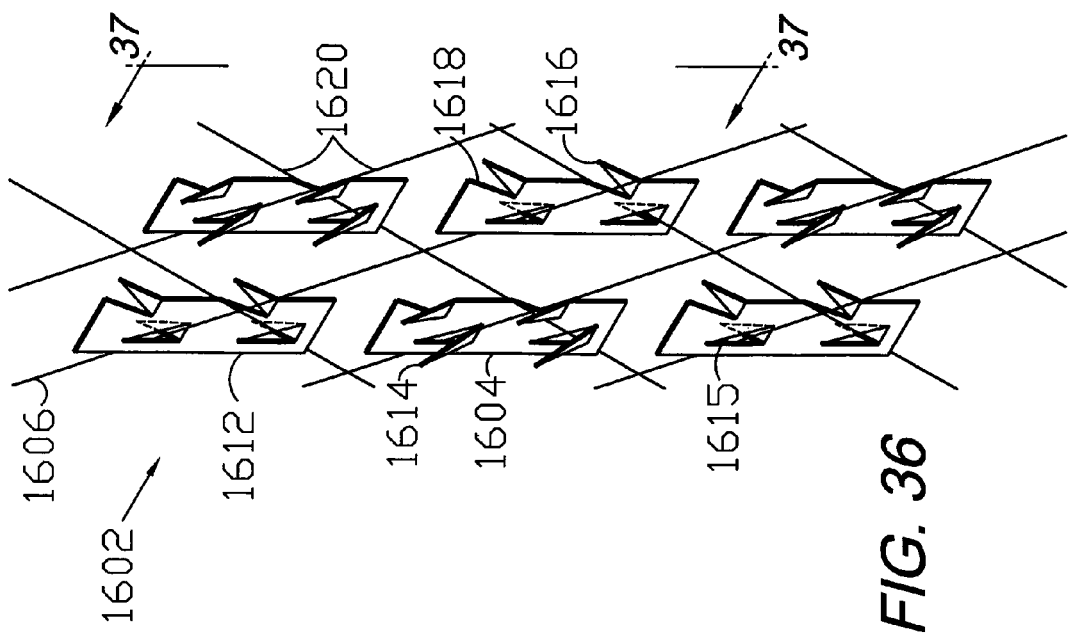
FIG. 36 is a perspective view of another alternative embodiment of the closure screen system including individual clips.

FIGS. 36 and 37 show a closure screen 1602 comprising another aspect or embodiment with multiple, independent rigid clips 1604 on a flexible mesh matrix 1606. Each clip 1604 includes first and second faces 1608, 1610 and a perimeter 1612. Interior prongs 1614 are punched out of the clip 1604, thereby forming clip openings 1615, and perimeter prongs 1616 are punched out adjacent to the perimeter 1612, thereby forming notches 1618. The closure screen 1602 is formed by threading mesh material connector strands 1620 through the clip openings 1615, and securing the strands 1620 together in a crisscross pattern as shown in FIG. 36. The clips 1604 can be alternatingly oriented such that their respective prongs 1614 and 1616 extend from both sides of the screen 1602 (as shown) for two-sided engagement, or they can extend from one face only for single-sided engagement.

FIG. 38 shows several constructions of clips 1852, 1858, 1864 and 1870, stamped from sheet metal or other suitable material and having respective bodies comprising bases 1854, 1860, 1866 and 1872 with sharpened, respective prongs 1856, 1862, 1868 and 1874 projecting therefrom. FIG. 39 shows yet another clip construction 1876 placed in a woven screen or mesh structure 1878, such as those described above, generally coplanar with a clip base 1880. Each clip 1876 has a pair of prongs 1882 projecting outwardly therefrom. The clips 1852, 1858, 1864 and 1870 are adapted for attachment to such screen or mesh structures, resulting in configurations as shown in FIGS. 40-43.

FIGS. 44-49 show different bent-wire clip constructions adapted for mounting on flexible screen or mesh structures. A clip 1802 with a generally rectangular base 1804 and a single prong 1806 projecting outwardly therefrom is shown in FIGS. 44 and 47. FIGS. 45 and 48 show a variant clip 1808 with a generally rectangular base 1810 and prongs 1812. FIGS. 46 and 49 show another variant clip 1814 with a generally U-shaped base 1816 and a pair of prongs 1818 projecting outwardly therefrom. The bases 1804, 1810 and 1818 are adapted to lie generally in a plane formed by the screen or mesh structure, with the prongs 1806, 1812 and 1818 projecting outwardly therefrom at suitable acute angles, such as about 30-45 degrees. The prongs can have sharpened tips, as shown.

FIG. 50 shows a clip 1902 comprising another alternative embodiment clip configuration. As shown in FIGS. 51a-c, clip configurations 1902a-c can be formed with four each primary prongs 1904 and four each secondary prongs 1906, which can extend from one or both faces of a body 1908 of a respective clip 1902. FIGS. 52a-c show side elevations of the clip configurations 1902a-c. A center slot 1903 is formed in the body 1908 and notches 1905 are formed around its perimeter. The center slot 1903 and the notches 1905 are adapted to receive filaments or other flexible members in a closure screen matrix including multiple clips 1902, whereby the clips 1902 can be somewhat fixed in position in a flexible closure screen construction.

FIGS. 53 and 53a show another alternative embodiment clip configuration 1910 with curved primary prongs 1912 and straight secondary prongs 1914. The curvature of the primary prongs 1912 facilitates drawing the separated tissue portions 12a, 12b together, as shown in FIG. 53a and as presented by the lateral force arrows 1916. Such lateral forces can be applied with a NPWT device, such as The V.A.C.® System™ manufactured by Kinetic Concepts, Inc. of San Antonio, Tex. The secondary prongs 1914 help prevent disengagement when the closure screen is subjected to a downward (i.e. into the body) force as represented by a force arrow 1917.

FIGS. 54 and 54a show another alternative embodiment clip configuration with a curved body 1922. The configuration causes a trailing primary prong 1924 to engage and penetrate tissue first, whereafter the clip 1920 rotates, embedding a leading primary prong 1926. The torque (clockwise as shown by torque arrow 1927) imparted to the clip 1920 by a tugging force, for example along the force arrow 1928 on an encircling filament 1929, tends to facilitate secure anchorage in tissue 12b.

FIGS. 55 and 55a show another alternative embodiment clip-configuration 1930 with flexible, collapsible prongs 1932, 1934, which are collapsed when the clips are between backing screens 1936a,b. When the backing screens 1936a,b are removed (FIG. 55a), the prongs 1932, 1934 spring outwardly to extended orientations and are adapted for penetrating the tissue 12b.

The alternative configuration clips 1910, 1920 and 1930 can be formed from a common clip template, such as that shown at 1902 in FIG. 50, with a bendable body and prongs adapted for bending into various desired configurations. Moreover, the clips can be mounted in various screen matrices.

FIG. 56 shows another alternative embodiment clip configuration 1940 with primary and secondary prongs 1942, 1944 having respective barbs 1942a, 1942b. FIG. 57 shows another alternative embodiment clip configuration 1950 with primary and secondary prongs 1952, 1954 having respective barbs 1952a, 1952b. FIG. 58 shows another alternative embodiment clip configuration 1960 with quadrilateral primary and secondary prongs 1962, 1964 having respective trocar-shaped ends 1962a, 1964a. Various other clip, base and prong configurations, combinations and orientations can be utilized with the present invention.

FIG. 59 shows a closure clip system 1970 comprising another alternative embodiment of the present invention. The system 1970 includes a screen 1972, which can comprise, for example, any of the clip and screen constructions described above. The screen 1972 is placed within the tissue separation 4 and an extension 1974 is folded over onto the skin surface on either or both sides of the tissue separation 4. Affixing the screen, or the strips comprising same, helps to support the links and clips in position against downward loads. The adhesive on the screen or strips would not adhere to the wet tissue of the separation edges, but would appear to the dry skin surface 6. The screen or strips can be made of rapidly dissolving, bioabsorbable material reinforced with longitudinal strands of slower dissolving material, similar to the construction of strand reinforced tape available as STERI-STRIP® from the 3M Company of St. Paul, Minn. With the extension 1974 folded over the skin surface 6 and the rest of the clips above the wound 4 removed or cut away, the extension(s) 1974 can be affixed to the skin surface 6 with STERI-STRIP or some other suitable tape 1976. In lieu of-or in addition to the tape 1976, surgical staples 1978 can be used to close the tissue separation and affix the extension(s) 1974 to the skin surface 6. Lateral closure forces can optionally be applied to the tissue separation 4 shown in FIG. 59 by applying a NPWT source 1980 such as The V.A.C.® System™ over the closure. A suitable drape 1982 can be applied over the negative pressure source 1980 in sealing relation with the skin around the perimeter.

Figure 60:
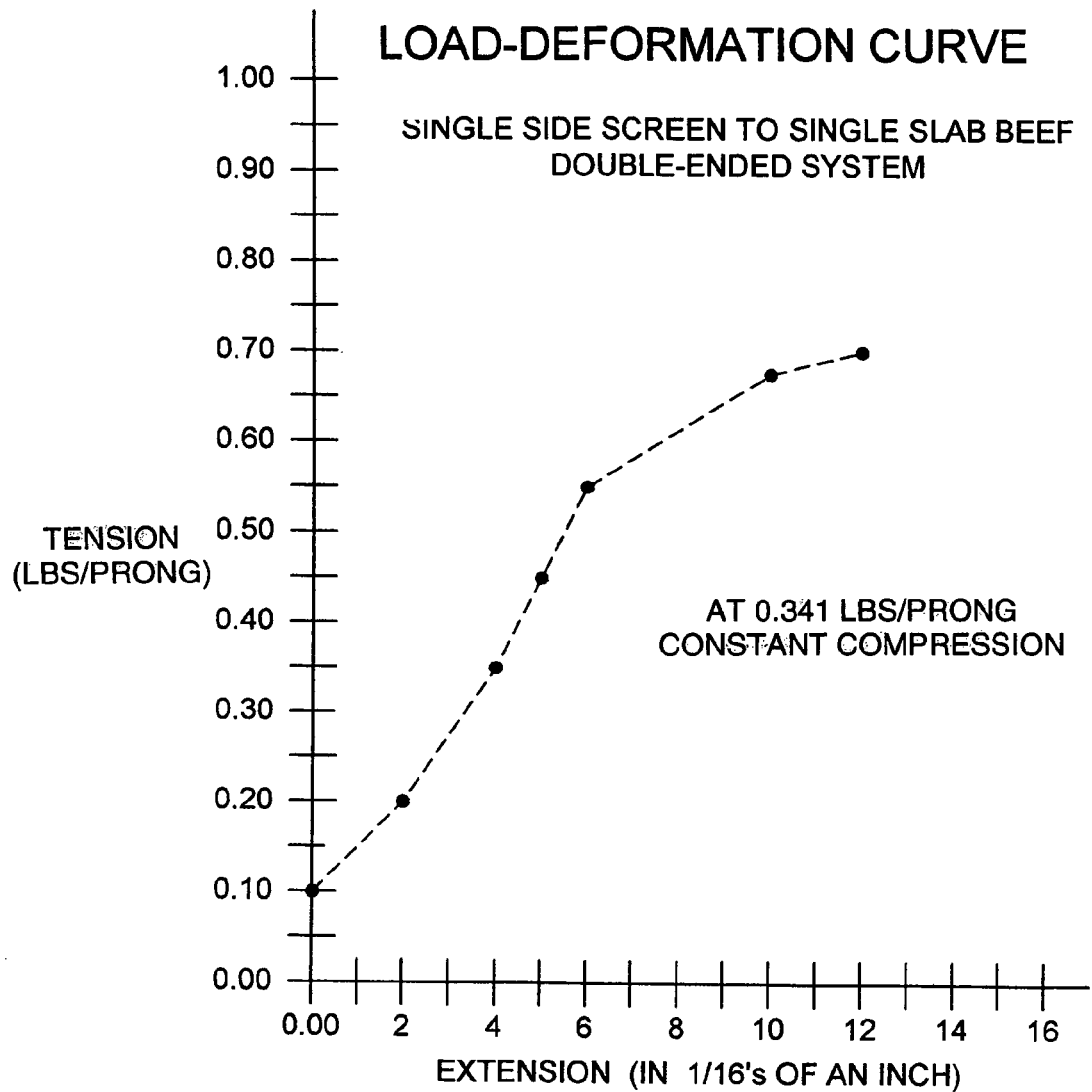
FIG. 60 is a graph showing a load-deformation curve (tension in relation to extension) for a test involving a screen comprising multiple clips and embodying the present invention.
Figure 61:
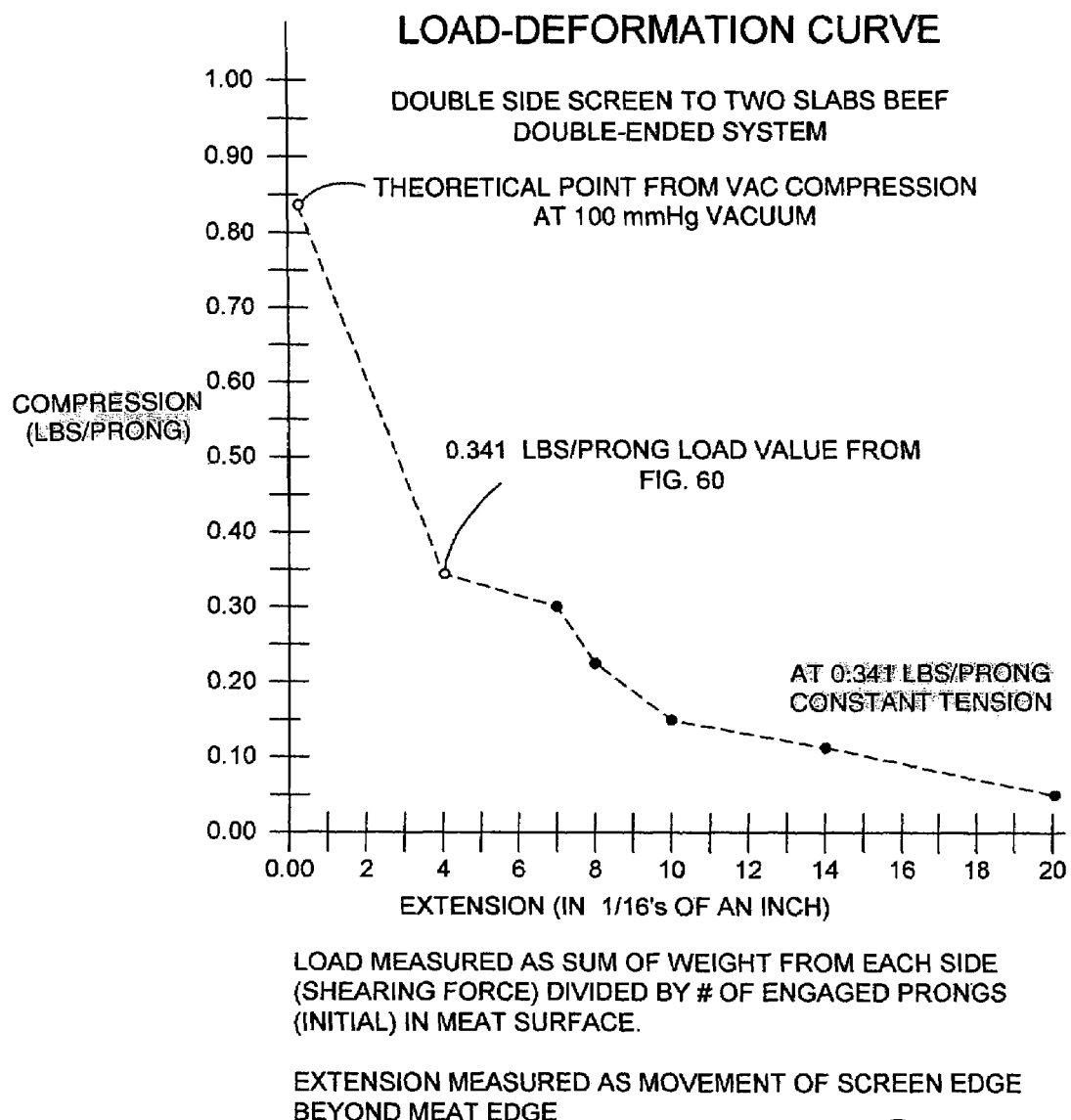
FIG. 61 is a graph showing another load deformation curve (compression in relation to extension) for another test involving the multiple-clip screen.

FIG. 60 shows a load-deformation curve showing the relationship of tension measured in pounds per prong and extension of the system measured in sixteenths of an inch using a multiple-clip screen similar to the closure screen 1602 shown in FIG. 36. The screen was retained between two pieces of raw beefsteak, which were subjected to varying shear stress (tensile) forces, as plotted on the Y axis of the graph in FIG. 60. Compression forces equal to 0.341 pounds/prong were applied to the beefsteak pieces with the closure screen clamped therebetween. Such compression forces were applied mechanically to produce the load-deformation curve shown in FIG. 60. FIG. 61 shows a load-deformation curve for varying compression forces at a constant tension force of 0.341 pounds/prong. A theoretical point projected from the load-deformation curve of FIG. 61 represents 100 mmHg of vacuum compression, as applied with The V.A.C.® System™ in the model tested. FIG. 60 shows that increasing tension loads produce increasing extension of the model (positive relationship). FIG. 61 shows that compression loads and extension have an inverse relationship, with greater extension occurring with lesser compression loads.

It is to be understood that while certain forms of the present invention have been illustrated and described herein, it is not to be limited to the specific forms or arrangement of parts described and shown.

Having thus described the invention, what is claimed as new and desired to be secured by Letters Patent is:

1. A medical closure method for internally closing a separation between first and second tissue portions with opposed first and second tissue edges, which method comprises the steps of:

providing multiple clips wherein each clip comprises a length of wire bent to form first and second prongs and first and second loops in each clip;

interconnecting respective first and second loops of adjacent clips and thereby forming multiple, flexible strands each comprising multiple interconnected clips;

maintaining said first prongs of said interconnected clips in a first orientation and maintaining said second prongs of said interconnected clips in a second orientation by said interconnected loops:

positioning said multiple strands in generally parallel, juxtaposed relation:

forming a flexible screen by providing multiple, flexible filaments, extending said filaments transversely or diagonally across said juxtaposed strands and connecting said filaments to said strands;

presenting opposite first and second screen faces and a screen distal edge;

extending a first set of clip prongs from said first screen face towards said screen distal edge;

extending a second set of clip prongs from said second screen face towards said screen distal edge;

forming an acute angle between each said clip prong and a respective screen face:

placing said screen in said tissue separation between said opposed tissue edges;

penetrating said first tissue edge with said first set of prongs:

generally approximating said tissue edges;

penetrating said second tissue edge with said second set of prongs;

pulling said screen distal edge distally;

further embedding said prongs in said tissue edges respectively; and further approximating said tissue edges.

2. A medical closure method for internally closing a separation between first and second tissue portions with opposed first and second tissue edges, which method comprises the steps of:

providing multiple clips wherein each said clip has;

with a planar body having first and second faces and a perimeter;

and having a prong formed from said clip body;

aligning multiple said clips;

flexibly interconnecting said multiple aligned clips to form a flexible strand;

forming multiple said strands;

positioning said multiple strands in generally parallel, juxtaposed relation;

forming a flexible screen by providing multiple, flexible filaments, extending said filaments transversely or diagonally across said juxtaposed strands and connecting said filaments to said strands;

presenting opposite first and second screen faces and a screen distal edge;

angling a first set of said clip prongs from said first screen face towards said screen distal edge;

angling a second set of said clip prongs from said second screen face towards said screen distal edge;

forming an acute angle between each said clip prong and a respective screen face;

placing said screen in said tissue separation between said opposed tissue edges;

penetrating said first tissue edge with said first set of prongs;

generally approximating said tissue edges;

penetrating said second tissue edge with said second set of prongs;

pulling said screen distal edge distally;

further embedding said prongs in said tissue edges respectively; and further approximating said tissue edges.

3. A medical closure method for internally closing a separation between first and second tissue portions with opposed first and second tissue edges, which method comprises the steps of:

providing multiple clips;

each said clip having a prong;

aligning multiple said clips;

flexibly interconnecting multiple aligned clips;

forming multiple, flexible strands each comprising multiple interconnected clips;

positioning said multiple strands in generally parallel, juxtaposed relation;

forming a flexible screen by providing multiple, flexible filaments, extending said filaments transversely or diagonally across said juxtaposed strands and connecting said filaments to said strands;

presenting opposite first and second screen faces and a screen distal edge;

angling a first set of clip prongs outwardly from said first screen face towards said screen distal edge;

angling a second set of clip prongs outwardly from said second screen face towards said screen distal edge;

forming an acute angle between each said clip prong and a respective screen face;

placing said screen in said tissue separation between said opposed tissue edges;

penetrating said first tissue edge with said first set of prongs;

generally approximating said tissue edges;

penetrating said second tissue edge with said second set of prongs;

extending said screen distal edge distally beyond a skin surface at said first and second tissue portions;

pulling said screen distal edge distally;

tensioning said screen;

further embedding said prongs in said tissue edges respectively;

further approximating said tissue edges; anchoring said screen extended distal edge to said skin surface at said closed tissue portions;

fluidically connecting a hydrophobic foam material to said screen extended distal edge at said skin surface;

draping said foam material and the surrounding skin surface;

applying a negative pressure to said foam material through said drape;

approximating said tissue portions at said skin surface with said negative pressure; and draining said wound via said foam material with said negative pressure.

* * * * *